US012401970B2

(12) United States Patent
Joao

(10) Patent No.: US 12,401,970 B2
(45) Date of Patent: *Aug. 26, 2025

(54) PERSONAL MONITORING APPARATUS AND METHODS

(71) Applicant: Raymond Anthony Joao, Yonkers, NY (US)

(72) Inventor: Raymond Anthony Joao, Yonkers, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/225,734

(22) Filed: Jul. 25, 2023

(65) Prior Publication Data

US 2023/0413014 A1 Dec. 21, 2023

Related U.S. Application Data

(63) Continuation of application No. 16/909,622, filed on Jun. 23, 2020, now Pat. No. 11,765,547.
(Continued)

(51) Int. Cl.
*H04W 4/029* (2018.01)
*G01S 19/13* (2010.01)
(Continued)

(52) U.S. Cl.
CPC .......... *H04W 4/029* (2018.02); *G01S 19/13* (2013.01); *G06K 7/10366* (2013.01); *G07C 9/38* (2020.01);
(Continued)

(58) Field of Classification Search
CPC .......... G06K 7/10425; G06K 7/10366; H04W 4/029; H04W 4/40; H04W 4/80;
(Continued)

(56) References Cited

U.S. PATENT DOCUMENTS 6,028,513 A 2/2000 Addy
6,772,598 B1 8/2004 Rinehart
(Continued)

OTHER PUBLICATIONS

Office Action, mailed Feb. 10, 2025, U.S. Appl. No. 17/946,086.
(Continued)

*Primary Examiner* — Congvan Tran
(74) *Attorney, Agent, or Firm* — Raymond A. Joao, Esq.

(57) ABSTRACT

An apparatus, including a monitoring device including a database which stores travel itinerary or a travel schedule information of an individual, a global positioning device; and an RFID tag; an RFID reader; and a computer. The computer generates a first message containing information regarding a date and a time when the RFID tag was detected or read and information regarding an address of the venue or information regarding a position or location of the vehicle. The computer transmits the first message to a user communication device, the monitoring device, or a central processing computer. The personal monitoring device determines that the individual is not following the travel itinerary or travel schedule, or that the individual has deviated from the travel itinerary or travel schedule. The monitoring device generates a second message containing information regarding a location of the individual and transmits the second message to the user communication device.

20 Claims, 14 Drawing Sheets

Related U.S. Application Data

(60) Provisional application No. 62/880,608, filed on Jul. 30, 2019.

(51) Int. Cl.
    | | |
    |---|---|
    | *G06K 7/10* | (2006.01) |
    | *G07C 9/38* | (2020.01) |
    | *A61B 5/00* | (2006.01) |
    | *G06Q 50/14* | (2012.01) |
    | *G06Q 50/26* | (2012.01) |
    | *G16H 10/65* | (2018.01) |
    | *G16H 40/67* | (2018.01) |

(52) U.S. Cl.
    CPC ............ *A61B 5/0002* (2013.01); *G06Q 50/14* (2013.01); *G06Q 50/265* (2013.01); *G16H 10/65* (2018.01); *G16H 40/67* (2018.01)

(58) Field of Classification Search
    CPC .. G07C 9/27; G07C 9/38; G01S 19/14; G01S 19/13; G01S 5/0295; G01S 2205/01; G16H 40/20; G16H 10/60; G16H 10/65; G16H 40/67; G06Q 50/265; G06Q 50/14; A61B 5/0002
    See application file for complete search history.

(56) References Cited

U.S. PATENT DOCUMENTS

| | | | |
|---|---|---|---|
| 6,847,295 | B1 | 1/2005 | Taliaferro et al. |
| 8,115,625 | B2 | 2/2012 | Yoshioka et al. |
| 8,255,830 | B2 | 8/2012 | Ording et al. |
| 8,909,391 | B1 | 12/2014 | Peeters et al. |
| 9,351,124 | B1 | 5/2016 | Shelton |
| 9,460,596 | B1 | 10/2016 | Moses |
| 9,759,570 | B2 | 9/2017 | Joao et al. |
| 9,804,596 | B1 | 10/2017 | Slavin |
| 11,234,205 | B2 * | 1/2022 | Mulaosmanovic ............ G06Q 10/0833 |
| 11,581,099 | B1 | 2/2023 | Rufo et al. |
| 11,626,001 | B1 | 4/2023 | Khmelev et al. |
| 2005/0230472 | A1 * | 10/2005 | Chang ............ G07G 1/14 235/383 |
| 2006/0099969 | A1 | 5/2006 | Staton et al. |
| 2006/0099971 | A1 | 5/2006 | Staton et al. |
| 2006/0199612 | A1 | 9/2006 | Beyer, Jr. et al. |
| 2007/0085993 | A1 | 4/2007 | Brown, Jr. |
| 2007/0126573 | A1 | 6/2007 | Valania |
| 2007/0152980 | A1 | 7/2007 | Kocienda et al. |
| 2007/0171046 | A1 | 7/2007 | Diem |
| 2008/0032703 | A1 | 2/2008 | Krumm et al. |
| 2009/0219403 | A1 | 9/2009 | Mccaffrey et al. |
| 2009/0309751 | A1 | 12/2009 | Kano et al. |
| 2009/0322511 | A1 | 12/2009 | Mckenna et al. |
| 2010/0216509 | A1 | 8/2010 | Riemer et al. |
| 2011/0046920 | A1 | 2/2011 | Amis |
| 2011/0248838 | A1 | 10/2011 | Krahenbuhl et al. |
| 2011/0298613 | A1 | 12/2011 | Ben Ayed |
| 2012/0105632 | A1 | 5/2012 | Renkis |
| 2012/0122558 | A1 | 5/2012 | Lyons et al. |
| 2012/0242501 | A1 | 9/2012 | Tran et al. |
| 2012/0259633 | A1 | 10/2012 | Aihara et al. |
| 2013/0027837 | A1 | 1/2013 | Myers |
| 2013/0029730 | A1 | 1/2013 | Harada et al. |
| 2013/0120136 | A1 | 5/2013 | Johnson et al. |
| 2013/0122968 | A1 | 5/2013 | Miura et al. |
| 2013/0260360 | A1 | 10/2013 | Baurmann et al. |
| 2014/0368601 | A1 | 12/2014 | Decharms |
| 2015/0134143 | A1 | 5/2015 | Willenborg |
| 2015/0205298 | A1 | 7/2015 | Stoschek et al. |
| 2016/0042637 | A1 | 2/2016 | Cahill |
| 2016/0227361 | A1 | 8/2016 | Booth et al. |
| 2017/0092109 | A1 | 3/2017 | Trundle et al. |
| 2017/0162031 | A1 | 6/2017 | Drolshagen et al. |
| 2017/0193308 | A1 | 7/2017 | Buyse et al. |
| 2017/0308692 | A1 | 10/2017 | Yano |
| 2017/0318446 | A1 | 11/2017 | Lee |
| 2018/0275859 | A1 | 9/2018 | Hodge |
| 2018/0322749 | A1 | 11/2018 | Kempel et al. |
| 2019/0156496 | A1 | 5/2019 | Leduc |
| 2019/0340560 | A1 | 11/2019 | Sundia et al. |
| 2019/0378391 | A1 | 12/2019 | Miniard |
| 2020/0134530 | A1 | 4/2020 | Clevenger et al. |
| 2020/0137212 | A1 | 4/2020 | Borse |
| 2020/0146550 | A1 | 5/2020 | Tunnell et al. |
| 2020/0267936 | A1 | 8/2020 | Tran |
| 2021/0061466 | A1 | 3/2021 | Gee |
| 2021/0129982 | A1 | 5/2021 | Collins et al. |
| 2021/0315300 | A1 | 10/2021 | Briggs et al. |
| 2021/0347500 | A1 | 11/2021 | Hagan |
| 2021/0349066 | A1 | 11/2021 | Chilla et al. |
| 2021/0350713 | A1 | 11/2021 | Van Meeteren et al. |
| 2021/0403132 | A1 | 12/2021 | Pourmasiha |
| 2022/0035384 | A1 | 2/2022 | Subramanian et al. |
| 2022/0083987 | A1 | 3/2022 | Bhunia et al. |
| 2022/0143523 | A1 | 5/2022 | Ng et al. |
| 2022/0383029 | A1 | 12/2022 | Kaleko et al. |
| 2023/0033199 | A1 | 2/2023 | Joao |
| 2023/0070772 | A1 | 3/2023 | Bingham et al. |
| 2023/0129369 | A1 | 4/2023 | Womble et al. |
| 2023/0131370 | A1 | 4/2023 | Gorski et al. |

OTHER PUBLICATIONS

Office Action, mailed Nov. 5, 2024, U.S. Appl. No. 18/223,700.
Office Action, mailed Apr. 10, 2024, U.S. Appl. No. 17/946,086.
Office Action, mailed Oct. 8, 2024, U.S. Appl. No. 17/946,086.
Office Action, mailed Mar. 13, 2025, U.S. Appl. No. 18/225,115.

* cited by examiner

PERSONAL MONITORING APPARATUS AND METHODS

RELATED APPLICATIONS

This application is a continuation application of U.S. patent application Ser. No. 16/909,622, filed Jun. 23, 2020, and entitled "PERSONAL MONITORING APPARATUS AND METHODS", the subject matter and teachings of which are hereby incorporated by reference herein in their entirety. U.S. patent application Ser. No. 16/909,622 claims the benefit of the priority of U.S. Provisional Patent Application Ser. No. 62/880,608, filed Jul. 30, 2019, and entitled "PERSONAL MONITORING APPARATUS AND METHODS", the subject matter and teachings of which are hereby incorporated by reference herein in their entirety.

FIELD OF THE INVENTION

The present invention pertains to a personal monitoring apparatus and methods for individuals of all ages and, in particular, to a personal monitoring apparatus and methods for individuals of all ages which can be utilized to monitor infants, children, the elderly, or individuals of any and/or all ages, and/or to monitor their respective position or location utilizing RFID technologies and/or global positioning information in connection with expected itineraries and/or schedules.

BACKGROUND OF THE INVENTION

All too often we hear horror stories about children and adults being lost, abducted, left in vehicles, left on school buses, or falling ill, or are found in, or placed in, any type or kind of dangerous or precarious predicament. We also hear of individuals and, in particular, elderly individuals, becoming lost, disoriented, falling ill, or otherwise being in other precarious predicaments. Lastly, we also hear of individuals of any and/or all ages suddenly falling ill or being in need of emergency medical attention or in need of other assistance.

While so-called "amber alerts" provide a public notification system or method which alerts or notifies the public regarding a missing child, and while so-called "silver alerts" are a public notification system or method which alerts or notifies the public regarding a missing person, a missing adult, or a missing elderly person afflicted with a condition such as Alzheimer's, Dementia, or any other condition, these public notification systems are flawed in that they rely on members of the public to actually find, look out for, and/or find and/or report, the missing child or missing person. If the missing child or missing person becomes disoriented, falls ill, gets lost in an isolated area, becomes fearful and/or tries to hide from others, the above-described public notification systems can be futile in finding the missing child or missing person.

Providing children and adults of all ages with personal communication devices such as cellular telephones, personal digital assistants, or like communication devices, can also prove useless if and when the child or adult falls ill, panics, is unable to speak, becomes unconscious, or is otherwise unable to utilize such a personal communication device.

In this regard, it is submitted that the prior art systems, which seek to find, locate, and provide assistance to or for, missing children and/or adults have many shortcomings and do not provide for an effective means by which to find, locate, and assist, these missing children and adults.

SUMMARY OF THE INVENTION

The present invention pertains to a personal monitoring apparatus and methods for individuals of all ages, which overcomes the shortcomings of the prior art. The present invention pertains to a personal monitoring apparatus and methods for individuals of all ages, and, in particular, to a personal monitoring apparatus and methods for individuals of all ages which can be utilized to monitor infants, children, the elderly, or individuals of any and/or all ages, and/or to monitor their respective position or location utilizing RFID technologies and/or global positioning information in connection with expected itineraries and/or schedules. The present invention also pertains to a personal monitoring apparatus and methods and, in particular, to a personal monitoring apparatus and methods which can be utilized to monitor infants, children, the elderly, or individuals of any and/or all ages, and/or to monitor their position or location, their whereabouts, their surroundings, their vital signs, their physiological measurements, states, or condition, and/or any individual and/or individuals with whom they may come into contact.

The present invention can also provide an apparatus and methods which can be utilized to monitor and/or to track the whereabouts and/or the travels of an individual at any time, to compare an individual's current whereabouts to a location where they should be, ought to be, or are expected to be, and/or to provide an alert, or to provide a notification, to the individual, a parent of the individual, a child of the individual, a relative of the individual, a caregiver of the individual, an employer of the individual, a law enforcement agency or law enforcement personnel, emergency services personnel, a third party, or any other person or entity, when the individual is located at a location where they should not be, where they ought not be, where they are not expected to be, or when they have deviated from, or are deviating from, a planned, an expected, or a desired, travel route, or a planned, expected, or desired, itinerary or schedule.

For example, the present invention can be used to monitor the whereabouts, the location, or the travel, of a child of any age, a child having special needs, a child who has become injured or ill, or a child who has become lost, missing, or who has become a victim of foul play. As and for another example, the present invention can be used to monitor the whereabouts, the location, or the travel, of an adult or an elderly individual, of any age, an adult or an elderly individual having special needs, an adult or an elderly individual who has become ill or injured, or an adult or an elderly individual who has become lost, missing, or disoriented, or who has, or may have, become a victim of foul play.

The present invention can also be utilized to provide information or an indication, to the individual, or to any person(s) with whom the individual may come into contact, which can provide information indicative of the individual being where he or she should not be, indicative that the individual is lost, indicative that the individual is or might be injured or ill, or indicative that the individual is disoriented, or in need of help or assistance.

The present invention can also be utilized to provide information or an indication, to a parent of the individual, to a child of the individual, to a relative of the individual, to a caregiver of the individual, to an employer of the individual, to a law enforcement agency or law enforcement personnel, to an emergency services personnel, to any third party, or to any other person or entity, when the individual has been determined to be lost, injured, ill, disoriented, or otherwise in need of help or assistance.

The present invention can also be utilized to obtain, record, store, and/or provide, healthcare information or physiological data and/or information, or any other information regarding the state or status of an individual, including, but not limited to, the individual's heart rate, blood pressure, body temperature, blood sugar level, or any other physical condition, physiological condition, or healthcare condition, which can be measured or can be measurable by any wearable device or by any implanted device or implantable device.

The present invention can also be utilized to initiate, establish, and/or maintain, a communication link, or a telephone call, with and between any of the herein-described personal monitoring devices with any of the herein-described user communication devices, central processing computers, and/or law enforcement communication devices and/or emergency services communication devices. In this regard, for example, a line of communication can be established with and/or between the personal monitoring device of a lost, mission, or ill, child and a user communication device of, associated with, or used by, the child's parent, relative, caregiver, or other authorized person. The present invention can also be utilized to provide an open, and/or speakerphone-operated, line of communication with the personal monitoring device so that a respective parent, relative, caregiver, or other authorized person can, using a user communication device, speak to, or engage in conversation with, the child or with any individual with whom the child comes into contact so as to facilitate finding the child, helping the child find help or his or her way back to a safe location, and/or making sure that the child is brought to a place of safety and/or is safely returned home or to another safe location, and/or to make sure that the child's needs are provided for until being reunited with his or her parent(s), a caregiver, or law enforcement. The present invention can also be utilized in a same, a similar, or an analogous, manner in providing personal monitoring for adults and elderly individuals of any age.

The present invention can also be utilized in order to establish, and to provide services for, personal monitoring accounts for individuals. A personal monitoring account can be assigned to an individual in order to provide any number or monitoring services for that individual. For example, a personal monitoring account can be utilized to allow any other authorized individual, person, or entity, to monitor, and/or to track location, position, or movement, of an individual, to communicate with the individual at any time, to communicate with people in the vicinity of the individual, to obtain information regarding the position, location, or whereabouts, of the individual, persons with whom the individual may be in contact with, or may have come into contact with, or the individual's itinerary, schedule, travels, and/or to obtain video and/or audio information regarding the individual, his or her travels, locations, and/or any other information regarding the individual. One or more personal monitoring accounts can be set up by or for an individual. In this regard, an individual can have one personal monitoring account ("PMA") or a plurality of personal monitoring accounts.

The present invention can be utilized to provide a number of various features and functionalities which can be useful in providing personal monitoring services and operations for infants, children, and adults, of any ages. The present invention can also be utilized to provide personal monitoring services and operations for and regarding pets and animals of any type or kind.

The apparatus of the present invention includes a personal monitoring device which is, or can be, a cellular telephone, a mobile telephone or wireless telephone, a Smartphone, a personal digital assistant, or any other suitable device. The personal monitoring device can also be any wearable device. The personal monitoring device can be equipped with the communication equipment typically found in cellular telephones, mobile telephones or wireless telephones, Smartphones, personal digital assistants, or any other suitable devices, for facilitating a two-way communication with other individuals or entities and/or with communications devices, computers, equipment, or any other communication equipment used by any individuals or entities described herein or otherwise. The personal monitoring device can also be equipped with global positioning system (GPS) device or equipment. The personal monitoring device can also be equipped with navigation equipment such as are typically found in commercially available GPS navigation devices and equipment which are used to assist motorists and individuals traveling in motor vehicles, on bicycles, or on foot, in navigating from a location to a destination. The personal monitoring device can also be equipped with a radio-frequency identification ("RFID") tag or any number of RFID tags.

The personal monitoring device can also be equipped with global positioning system (GPS) equipment and navigation equipment which can allow the personal monitoring device to act in a stand-alone manner, without having to obtain any navigation information from any external device or computer. The personal monitoring device can be equipped to receive, and provide to a user, navigation data and/or information, including, but not limited to, navigation instructions, which is obtained from an external computer or communication device or a service provider computer or communication device.

The personal monitoring device can also be any communication device, computer, personal computer, laptop computer, notebook computer, Smartphone or smartphone, smart telephone, cellular telephone, personal digital assistant, tablet, tablet computer, watch, smart watch, or wearable device or computer, an implantable device or computer, an item of jewelry, eyeglasses, or any accessory, or any combination of same, or any equivalent of same, which can be utilized by any person, individual, or entity, who or which utilizes the apparatus and methods of the present invention. The personal monitoring device can also be a server computer, a mainframe computer, a mini-computer, a microcomputer, or any other computer or device for suiting the needs of the particular user.

Any number of personal monitoring devices can be utilized by or in conjunction with the apparatus of the present invention. The personal monitoring device can communicate, in a bi-directional manner and/or otherwise, with and/or can operate in conjunction with any of the computers, communication devices, and/or computer systems, described herein as being utilized in connection with the apparatus and methods of the present invention.

The apparatus of the present invention also includes a central processing computer or central processing computer system. The central processing computer can be any computer or computer system or can be any computer which can be operated in a network environment with other computers or a server computer.

The central processing computer can provide control over the apparatus and can perform any of the various processing services, routines, and/or functions, described herein as being performed by the same. The central processing computer can be a single computer or a system of computers and/or can include a plurality of computers or computer systems which are utilized in conjunction with one another. The central processing computer can provide personal monitoring services for or regarding any number of individuals and/or entities and/or can provide personal monitoring services for or regarding any number of individuals and/or entities who or which need, want, or desire, to monitor, to monitor the whereabouts of, and/or who or which desire to be notified regarding the whereabouts, location, healthcare status, or any occurrence of or regarding any event which may give rise to a need to find, locate, and/or monitor, a location of any child, adult, elderly person, or any individual of any age.

Any number of central processing computers can be utilized by or in conjunction with the apparatus of the present invention. The central processing computer(s) can communicate, in a bi-directional manner and/or otherwise, with, and/or can operate in conjunction with, the personal monitoring device and/or any of the other communication devices, computers, and/or computer systems, associated with or used by any of the individuals and/or entities who or which utilize the apparatus and methods of the present invention.

The apparatus of the present invention also includes a user communication device or computer which is associated with, or which can be used by, any one or more of any of the herein-described users, individuals, or entities, who or which utilize the apparatus and methods of the present invention. Any number of user communication devices can be utilized by or in conjunction with any user or any individual or entity who or which utilizes the apparatus and methods of the present invention, and any number of user communication devices can be utilized in conjunction with the apparatus and methods of the present invention.

The user communication device(s) can communicate, in a bi-directional manner and/or otherwise, with, and/or can operate in conjunction with the personal monitoring device and/or the central processing computer and/or any of the other herein-described communication devices, computers, and/or computer systems, associated with or used by any of the individuals and/or entities who or which utilize the apparatus and methods of the present invention.

The apparatus of the present invention also includes a law enforcement communication device or computer which is associated with, or which can be used by, any law enforcement agency or department which utilizes the apparatus and methods of the present invention. Any number of law enforcement communication devices can be utilized by or in conjunction with any law enforcement agency or department which utilizes the apparatus and methods of the present invention, and any number of law enforcement communication devices can be utilized in conjunction with the apparatus and methods of the present invention.

The law enforcement communication device(s) can communicate, in a bi-directional manner and/or otherwise, with, and/or can operate in conjunction with the personal monitoring device, the central processing computer, the user communication device, and/or any of the other herein-described communication devices, computers, and/or computer systems, associated with or used by any of the individuals and/or entities who or which utilize the apparatus and methods of the present invention.

The apparatus of the present invention also includes an emergency services provider communication device or computer which is associated with, or which can be used by, any emergency services provider, agency, or department, which utilizes the apparatus and methods of the present invention. Any number of emergency services provider communication devices can be utilized by or in conjunction with any emergency services provider, agency, or department, which utilizes the apparatus and methods of the present invention, and any number of emergency services provider communication devices can be utilized in conjunction with the apparatus and methods of the present invention.

The emergency services provider communication device(s) can communicate, in a bi-directional manner and/or otherwise, with, and/or can operate in conjunction with the personal monitoring device, the central processing computer, the user communication device, the law enforcement communication device, and/or any of the other herein-described communication devices, computers, and/or computer systems, associated with or used by any of the individuals and/or entities who or which utilize the apparatus and methods of the present invention.

The apparatus of the present invention can also include a healthcare records computer or communication device which stores an electronic healthcare record or electronic healthcare records for any of the herein-described individuals who or which can be monitored using the apparatus and methods of the present invention. The healthcare records computer can also store healthcare records of any individual, children, adults, elderly persons, or any individual of any age, who is to be monitored by and using the apparatus and methods of the present invention as well as any healthcare records of, for, or regarding, any relatives of any of these individuals.

The healthcare records computer can serve to store and house an electronic healthcare record or any number of electronic healthcare records. The healthcare records computer can also be utilized to facilitate cloud storage of any electronic healthcare record(s).

The healthcare records computer(s) can communicate, in a bi-directional manner and/or otherwise, with, and/or can operate in conjunction with, the personal monitoring device, the central processing computer, the user communication device, the law enforcement communication device, the emergency services provider communication device, and/or any of the other communication devices, computers, and/or computer systems, associated with or used by any of the individuals and/or entities who or which utilize and/or operate in conjunction with the apparatus of the present invention.

The apparatus of the present invention also includes any number of radio frequency identification (RFID) tags. An RFID tag can be attached to, affixed to, or placed on or in, a personal monitoring device. The RFID tag can be worn by the individual or attached to an article of clothing worn by the individual. The RFID tags can be of any suitable type or kind, and can be selected from among the various types or kinds of RFID tags which are available in the marketplace as of the filing date of this patent application. The RFID tags can be passive RFID tags or can be active RFID tags. The RFID tags should be waterproof, washable, and/or otherwise be capable of being cleaned, and they should be temperature resistant and durable, in order to be utilized in all types or kinds of environments, in all types or kinds of weather conditions, and/or in order to be utilized in conjunction with all types and/or kinds of clothing or apparel, shoes, boots, hats, gloves, accessories, and other wearable objects and/or articles. Any type or kind of RFID tag can be utilized in connection with the apparatus of the present invention provided that the respective RFID tag is suitable for use in its particular application.

Any number of RFID tags can be utilized in connection with the apparatus of the present invention. Further, passive RFID tags can be utilized in any situation where a respective tag may not be capable of having its own power source. In applications or embodiments where RFID tags can be provided with a power source, then active RFID tags can be used. For example, if an RFID tag can be powered by a power source of the personal monitoring device, then the RFID tag can be an active RFID tag. Passive RFID tags can provide for the most convenient use since they do not have or require a power source, but rather, they can be energized and operate when activated by a suitable RFID reader device.

The apparatus of the present invention also includes any number of RFID reader systems which can be, or which can include, any suitable RFID reader. Each RFID reader system can be reader for passive RFID tags or can be a reader for active RFID tags depending upon the application. Each RFID reader system can be utilized to read any of the RFID tags described herein as being utilized in connection with the apparatus of the present invention. The RFID reader system can include any number of RFID readers which can service any single venue or any single vehicle, or the RFID reader system can include any number of RFID readers which can service any number of venues and/or any number of vehicles.

The RFID reader system can communicate with and/or can interact with any of the personal monitoring devices, the central processing computers, the user communication devices, the law enforcement communication devices, the emergency services provider communication devices, the healthcare records computers, and/or any of the other communication devices, computers, and/or computer systems, described herein and/or associated with, or used by, any of the individuals and/or entities who or which utilize and/or operate in conjunction with the apparatus of the present invention. The RFID reader system can communicate with, and/or be linked with, any of the personal monitoring devices, the central processing computers, the user communication devices, the law enforcement communication devices, the emergency services provider communication devices, the healthcare records computers, and/or any of the other communication devices, computers, and/or computer systems, described herein, via a wired communication network, a wireless communication network, or via any combination of wired and/or wireless communication networks.

The apparatus of the present invention can also include any number of venue computers, with each venue/vehicle computer being assigned to a respective venue, which can be any premises or building, school, place of work, or other physical location, and/or which can be the site of social events, entertainment events, sporting events, or any other events or gatherings, as well as which can be any type or kind of place of business, educational institution, or other public venue, or being assigned to respective vehicle, which can be any land, sea, or air, vehicle, which can be any automobile of motor vehicle, train, subway train, bus, or other mass transportation vehicle, or any boat, ship, submarine, or any marine vehicle, or any airplane, jet, helicopter, ort any other air vehicle, and/or which be any space vehicle, and/or any vehicle or entity in which an individual can travel from one location to another. Venues can also include, but not be limited to stores, places of business, malls, shopping malls, public gathering places, private gathering places, restaurants, cafes, stadiums, arenas, and/or any other place where people can gather for an event or participate in any activity or activities, and/or any other place or location where the apparatus of the present invention can be utilized.

Each venue/vehicle computer can include, can be equipped with, or can have assigned thereto, an RFID reader or RFID reader systems, or any number of RFID readers or RFID reader systems. Each venue/vehicle computer should be equipped with one or more RFID reader or RFID reader systems for reading any of the RFID tags which can enter the respective venue or vehicle, and/or which can leave the respective venue or vehicle with which the venue/vehicle computer is associated.

The venue/vehicle computer can communicate with and/or interact with any of the personal monitoring devices, the central processing computers, the user communication devices, the law enforcement communication devices, the emergency services provider communication devices, the healthcare records computers, the RFID reader systems, and/or any of the other communication devices, computers, and/or computer systems, described herein and/or associated with, or used by, any of the individuals and/or entities who or which utilize and/or operate in conjunction with the apparatus of the present invention. The venue/vehicle computer can communicate with, and/or be linked with, any of the personal monitoring devices, the central processing computers, the user communication devices, the law enforcement communication devices, the emergency services provider communication devices, the healthcare records computers, the RFID reader systems, and/or any of the other communication devices, computers, and/or computer systems, described herein. The venue/vehicle computer can communicate with, and/or be linked with, any of the personal monitoring devices, the central processing computers, the user communication devices, the law enforcement communication devices, the emergency services provider communication devices, and/or any of the other communication devices, computers, and/or computer systems, described herein, via a wired communication network, a wireless communication network, or via any combination of wired and/or wireless communication networks.

The venue/vehicle computer can be associated with, can utilized at, and/or can be used by any authorized person at, the respective venue or vehicle in order to interface with, and/or interact with, the central processing computer or with any other computers and communication devices described herein as being used in or with the apparatus of the present invention. Each venue/vehicle computer can include any number of computers, server computers, or computer systems.

Each of the herein-described central processing computers, law enforcement communication devices, emergency services provider communication devices, healthcare records computers, RFID reader systems, and/or venue/vehicle computers, can also have a website or websites associated therewith.

Any of the personal monitoring device(s), the central processing computer(s), the user communication device(s), the law enforcement communication device(s), the emergency services provider communication device(s), the healthcare records computer(s), the RFID reader systems, and/or the venue/vehicle computer, can be any computer or communication device, including, but not limited to, a personal computer, a home computer, a server computer, or any computer capable of being utilized in a network or capable of being utilized with other computers in a network, or a hand-held computer, a palmtop computer, a laptop computer, a personal communication device, a cellular telephone, a wireless telephone, a mobile telephone, a digital television, an interactive television, a digital television, a personal digital assistant, a telephone, a digital telephone, a television, an interactive television, a beeper, a pager, and/or a watch or a Smart watch, and/or any wearable device, computer or communication device.

Each of the personal monitoring device(s), the central processing computer(s), the user communication device(s), the law enforcement communication device(s), the emergency services provider communication device(s), the healthcare records computer(s), the RFID reader systems, and/or the venue/vehicle computers, can transmit information to, as well as receive information from, any of the computers or communication devices described herein. In this regard, each of the computers or communication devices described herein can communicate with, process information from, and/or share data and/or information with, each other and/or any other computer(s) or communication device(s) described herein and/or utilized in conjunction with the apparatus of the present invention. In this manner, any of the respective computer(s) or communication device(s) described herein can communicate with any other computer(s) or communication device(s) described herein in a bi-directional manner.

The present invention can be utilized on, over, and/or via, the Internet and/or the World Wide Web, and/or on, over, and/or via, any other communication network, and/or on, over, and/or via, any wireless communication network and/or any cellular communication network. The present invention can also utilize wireless Internet and/or World Wide Web services, equipment and/or devices. The central processing computer(s) can have a web site or web sites associated therewith. Each of the other computers or communication devices described herein can also have a web site or web sites associated with same.

Although the Internet and/or the World Wide Web can be preferred communication system and/or medium utilized, the present invention, in any and/or all of the embodiments described herein, can also be utilized with any appropriate communication network or system including, but not limited to, a telecommunication network or system, a telephone communication network or system, a cellular communication network or system, a wireless communication network or system, a line or wired communication network or system, a wireless Internet network or system, a wireless World Wide Web network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, a cable television network or system, and/or any other communication network or system, and/or any combination of the above communication networks or systems.

Any of the personal monitoring device(s), the central processing computer(s), the user communication device(s), the law enforcement communication device(s), the emergency services provider communication device(s), the healthcare records computer(s), the RFID reader systems, and/or the venue/vehicle computers, can communicate with one another, and/or be linked to one another, over or via any communication network, telecommunication network, telephone network, a line-connected network, and/or a wireless communication network, and/or the Internet and/or the World Wide Web. Each of the computers or communication devices described herein can be linked with any other computers or communication devices directly or indirectly with one another so as to facilitate a direct or indirect bi-directional communication between said respective computers or communication devices. Communications between each of the computers or communication devices described herein can also involve an e-mail server or e-mail servers in those instances when e-mails are described as being used to transmit or to send any of the information, signals, messages, reports, notification messages, or any other communications, described herein, by or between any of the computers or communication devices described herein, or when any of the information, signals, messages, reports, notification messages, or any other computers or communications, described herein, are transmitted by and/or between any of the parties described herein and/or by or between any of the computers or communication devices described herein, or any other computers or communication devices, computer systems, communication network equipment, server computers, etc., or any other devices used or needed, in order to facilitate communications or the transmission of any of the herein-described information, signals, messages, reports, notification messages, or any other communications.

Each of the personal monitoring device(s), the central processing computer(s), the user communication device(s), the law enforcement communication device(s), the emergency services provider communication device(s), the healthcare records computer(s), the RFID reader systems, and/or the venue/vehicle computers, can communicate in a bi-directional manner with, and/or can send and/or receive signals, data, information, messages, reports, notification messages, alerts, or any other communications or electronic communication transmissions, to, from and/or between, any other, or any number of, other personal monitoring device(s), central processing computer(s), user communication device(s), law enforcement communication device(s), emergency services provider communication device(s), healthcare records computer(s), RFID reader systems, and/or venue/vehicle computers.

Each of the personal monitoring device(s), the central processing computer(s), the user communication device(s), the law enforcement communication device(s), the emergency services provider communication device(s), the healthcare records computer(s), the RFID reader systems, and/or the venue/vehicle computers, can be linked to or with any other personal monitoring device(s), central processing computer(s), user communication device(s), law enforcement communication device(s), emergency services provider communication device(s), healthcare records computer(s), RFID reader systems, and/or venue/vehicle computers, via a wired link or line or a wireless link.

Each of the personal monitoring device(s), the central processing computer(s), the user communication device(s), the law enforcement communication device(s), the emergency services provider communication device(s), the healthcare records computer(s), the RFID reader systems, and/or the venue/vehicle computers, can be connected with, or linked to or with, the central processing computer(s).

Any and/or all of the signals, data, information, messages, reports, notification messages, or any other communications, described herein as being transmitted from one device, computer, or communication device, to another device, computer, or communication device, can be, or can be included in, or can be attached to, an e-mail message, an instant messaging message, an electronic transmission, or an electronic data transmission or electronic data interchange, or can be transmitted via any other data or information transmission, and/or can be transmitted via or using any appropriate or necessary computer(s) or device(s).

Each of the personal monitoring device(s), the central processing computer(s), the user communication device(s), the law enforcement communication device(s), the emergency services provider communication device(s), the healthcare records computer(s), the RFID reader systems, and/or the venue/vehicle computers, can transmit data and/or information using TCP/IP, as well as any other Internet and/or World Wide Web, and/or communication, protocols.

The apparatus of the present invention can utilize electronic commerce technologies and security methods, techniques and technologies, including any encryption or security technologies and/or techniques, in any and/or all of the instances of data and/or information processing, and/or data and/or information transmission described herein.

The personal monitoring device includes a central processing unit or CPU which can be a microprocessor or any other suitable processing device. The CPU can also be a microcomputer, a minicomputer, a macro-computer, and/or a mainframe computer, depending upon the application. The personal monitoring device can also include a random access memory device(s) (RAM), a read only memory device(s) (ROM), each of which is connected to, or linked with, the CPU, and a user input device, for inputting and/or entering data and/or information and/or instructions and/or commands into the personal monitoring device. The input device can include any one or more of a keyboard, a scanner, a user pointing device, such as, for example, a mouse, a stylus, a touch pad, and/or an audio input device, a microphone, an audio recording device, and/or a video input device, a camera or any number of cameras, a video recording device, and/or any device, electronic and/or otherwise, which can be utilized for inputting and/or entering data and/or information and/or instructions and/or commands into the personal monitoring device.

The input device(s) can also be or can include a pulse rate monitor or measurement device or equipment, a heart rate monitor of measurement device or equipment, a blood sugar monitor or measurement device or equipment, a blood pressure monitor or measurement device or equipment, a blood alcohol monitor or measurement device or equipment, a pacemaker, a defibrillator, a thermometer for measuring an individual's body temperature, or any other device, monitor, or measurement, device or equipment, and/or any electrical or bio-medical device or equipment, which can measure an individual's physical condition, health condition, health status, healthcare condition, or physiological condition or status, or any other biological or biometric data and/or information.

Any of the herein-described pulse rate monitors or measurement devices or equipment, heart rate monitors of measurement devices or equipment, blood sugar monitors or measurement devices or equipment, blood pressure monitors or measurement devices or equipment, blood alcohol monitors or measurement devices or equipment, pacemakers, defibrillators, thermometers, or any other devices, monitors, or measurement devices or equipment, and/or any electrical or bio-medical devices or equipment, can be wirelessly linked with and/or to the CPU and/or to the personal monitoring device and can be wearable, attachable to clothing, or implantable. The input device(s) can also include a thermometer for measuring the temperature on the exterior of the personal monitoring device.

The personal monitoring device can also include a display device for displaying data and/or information to a user or operator. The personal monitoring device also includes a transmitter(s), for transmitting signals and/or data and/or information to any one or more of the central processing computer(s), the user communication device(s), the law enforcement communication device(s), the emergency services provider communication device(s), the healthcare records computer(s), the RFID reader system(s), the venue/vehicle computer(s), and/or any other personal monitoring device(s), which can be utilized in conjunction with the present invention. The personal monitoring device also includes a receiver(s) for receiving signals and/or data and/or information from any one or more of the central processing computer(s), the user communication device(s), the law enforcement communication device(s), the emergency services provider communication device(s), the healthcare records computer(s), the RFID reader system(s), the venue/vehicle computer(s), and/or any other personal monitoring device(s), which can be utilized in conjunction with the present invention.

The personal monitoring device also includes a database(s) for storing any data and/or information, as well as any software programs and/or software applications, and/or any other information needed for performing any of the functions or functionalities described herein as being performed by the personal monitoring device and/or the apparatus of the present invention.

The personal monitoring device can also include an output device(s) for outputting any of the data, information, and/or reports, described herein as being generated by or via the personal monitoring device. The output device(s) can be a display screen, a speaker, a printer, a display of any type or kind, an indicator light, a transmitter, a modem, and/or any other device which can be used to output data or information of any kind or type. The output device(s) can also include a beacon or a homing beacon which can transmit or provide a signal, a distress signal, or any other indication, from the personal monitoring device which can be utilized determine the position, location, and/or movement, of the personal monitoring device.

The personal monitoring device can also include a video and/or audio recording device(s) which can include a camera and/or a video recording device for recording pictures or video and/or video clips and/or a microphone or an audio recording device for recording audio or audio clips which can be recorded by, and/or transmitted live, by or from the personal monitoring device, or which can be recorded by, and stored at or in, the personal monitoring device for transmission by or from the personal monitoring device at a later time. The video and/or audio recording device(s) can be utilized to facilitate video conferencing, video chatting, and/or audio conferencing, and/or video and audio conferencing, between users of the personal monitoring device and any user of any other computer or communication device described herein.

The personal monitoring device can also include a global positioning system (GPS) device which can be utilized to determine or ascertain the location or position of the personal monitoring device at any time and/or to track movement of the personal monitoring device. The personal monitoring device can also include device functional equipment systems or devices, which can include any the necessary communications systems or devices which are typically found in cellular telephones or wireless telephones and/or which can allow the personal monitoring device to function as a cellular telephone or a wireless telephone. The functional equipment systems or devices can also include a global positioning system (GPS) device which can be utilized to determine or ascertain the location or position of the personal monitoring device at any time and which can be also be used to track movement of the personal monitoring device. The functional equipment systems or devices can also include navigation equipment or devices which are typically found in navigation devices or equipment and which an be utilized to allow the personal monitoring device to function and/or to operate as a GPS equipped navigation device. The personal monitoring device can also function as a stand alone navigation device, meaning that it can perform any and/or all needed and desired navigation tasks and functions without any interaction with an external computer or device, and/or without having to access a computer over any communication network in order to obtain navigation data, information, and/or instructions, for providing navigation data, information, and/or instructions, to a user of the personal monitoring device.

The functional equipment systems or devices can also include a "kill" switch or associated hardware and/or software for disabling and/or deactivating the personal monitoring device in instances when same might be lost or stolen, so as to prevent its use by another person and/or to prevent any access to any data and/or information stored therein, thereby rendering the personal monitoring device useless to another person after being reported, or discovered as being, lost or stolen.

The personal monitoring device can also operate in conjunction with an external computer or device in order to obtain navigation data, information, and/or instructions, so as to provide same to a user of the personal monitoring device. The personal monitoring device can process navigation data, information, and/or instructions, on its own as well as receive at least some navigation data, information, and/or instructions, from an external computer or device, in order to provide navigation data, information, and/or instructions, to a user of the personal monitoring device.

The functional equipment systems or devices can also include any combination of hardware and/or software for disabling the on/off switch of the personal monitoring device, so that the personal monitoring device cannot be shut-off, or so that no operation or function of the personal monitoring device can be terminated, and/or so that a telephone call, a telephone communication link, or a communication line or link, cannot be turned off or terminated, by or at the personal communication device. In this regard, in the case of an emergency, no telephone call and/or communication line or link between the personal monitoring device and any user communication device(s), the or any central processing computer(s), the or any law enforcement communication device(s), the or any emergency services provider communication device(s), and/or the or any healthcare records computer(s), can be terminated at or by the personal monitoring device, so that a communication line, link, or channel can always be maintained with the personal monitoring device.

In this regard, for example, if a child is lost, a telephone call and/or communication line, link, or channel, with and between the child and his or her parent can be maintained without the risk of the call being terminated at or by the personal monitoring device. In this regard, the parent can continue to speak with and communication with the child, can obtain position or location information from or via the personal monitoring device, can track the personal monitoring device, and/or can obtain any other information from and/or via the personal monitoring device, without losing contact with the child and/or his or her personal monitoring device.

The functional equipment systems or devices can also include any combination of hardware and/or software for allowing the personal monitoring device and any components or devices therein or associated therewith to be remotely accessed, controlled, and/or monitored, by or using any authorized user communication device used by an authorized user or individual, the or any central processing computer(s), the or any law enforcement communication device(s), the or any emergency services provider communication device(s), and/or the or any healthcare records computer(s). The personal monitoring device can also include an RFID tag which can be attached to, connected to, located on, or located within or inside a housing of, the personal monitoring device.

The central processing computer includes a central processing unit or CPU which can be a microprocessor or any other suitable processing device, microcomputer, a mini-computer, a macro-computer, and/or a mainframe computer, depending upon the application, a random access memory device(s) (RAM), a read only memory device(s) (ROM), a user input device, a display device, and a transmitter(s), for transmitting signals and/or data and/or information to any one or more of the personal monitoring device(s), the user communication device(s), the law enforcement communication device(s), the emergency services provider communication device(s), the healthcare records computer(s), the RFID reader system(s), the venue/vehicle computer(s), and/or any other central processing computer(s).

The central processing computer also includes a receiver(s) for receiving signals and/or data and/or information from any one or more of the personal monitoring device(s), the user communication device(s), the law enforcement communication device(s), the emergency services provider communication device(s), the healthcare records computer(s), the RFID reader system(s), the venue/vehicle computer(s), and/or any other central processing computer(s).

The central processing computer also includes a database(s) which can contain and/or include any and/or all of the data and/or information, and/or any software programs or software applications, needed or desired for or by the central processing computer to perform all of the operations, actions, functions, and/or functionality, described herein as being provided by, and/or as being performed by, the central processing computer and/or the apparatus of the present invention. The central processing computer can also include an output device(s), and a video and/or audio recording device(s).

The user communication device includes a central processing unit or CPU which can be a microprocessor or other suitable processing device, and/or can be microcomputer, a minicomputer, a macro-computer, and/or a mainframe computer. The user communication device can also include a random access memory device(s) (RAM), a read only memory device(s) (ROM), a user input device, a display device, and a transmitter(s) for transmitting signals and/or data and/or information to any one or more of the personal monitoring device(s), the central processing computer(s), the law enforcement communication device(s), the emergency services provider communication device(s), the healthcare records computer(s), the RFID reader system(s), the venue/vehicle computer(s), and/or any other user communication device(s).

The user communication device can also include a receiver(s) for receiving signals and/or data and/or information from any one or more of the personal monitoring device(s), the central processing computer(s), the law enforcement communication device(s), the emergency services provider communication device(s), the healthcare records computer(s), the RFID reader system(s), the venue/vehicle computer(s), and/or any other user communication device(s).

The user communication device can also include a database which can contain and/or can include any data and/or information, and/or any software programs or software applications, needed or desired for enabling and/or for allowing the user communication device to perform any and/or all of the functionality described herein which is capable of being performed by the user communication device and/or the apparatus of the present invention.

The user communication device can also include an output device(s) and a video and/or audio recording device(s). The user communication device can also include a "kill" switch or associated hardware and/or software for disabling and/or deactivating the user communication device in instances when same might be lost or stolen, so as to prevent its use by another person and/or to prevent any access to any data and/or information stored therein, thereby rendering the user communication device useless to another person after being reported, or being discovered, as being lost or stolen.

Each of the law enforcement communication device(s), the emergency services provider communication device(s), and the healthcare records computers, can also include a central processing unit or CPU, a random access memory device(s) (RAM), a read only memory device(s) (ROM), a user input device(s), a display device, a transmitter(s), a receiver(s), a database, an output device(s), and a video and/or audio recording device(s).

The RFID reader system can include any number of RFID readers which can service any single venue or any single vehicle, or the RFID reader system can include any number of RFID readers which can service any number of venues and/or any number of vehicles. The RFID reader system includes a central processing unit or CPU which can be a microprocessor or any other suitable processing device, and/or a microcomputer, a minicomputer, a macro-computer, and/or a mainframe computer.

The RFID reader system can also include a random access memory (RAM) device(s), a read only (ROM) memory device(s), a user input device(s), and a display device. The RFID reader system can also include a transmitter, for transmitting signals and/or data and/or information to any one or more of the personal monitoring device(s), the central processing computer(s), the user communication device(s), the law enforcement communication device(s), the emergency services provider communication device(s), and/or the venue/vehicle computer(s), or to any of the other RFID reader systems. The RFID reader system also includes a receiver, for receiving signals and/or data and/or information from any one or more of the personal monitoring device(s), the central processing computer(s), the user communication device(s), the law enforcement communication device(s), the emergency services provider communication device(s), and/or the venue/vehicle computer(s), or from any of the other RFID reader systems.

The RFID reader system can also include a database(s) which can contain and/or include any data and/or information, and/or any software programs or software applications, which may be required, and/or which may be desired, for performing any of the functionality and/or processing routines described herein as being performed by the RFID reader system and/or the apparatus of the present invention.

The RFID reader system also includes an output device(s) for outputting any of the data and/or information described herein as being generated by or via the RFID reader system, and a video and/or audio recording device(s), which can include a camera and/or a video recording device for recording pictures or video and/or video clips and/or a microphone or an audio recording device for recording audio or audio clips which can be recorded by, and/or transmitted live, by or from the RFID reader system, or which can be recorded by, and stored at or in, the RFID reader system for transmission by or from the RFID reader system at a later time. The RFID reader system can also include a global positioning device for determining the position or location of the RFID reader system.

The RFID reader system can also include an RFID reader, or any number of RFID readers which can be any commercially available RFID reader device which can be suitable for use with the kind or type of RFID reader system and RFID tags which are utilized in connection with the apparatus of the present invention. Any number of RFID readers can be utilized to service any single venue or any single vehicle. Each RFID reader can be stationed or positioned at, or adjacent to, a particular entrance, exit, door, doorway, and/or gateway, of, or any other entrance or exit means, of a respective vehicle or a respective vehicle, by or via which an individual, using a personal monitoring device, can enter and/or exit the respective venue or the respective vehicle.

The venue/vehicle computer includes a central processing unit or CPU which can be a microprocessor or other suitable processing device, or a microcomputer, a minicomputer, a macro-computer, and/or a mainframe computer. Each venue/vehicle computer can be associated with, assigned to, and/or deployed at, on, or in, any respective venue or any respective vehicle.

The venue/vehicle computer can also include a random access memory (RAM) device(s), a read only (ROM) memory device(s), a user input device(s), and a display device. The venue/vehicle computer can also include a transmitter, for transmitting signals and/or data and/or information to any one or more of the personal monitoring device(s), the central processing computer(s), the user communication device(s), the law enforcement communication device(s), the emergency services provider communication device(s), the healthcare records computers, and/or RFID reader systems, and/or to any other venue/vehicle computer(s), and a receiver, for receiving signals and/or data and/or information from any one or more of the personal monitoring device(s), the central processing computer(s), the user communication device(s), the law enforcement communication device(s), the emergency services provider communication device(s), the healthcare records computers, and/or the RFID reader systems, and/or to any other venue/vehicle computer(s).

The venue/vehicle computer also includes a database(s) which can contain and/or include any data and/or information, and/or any software programs and/or software applications, required or desired for performing all of the functions and/or functionalities described herein as being performed by the venue/vehicle computer and/or the apparatus of the present invention.

The venue/vehicle computer can also include an output device(s), a video and/or audio recording device(s), which can include a camera and/or a video recording device for recording pictures or video and/or video clips and/or a microphone or an audio recording device for recording audio or audio clips which can be recorded by, and/or transmitted live, by or from the venue/vehicle computer, or which can be recorded by, and stored at or in, the venue/vehicle computer for transmission by or from the venue/vehicle computer at a later time, and a global positioning device for determining the position or location of the venue/vehicle computer.

The venue/vehicle computer can also include one or more RFID readers which can be any commercially available RFID reader of RFID reader device(s) which can be suitable for use with the kind or type of venue or vehicle which is utilized, which can be suitable for the venue/vehicle computer which is utilized, and/or which can be suitable for the particular RFID reading functionality required at the respective venue or the respective vehicle. One or more RFID readers can be stationed at, or positioned at, a respective entrance, exit, door, doorway, gateway, or other means by which an individual using a personal monitoring device can enter and/or exit the respective venue or the respective vehicle. In this manner, the RFID reader(s) can read or scan a respective RFID tag(s) which are attached to or affixed to, or which are placed on or inside, the respective personal monitoring device being used by the individual as they enter and/or exit the respective venue or the respective vehicle. The RFID readers can be, or can include, any of the herein-described RFID readers of any of the herein-described RFID reader systems.

The apparatus and method of the present invention can be utilized to monitor an individual or individuals of any age. In this regard, the apparatus and/or the personal monitoring device can be utilized to monitor any child, infant, teenager or young adult, adult of any age, and/or elderly individual. The apparatus and/or the personal monitoring device can also be utilized to monitor any child, infant, teenager or young adult, adult of any age, and/or elderly individual, who may or may not be inflicted with a condition, illness, or disease, or who may or may not be inflicted with autism, Alzheimer's disease, memory loss, or be ill with any temporary or permanent illness, sickness, disease, or condition. The apparatus and/or the personal monitoring device can also be utilized to monitor any child, infant, teenager or young adult, adult of any age, and/or elderly individual, as a safety precaution.

Any user or individual who utilizes a personal monitoring device, or who has a personal monitoring device assigned to him or her, or who has a personal monitoring device associated with him or her, can be referred to herein, or can be defined herein as being, a "monitored individual". Any user or individual who utilizes a user communication device to monitor a monitored individual can be referred to herein, or can be defined herein as being, a "monitoring individual".

It is envisioned that a personal monitoring device can be programmed with, or can have stored therein or therewith, information regarding the monitored individual's home address, residence address, school residence address or place, workplace address, or other address, place, or location, which is considered to be that monitored individual's place of safety or "home base" or "safe location". It is also envisioned that the personal monitoring device can be programmed with, or can have stored therein or therewith, information regarding any address(es), place(s), or location(s), to which the monitored individual typically travels on a daily basis. For example, the personal monitoring device can be programmed with, or can have stored therein or therewith, information regarding the monitored individual's school address, place, or location, workplace address, place, or location, employment address, place, or location, activity or event address, place, or location, or any other address, place, or location, to which the monitored individual is known to travel on a weekday basis, on a weekend daily basis, or on any daily basis.

The personal monitoring device can also be programmed with the monitored individual's travel itineraries and/or travel schedules for traveling to and between one address, place, or location to another address, place, or location. The personal monitoring device can also be programmed with travel routes or directions for traveling to and between one address, place, or location to another address, place, or location. The personal monitoring device can also be programmed with software programs, navigation programs, or any algorithms or software applications, for identifying, determining, ascertaining, or calculating, any travel routes or directions for traveling to and between one address, place, or location to another address, place, or location.

The personal monitoring device can be utilized in connection with, or in conjunction with, the RFID tags in order to detect and/or to ascertain when the monitored individual enters into or onto, and/or exits from, any venue or any vehicle, and/or to detect and/or to ascertain when the monitored individual enters into or onto, and/or exits from, any venue or any vehicle during his or her daily activities and/or daily travels, regardless of whether or not the monitored individual is traveling in accordance with his or her travel itinerary or schedule.

The personal monitoring device can also be utilized in connection with, or in conjunction with, the apparatus, the central processing computer, a user communication device associated with, or used by, any user or individual authorized to, or assigned to, monitor the monitored individual, any law enforcement communication device, and/or any emergency services provider communication device. The personal monitoring device can also be utilized as a stand-alone device by the monitored individual to allow the monitored individual to monitor his or her travels, whereabouts, or environment.

The personal monitoring device can also be utilized to record, and/or to report on, the travels and/or travel history of or for a monitored individual for any given period of time. The personal monitoring device and/or the central processing computer can also utilize artificial intelligence (AI) and/or machine learning algorithms and/or programs in order to modify the stored or expected travel itinerary or schedule of a monitored individual.

The apparatus and method of the present invention can be utilized in order to monitor a monitored individual's entry into or onto, and/or exit from, a respective venue or a respective vehicle. In particular, the apparatus of the present invention can be utilized in order to detect and/or to ascertain, and/or to report and/or to provide notification, to an authorized user or to a monitoring individual, regarding when a monitored individual enters into or onto, and/or exits from, a venue, and/or enters into or onto, or exits from, a vehicle during the course of their daily activities and/or travels. The respective venue or vehicle can be equipped with an RFID reader(s) of a respective RFID reader system, or an RFID reader(s) of a respective venue/vehicle computer. An RFID reader or an RFID reader can be positioned at, or can be stationed at, a respective door, doorway, gate, or gateway, for each door, doorway, gate, or gateway, which serves as an entry point into, or exit point from, the respective venue or the respective vehicle.

Each time a monitored individual enters into or onto the respective venue or into or onto the respective vehicle, the RFID tag, of or associated with the monitored individual's personal monitoring device, can be read by the respective RFID reader or RFID reader which is positioned at the respective door, doorway, gate, or gateway, of the respective venue or the respective vehicle through which the monitored individual enters the same. The detection of the RFID tag can be reported, by and/or from the RFID reader system or the venue/vehicle computer, associated with the respective RFID reader or RFID reader associated with the respective venue/vehicle computer, to the central processing computer, to the user communication device, and/or to the personal monitoring device, via a transmission of an appropriate signal from the respective RFID reader system or the respective venue/vehicle computer to the central processing computer, to the user communication device, and/or to the personal monitoring device. Thereafter, the respective reader system or the respective venue/vehicle computer, and/or the central processing computer, can generate an entry notification message and/or an entry alert message which can contain and/or can include information identifying the monitoring individual, information regarding the date and time when the monitoring individual entered into or onto the respective venue or entered into or onto the respective vehicle, and/or information identifying the respective venue or the respective vehicle. The personal monitoring device can also generate the herein-described entry notification message and/or entry alert message.

In the case of the monitored individual entering into or onto a venue, the entry notification message and/or entry alert message can contain and/or can include information regarding the address of the venue and a contact individual and contact telephone number for the venue. In the case of the monitored individual entering into or onto a vehicle, the entry notification message and/or entry alert message can contain and/or can include information for identifying the vehicle, identifying the type of vehicle (such as, for example, a private car or vehicle, a car service vehicle, a ride-sharing vehicle (such as an Uber vehicle or a LYFT vehicle), a mass transportation vehicle, a bus, a train, a subway train, a boat of any type, kind or size, or an aircraft or helicopter of any type, kind, or size), and/or make and model information and/or vehicle identification information for the vehicle, information regarding the vehicle operator, and/or contact information for the vehicle and/or the vehicle operator and/or a telephone number for the vehicle owner or the vehicle operator. In the case of the monitored individual entering into or onto a vehicle, the entry notification message and/or entry alert message can also contain and/or can include information regarding the position or location of the vehicle at the time the monitored individual enters into to onto the vehicle. The position or location of the vehicle can be determined and/or ascertained by the global positioning device of the venue/vehicle computer associated with the respective venue or the respective vehicle.

The respective reader system or the respective venue/vehicle computer, and/or the central processing computer, can transmit the entry notification message and/or the entry alert message to the user communication device which is used by, associated with, or assigned to, the monitoring individual for the monitored individual. The monitoring individual can be a parent, a grandparent, a sibling, a relative, a friend, a guardian, or any other authorized person. In a situation where the monitored individual may be monitored by more than one monitoring individual, then the respective reader system or the respective venue/vehicle computer, and/or the central processing computer, can transmit the entry notification message and/or the entry alert message to the user communication device which is used by, associated with, or assigned to, each such monitoring individual. The respective reader system and/or the central processing computer can also transmit the entry notification message and/or the entry alert message to any law enforcement communication device(s) and/or to any emergency services provider communication device(s), if needed or desired. The personal monitoring device can transmit the entry notification message and/or the entry alert message to the user communication device(s) which is used by, associated with, or assigned to, the monitoring individual(s) for the monitored individual, and/or to any law enforcement communication device(s), and/or to any emergency services provider communication device(s), if needed or desired.

Any data and/or information contained in the entry notification message and/or the entry alert message can be stored in a travel log or travel history for the monitored individual, which travel log or travel history can be stored in any of the databases, of the respective devices, computers, or communications devices described herein.

The apparatus of the present invention can also utilize the RFID tags, the RFID reader systems, the RFID readers, the venue/vehicle computers, or RFID readers, and the global positioning device of the personal monitoring device, along with an individual's itinerary or schedule information, in order to monitor the location, movements, and/or whereabouts, of the individual. The apparatus of the present invention can also utilize the RFID tags, the RFID reader systems, the RFID readers, the venue/vehicle computers, or the RFID readers, along with an individual's itinerary or schedule information, in order to monitor the location, movements, and/or whereabouts, of the individual.

The apparatus of the present invention can also be utilized in a same, a similar, and/or an analogous, manner in order to monitor the movements and/or whereabouts of vehicles of all types or kinds, shipping containers and/or articles of luggage of all types, kinds, or sizes, and/or articles of any type or kind. In such an application, the personal monitoring device can be attached to, or located in, the respective vehicle, the respective shipping container or article of luggage, or the respective article, or the components of the personal monitoring device can be integrated with or within the respective vehicle, the respective shipping container or article of luggage, or the respective article.

DESCRIPTION OF THE PREFERRED EMBODIMENTS

Figure 1:
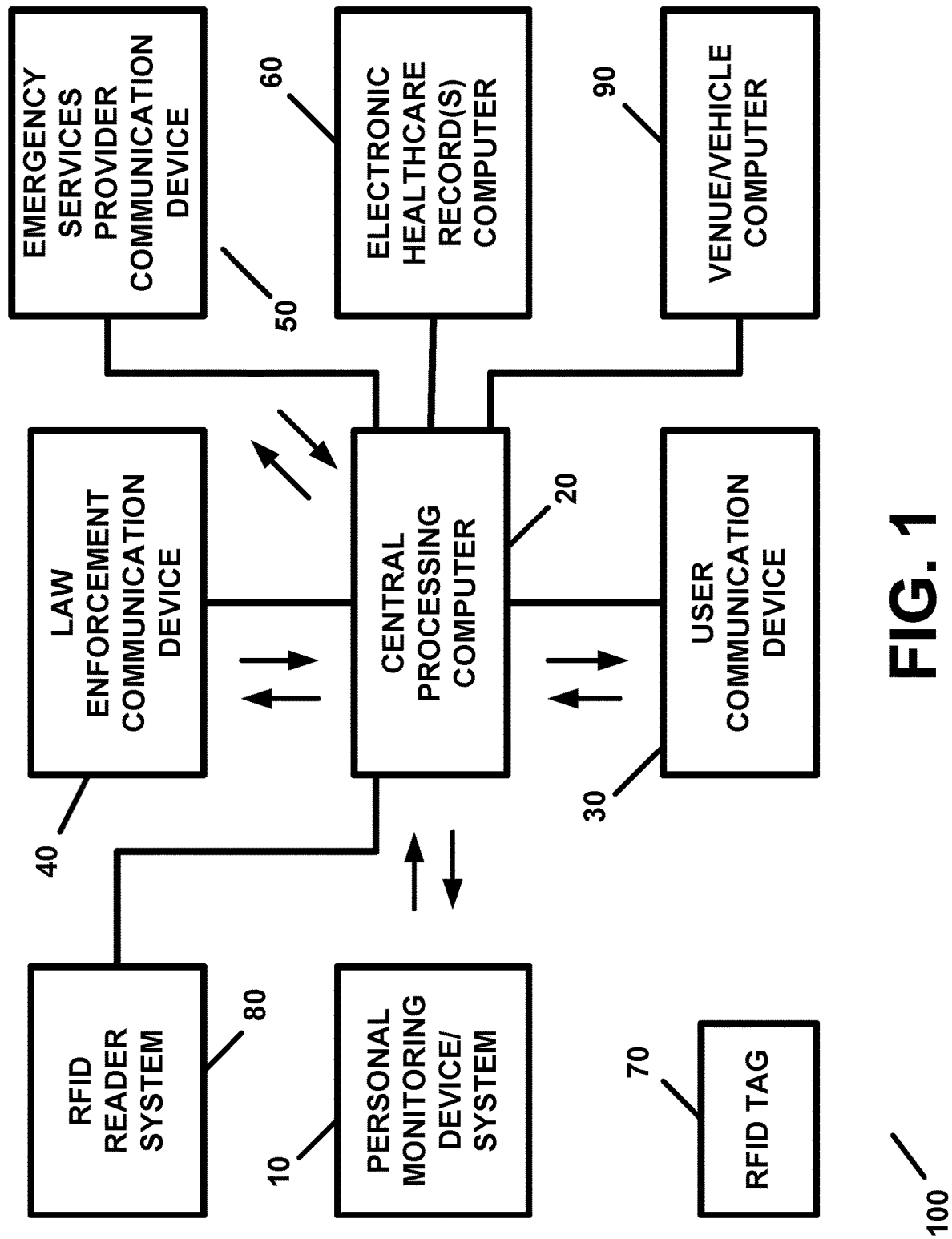
FIG. 1 illustrates the apparatus of the present invention, in block diagram form.

The present invention pertains to a personal monitoring apparatus and methods for individuals of all ages and, in particular, to a personal monitoring apparatus and methods for individuals of all ages which can be utilized to monitor infants, children, the elderly, or individuals of any and/or all ages, and/or to monitor their respective position or location utilizing RFID technologies and/or global positioning information in connection with expected itineraries and/or schedules. The present invention also pertains to a personal monitoring apparatus and methods and, in particular, to a personal monitoring apparatus and methods which can be utilized to monitor infants, children, the elderly, or individuals of any and/or all ages, and/or to monitor their position or location, their whereabouts, their surroundings, their vital signs, their physiological measurements, states, or condition, and/or any individual and/or individuals with whom they may come into contact.

The present invention can also provide an apparatus and methods which can be utilized to monitor and/or to track the whereabouts and/or the travels of an individual at any time, to compare an individual's current whereabouts to a location where they should be, ought to be, or are expected to be, and/or to provide an alert, or to provide a notification, to the individual, a parent of the individual, a child of the individual, a relative of the individual, a caregiver of the individual, an employer of the individual, a law enforcement agency or law enforcement personnel, emergency services personnel, a third party, or any other person or entity, when the individual is located at a location where they should not be, where they ought not be, where they are not expected to be, or when they have deviated from, or are deviating from, a planned, an expected, or a desired, travel route, or a planned, expected, or desired, itinerary or schedule.

For example, the apparatus and methods or the present invention can be used to monitor the whereabouts, the location, or the travel, of a child of any age, a child having special needs, a child who has become injured or ill, or a child who has become lost, missing, or who has become a victim of foul play. As and for another example, the apparatus and methods of the present invention can be used to monitor the whereabouts, the location, or the travel, of an adult or an elderly individual, of any age, an adult or an elderly individual having special needs, an adult or an elderly individual who has become ill or injured, or an adult or an elderly individual who has become lost, missing, or disoriented, or who has, or may have, become a victim of foul play.

The apparatus and methods of the present invention can also be utilized to provide information or an indication, to the individual, or to any person(s) with whom the individual may come into contact, which can provide information indicative of the individual being where he or she should not be, indicative that the individual is lost, indicative that the individual is or might be injured or ill, or indicative that the individual is disoriented, or in need of help or assistance.

The apparatus and methods of the present invention can also be utilized to provide information or an indication, to a parent of the individual, to a child of the individual, to a relative of the individual, to a caregiver of the individual, to an employer of the individual, to a law enforcement agency or law enforcement personnel, to an emergency services personnel, to any third party, or to any other person or entity, when the individual has been determined to be lost, injured, ill, disoriented, or otherwise in need of help or assistance.

The apparatus and methods of the present invention can also be utilized to obtain, record, store, and/or provide, healthcare information or physiological data and/or information, or any other information regarding the state or status of an individual, including, but not limited to, the individual's heart rate, blood pressure, body temperature, blood sugar level, or any other physical condition, physiological condition, or healthcare condition, which can be measured or can be measurable by any wearable device or by any implanted device or implantable device.

The apparatus and methods of the present invention can also be utilized to initiate, establish, and/or maintain, a communication link, or a telephone call, with and between any of the herein-described personal monitoring devices with any of the herein-described user communication devices, central processing computers, and/or law enforcement communication devices and/or emergency services communication devices. In this regard, for example, a line of communication can be established with and/or between the personal monitoring device of a lost, mission, or ill, child and a user communication device of, associated with, or used by, the child's parent, relative, caregiver, or other authorized person. The apparatus and methods of the present invention can also be utilized to provide an open, and/or speakerphone-operated, line of communication with the personal monitoring device so that a respective parent, relative, caregiver, or other authorized person can, using a user communication device, speak to, or engage in conversation with, the child or with any individual with whom the child comes into contact so as to facilitate finding the child, helping the child find help or his or her way back to a safe location, and/or making sure that the child is brought to a place of safety and/or is safely returned home or to another safe location, and/or to make sure that the child's needs are provided for until being reunited with his or her parent(s), a caregiver, or law enforcement. The apparatus and methods of the present invention can also be utilized in a same, a similar, or an analogous, manner in providing personal monitoring for adults and elderly individuals of any age.

The apparatus and methods of the present invention can also be utilized in order to establish, and to provide services for, personal monitoring accounts for individuals. In a preferred embodiment, a personal monitoring account can be assigned to an individual in order to provide any number or monitoring services for that individual. For example, a personal monitoring account can be utilized to allow any other authorized individual, person, or entity, to monitor, and/or to track location, position, or movement, of an individual, to communicate with the individual at any time, to communicate with people in the vicinity of the individual, to obtain information regarding the position, location, or whereabouts, of the individual, persons with whom the individual may be in contact with, or may have come into contact with, or the individual's itinerary, schedule, travels, and/or to obtain video and/or audio information regarding the individual, his or her travels, locations, and/or any other information regarding the individual. In a preferred embodiment, one or more personal monitoring accounts can be set up by or for an individual. In this regard, an individual can have one personal monitoring account ("PMA") or a plurality of personal monitoring accounts.

As will be described herein, the apparatus and methods of the present invention can be utilized to provide a number of various features and functionalities which can be useful in providing personal monitoring services and operations for infants, children, and adults, of any ages. The apparatus and methods of the present invention can also be utilized to provide personal monitoring services and operations for and regarding pets and animals of any type or kind.

Applicant hereby incorporates by reference herein the subject matter and teachings of U.S. Provisional Patent Application Ser. No. 62/880,608, filed Jul. 30, 2019, and entitled "PERSONAL MONITORING APPARATUS AND METHODS", the subject matter and teachings of which are hereby incorporated by reference herein in their entirety.

Applicant hereby incorporates by reference herein the subject matter and teachings of U.S. patent application Ser. No. 16/909,622, filed Jun. 23, 2020, and entitled "PERSONAL MONITORING APPARATUS AND METHODS", the subject matter and teachings of which are hereby incorporated by reference herein in their entirety.

FIG. 1 illustrates the apparatus of the present invention, in block diagram form. The apparatus of the present invention is denoted generally by the reference numeral 100. In the preferred embodiment, the apparatus 100 of the present invention includes a personal monitoring device 10. In the preferred embodiment, the personal monitoring device is, or can be, a cellular telephone, a mobile telephone or wireless telephone, a Smartphone, a personal digital assistant, or any other suitable device. In a preferred embodiment, the personal monitoring device 10 can also be any wearable device.

In a preferred embodiment, the personal monitoring device 10 can be equipped with the communication equipment typically found in cellular telephones, mobile telephones or wireless telephones, Smartphones, personal digital assistants, or any other suitable devices, for facilitating a two-way communication with other individuals or entities and/or with communications devices, computers, equipment, or any other communication equipment used by any individuals or entities described herein or otherwise. In a preferred embodiment, the personal monitoring device 10 can also be equipped with global positioning system (GPS) device or equipment. In another preferred embodiment, the personal monitoring device 10 can also be equipped with navigation equipment such as are typically found in commercially available GPS navigation devices and equipment which are used to assist motorists and individuals traveling in motor vehicles, on bicycles, or on foot, in navigating from a location to a destination. In a preferred embodiment, the personal monitoring device 10 can also be equipped with a radio-frequency identification ("RFID") tag or any number of RFID tags.

In a preferred embodiment, the personal monitoring device 10 can also be equipped with global positioning system (GPS) equipment and navigation equipment which can allow the personal monitoring device 10 to act in a stand-alone manner, without having to obtain any navigation information from any external device or computer. In another preferred embodiment, the personal monitoring device 10 can be equipped to receive, and provide to a user, navigation data and/or information, including, but not limited to, navigation instructions, which is obtained from an external computer or communication device or a service provider computer or communication device.

The personal monitoring device 10 can also be any communication device, computer, personal computer, laptop computer, notebook computer, Smartphone or smartphone, smart telephone, cellular telephone, personal digital assistant, tablet, tablet computer, watch, smart watch, or wearable device or computer, an implantable device or computer, an item of jewelry, eyeglasses, or any accessory, or any combination of same, or any equivalent of same, which can be utilized by any person, individual, or entity, who or which utilizes the apparatus 100 and methods of the present invention. The personal monitoring device 10 can also be a server computer, a mainframe computer, a mini-computer, a microcomputer, or any other computer or device for suiting the needs of the particular user.

Any number of personal monitoring devices 10 can be utilized by or in conjunction with the apparatus 100 of the present invention. The personal monitoring device 10 can communicate, in a bi-directional manner and/or otherwise, with and/or can operate in conjunction with any of the computers, communication devices, and/or computer systems, described herein as being utilized in connection with the apparatus 100 and methods of the present invention.

In the preferred embodiment, the apparatus 100 of the present invention also includes a central processing computer or central processing computer system 20 (hereinafter referred to as the "central processing computer 20"). In the preferred embodiment the central processing computer 20 can be any computer or computer system or can be any computer which can be operated in a network environment with other computers or a server computer.

In the preferred embodiment, the central processing computer 20 can provide control over the apparatus 100 and can perform any of the various processing services, routines, and/or functions, described herein as being performed by the same. The central processing computer 20 can be a single computer or a system of computers and/or can include a plurality of computers or computer systems which are utilized in conjunction with one another. The central processing computer 20, in the preferred embodiment, can provide personal monitoring services for or regarding any number of individuals and/or entities and/or can provide personal monitoring services for or regarding any number of individuals and/or entities who or which need, want, or desire, to monitor, to monitor the whereabouts of, and/or who or which desire to be notified regarding the whereabouts, location, healthcare status, or any occurrence of or regarding any event which may give rise to a need to find, locate, and/or monitor, a location of any child, adult, elderly person, or any individual of any age.

Any number of central processing computers 20 can be utilized by or in conjunction with the apparatus 100 of the present invention. The central processing computer(s) 20 can communicate, in a bi-directional manner and/or otherwise, with, and/or can operate in conjunction with, the personal monitoring device 10 and/or any of the other communication devices, computers, and/or computer systems, associated with or used by any of the individuals and/or entities who or which utilize the apparatus 100 and methods of the present invention.

The apparatus 100 also includes a user communication device or computer 30 (hereinafter referred to as "user communication device 30" or "user computer 30") which is associated with, or which can be used by, any one or more of any of the herein-described users, individuals, or entities, who or which utilize the apparatus 100 and methods of the present invention.

Any number of user communication devices 30 can be utilized by or in conjunction with any user or any individual or entity who or which utilizes the apparatus 100 and methods of the present invention, and any number of user communication devices 30 can be utilized in conjunction with the apparatus 100 and methods of the present invention.

The user communication device(s) 30 can communicate, in a bi-directional manner and/or otherwise, with, and/or can operate in conjunction with the personal monitoring device 10 and/or the central processing computer 20 and/or any of the other herein-described communication devices, computers, and/or computer systems, associated with or used by any of the individuals and/or entities who or which utilize the apparatus 100 and methods of the present invention.

The apparatus 100 also includes a law enforcement communication device or computer 40 (hereinafter referred to as "law enforcement communication device 40" or "law enforcement computer 40") which is associated with, or which can be used by, any law enforcement agency or department which utilizes the apparatus 100 and methods of the present invention.

Any number of law enforcement communication devices 40 can be utilized by or in conjunction with any law enforcement agency or department which utilizes the apparatus 100 and methods of the present invention, and any number of law enforcement communication devices 40 can be utilized in conjunction with the apparatus 100 and methods of the present invention.

The law enforcement communication device(s) 40 can communicate, in a bi-directional manner and/or otherwise, with, and/or can operate in conjunction with the personal monitoring device 10, the central processing computer 20, the user communication device 30, and/or any of the other herein-described communication devices, computers, and/or computer systems, associated with or used by any of the individuals and/or entities who or which utilize the apparatus 100 and methods of the present invention.

The apparatus 100 also includes an emergency services provider communication device or computer 50 (hereinafter referred to as an "emergency services provider communication device 50" or "emergency services provider computer 50") which is associated with, or which can be used by, any emergency services provider, agency, or department, which utilizes the apparatus 100 and methods of the present invention.

Any number of emergency services provider communication devices 50 can be utilized by or in conjunction with any emergency services provider, agency, or department, which utilizes the apparatus 100 and methods of the present invention, and any number of emergency services provider communication devices 50 can be utilized in conjunction with the apparatus 100 and methods of the present invention.

The emergency services provider communication device(s) 50 can communicate, in a bi-directional manner and/or otherwise, with, and/or can operate in conjunction with the personal monitoring device 10, the central processing computer 20, the user communication device 30, the law enforcement communication device 40, and/or any of the other herein-described communication devices, computers, and/or computer systems, associated with or used by any of the individuals and/or entities who or which utilize the apparatus 100 and methods of the present invention.

The apparatus 100 can also include a healthcare records computer or communication device 60 (hereinafter referred to as "healthcare records computer 60") which, in a preferred embodiment, stores an electronic healthcare record or electronic healthcare records for any of the herein-described individuals who or which can be monitored using the apparatus 100 and methods of the present invention. In a preferred embodiment, the healthcare records computer can also store healthcare records of any individual, children, adults, elderly persons, or any individual of any age, who is to be monitored by and using the apparatus 100 and methods of the present invention as well as any healthcare records of, for, or regarding, any relatives of any of these individuals.

In a preferred embodiment, the healthcare records computer 60 or computers can serve to store and house an electronic healthcare record or any number of electronic healthcare records. The healthcare records computer 60 can also be utilized to facilitate cloud storage of any electronic healthcare record(s).

The healthcare records computer(s) 60 can communicate, in a bi-directional manner and/or otherwise, with, and/or can operate in conjunction with, the personal monitoring device the central processing computer 20, the user communication device 30, the law enforcement communication device 40, the emergency services provider communication device 50, and/or any of the other communication devices, computers, and/or computer systems, associated with or used by any of the individuals and/or entities who or which utilize and/or operate in conjunction with the apparatus 100 of the present invention.

With reference once again to FIG. 1, the apparatus 100 also includes any number of radio frequency identification (RFID) tags 70 (hereinafter referred to as "RFID tag 70" or "RFID tags 70"). In a preferred embodiment, an RFID tag 70 can be attached to, affixed to, or placed on or in, a personal monitoring device 10. In another preferred embodiment, the RFID tag 70 can be worn by the individual or attached to an article of clothing worn by the individual. In a preferred embodiment, the RFID tags 70 can be of any suitable type or kind, and can be selected from among the various types or kinds of RFID tags which are available in the marketplace as of the filing date of this patent application. In a preferred embodiment, the RFID tags 70 can be passive RFID tags, while in other preferred embodiments any one or more of the RFID tags 70 can be active RFID tags. In a preferred embodiment, the RFID tags 70 should be waterproof, washable, and/or otherwise be capable of being cleaned, and they should be temperature resistant and durable, in order to be utilized in all types or kinds of environments, in all types or kinds of weather conditions, and/or in order to be utilized in conjunction with all types and/or kinds of clothing or apparel, shoes, boots, hats, gloves, accessories, and other wearable objects and/or articles. In a preferred embodiment, any type or kind of RFID tag 70 can be utilized in connection with the apparatus 100 of the present invention provided that the respective RFID tag is suitable for use in its particular application.

Any number of RFID tags 70 can be utilized in connection with the apparatus 100 of the present invention. Further, in a preferred embodiment, passive RFID tags can be utilized in any situation where a respective tag may not be capable of having its own power source. In embodiments where RFID tags can be provided with a power source, then active RFID tags can be used. For example, if an RFID tag 70 can be powered by a power source of the personal monitoring device 10, then the RFID tag 70 can be an active RFID tag. In a preferred embodiment, passive RFID tags can provide for the most convenient use since they do not have or require a power source, but rather, they can be energized and operate when activated by a suitable RFID reader device.

With reference once again to FIG. 1, the apparatus 100 also includes any number of RFID reader systems 80 which can be, or which can include, any suitable RFID reader. In a preferred embodiment, each RFID reader system 80 can be reader for passive RFID tags or can be a reader for active RFID tags depending upon the application. In a preferred embodiment, each RFID reader system 80 can be utilized to read any of the RFID tags 80 described herein as being utilized in connection with the apparatus 100 of the present invention. In a preferred embodiment, the RFID reader system 80 can include any number of RFID readers which can service any single venue or any single vehicle, or the RFID reader system 80 can include any number of RFID readers which can service any number of venues and/or any number of vehicles.

The RFID reader system 80 can communicate with and/or can interact with any of the personal monitoring devices 10, the central processing computers 20, the user communication devices 30, the law enforcement communication devices 40, the emergency services provider communication devices 50, the healthcare records computers 60, and/or any of the other communication devices, computers, and/or computer systems, described herein and/or associated with, or used by, any of the individuals and/or entities who or which utilize and/or operate in conjunction with the apparatus 100 of the present invention. In the preferred embodiment, the RFID reader system 80 can communicate with, and/or be linked with, any of the personal monitoring devices 10, the central processing computers 20, the user communication devices 30, the law enforcement communication devices 40, the emergency services provider communication devices 50, the healthcare records computers 60, and/or any of the other communication devices, computers, and/or computer systems, described herein, via a wired communication network, a wireless communication network, or via any combination of wired and/or wireless communication networks.

With reference once again to FIG. 1, the apparatus 100 can also include any number of venue computers 90 or vehicle computers 90 (hereinafter referred to as "venue/vehicle computer 90"), with each venue/vehicle computer 90 being assigned to a respective venue, which can be any premises or building, school, place of work, or other physical location, and/or which can be the site of social events, entertainment events, sporting events, or any other events or gatherings, as well as which can be any type or kind of place of business, educational institution, or other public venue, or being assigned to respective vehicle, which can be any land, sea, or air, vehicle, which can be any automobile of motor vehicle, train, subway train, bus, or other mass transportation vehicle, or any boat, ship, submarine, or any marine vehicle, or any airplane, jet, helicopter, ort any other air vehicle, and/or which be any space vehicle, and/or any vehicle or entity in which an individual can travel from one location to another.

In a preferred embodiment, venues can also include, but not be limited to stores, places of business, malls, shopping malls, public gathering places, private gathering places, restaurants, cafes, stadiums, arenas, and/or any other place where people can gather for an event or participate in any activity or activities, and/or any other place or location where the apparatus 100 of the present invention can be utilized.

In a preferred embodiment, each venue/vehicle computer 90 can include, can be equipped with, or can have assigned thereto, an RFID reader or RFID reader systems 80, or any number of RFID readers or RFID reader systems 80. In a preferred embodiment, each venue/vehicle computer 90 should be equipped with one or more RFID reader or RFID reader systems 80 for reading any of the RFID tags 70 which can enter the respective venue or vehicle, and/or which can leave the respective venue or vehicle with which the venue/vehicle computer is associated.

The venue/vehicle computer 90 can communicate with and/or interact with any of the personal monitoring devices 10, the central processing computers 20, the user communication devices 30, the law enforcement communication devices 40, the emergency services provider communication devices 50, the healthcare records computers 60, the RFID reader systems 80, and/or any of the other communication devices, computers, and/or computer systems, described herein and/or associated with, or used by, any of the individuals and/or entities who or which utilize and/or operate in conjunction with the apparatus 100 of the present invention. In the preferred embodiment, the venue/vehicle computer 90 can communicate with, and/or be linked with, any of the personal monitoring devices 10, the central processing computers 20, the user communication devices 30, the law enforcement communication devices 40, the emergency services provider communication devices 50, the healthcare records computers 60, the RFID reader systems 80, and/or any of the other communication devices, computers, and/or computer systems, described herein. In the preferred embodiment, the venue/vehicle computer 90 can communicate with, and/or be linked with, any of the personal monitoring devices 10, the central processing computers 20, the user communication devices 30, the law enforcement communication devices 40, the emergency services provider communication devices 50, and/or any of the other communication devices, computers, and/or computer systems, described herein, via a wired communication network, a wireless communication network, or via any combination of wired and/or wireless communication networks.

The venue/vehicle computer 90 can be associated with, can utilized at, and/or can be used by any authorized person at, the respective venue or vehicle in order to interface with, and/or interact with, the central processing computer 20 or with any other computers and communication devices described herein as being used in or with the apparatus 100. In a preferred embodiment, each venue/vehicle computer 90 can include any number of computers, server computers, or computer systems.

In a preferred embodiment, each of the herein-described central processing computers 20, law enforcement communication devices 40, emergency services provider communication devices 50, healthcare records computers 60, RFID reader systems 80, and/or venue/vehicle computer 90, can also have a website or websites associated therewith.

In the preferred embodiment, any of the personal monitoring device(s) 10, the central processing computer(s) 20, the user communication device(s) 30, the law enforcement communication device(s) 40, the emergency services provider communication device(s) 50, the healthcare records computer(s) 60, the RFID reader systems 80, and/or the venue/vehicle computer 90, can be any computer or communication device, including, but not limited to, a personal computer, a home computer, a server computer, or any computer capable of being utilized in a network or capable of being utilized with other computers in a network, or a hand-held computer, a palmtop computer, a laptop computer, a personal communication device, a cellular telephone, a wireless telephone, a mobile telephone, a digital television, an interactive television, a digital television, a personal digital assistant, a telephone, a digital telephone, a television, an interactive television, a beeper, a pager, and/or a watch or a Smart watch, and/or any wearable device, computer or communication device.

Each of the personal monitoring device(s) 10, the central processing computer(s) 20, the user communication device(s) 30, the law enforcement communication device(s) 40, the emergency services provider communication device(s) 50, the healthcare records computer(s) 60, the RFID reader systems 80, and/or the venue/vehicle computers 90, can transmit information to, as well as receive information from, any of the computers or communication devices 10, 20, 30, 40, 50, 60, 80, and/or 90 described herein. In this regard, each of the computers or communication devices 10, 20, 30, 40, 50, 60, 80, and/or 90, can communicate with, process information from, and/or share data and/or information with, each other and/or any other computer(s) or communication device(s) 10, 20, 30, 40, 50, 60, 80, and/or 90, described herein and/or utilized in conjunction with the apparatus 100 of the present invention. In this manner, any of the respective computer(s) or communication device(s) 10, 20, 30, 40, 50, 60, 80, and/or 90, can communicate with any other computer(s) or communication device(s) 10, 20, 30, 40, 50, 60, 80, and/or 90, in a bi-directional manner.

In the preferred embodiment, the present invention can be utilized on, over, and/or via, the Internet and/or the World Wide Web, and/or on, over, and/or via, any other communication network, and/or on, over, and/or via, any wireless communication network and/or any cellular communication network. The present invention, in the preferred embodiment, can also utilize wireless Internet and/or World Wide Web services, equipment and/or devices. In a preferred embodiment, the central processing computer(s) 20, in the preferred embodiment, has a web site or web sites associated therewith. Each of the other computers or communication devices described herein can also have a web site or web sites associated with same.

Although the Internet and/or the World Wide Web is a preferred communication system and/or medium utilized, the present invention, in any and/or all of the embodiments described herein, can also be utilized with any appropriate communication network or system including, but not limited to, a telecommunication network or system, a telephone communication network or system, a cellular communication network or system, a wireless communication network or system, a line or wired communication network or system, a wireless Internet network or system, a wireless World Wide Web network or system, a digital communication network or system, a personal communication network or system, a personal communication services (PCS) network or system, a satellite communication network or system, a broad band communication network or system, a low earth orbiting (LEO) satellite network or system, a public switched telephone network or system, a telephone communication network or system, a radio communication network or system, a cable television network or system, and/or any other communication network or system, and/or any combination of the above communication networks or systems.

Any of the personal monitoring device(s) 10, the central processing computer(s) 20, the user communication device(s) 30, the law enforcement communication device(s) 40, the emergency services provider communication device(s) 50, the healthcare records computer(s) 60, the RFID reader systems 80, and/or the venue/vehicle computers 90, can communicate with one another, and/or be linked to one another, over or via any communication network, telecommunication network, telephone network, a line-connected network, and/or a wireless communication network, and/or the Internet and/or the World Wide Web. Each of the computers or communication devices 10, 20, 30, 40, 50, 80, 80, and/or 90, can be linked with any other computers or communication devices directly or indirectly with one another so as to facilitate a direct or indirect bi-directional communication between said respective computers or communication devices. Communications between each of the computers or communication devices 10, 20, 30, 40, 50, 60, 80, and/or 90, can also involve an e-mail server or e-mail servers in those instances when e-mails are described as being used to transmit or to send any of the information, signals, messages, reports, notification messages, or any other communications, described herein, by or between any of the computers or communication devices 10, 20, 30, 40, 50, 60, 80, and/or 90, or when any of the information, signals, messages, reports, notification messages, or any other computers or communications, described herein, are transmitted by and/or between any of the parties described herein and/or by or between any of the computers or communication devices 10, 20, 30, 40, 50, 60, 80, and/or 90, or any other computers or communication devices, computer systems, communication network equipment, server computers, etc., or any other devices used or needed, in order to facilitate communications or the transmission of any of the herein-described information, signals, messages, reports, notification messages, or any other communications.

In a preferred embodiment, each of the personal monitoring device(s) 10, the central processing computer(s) 20, the user communication device(s) 30, the law enforcement communication device(s) 40, the emergency services provider communication device(s) 50, the healthcare records computer(s) 60, the RFID reader systems 80, and/or the venue/vehicle computers 90, can communicate in a bi-directional manner with, and/or can send and/or receive signals, data, information, messages, reports, notification messages, alerts, or any other communications or electronic communication transmissions, to, from and/or between, any other, or any number of, other personal monitoring device(s) 10, central processing computer(s) 20, user communication device(s) 30, law enforcement communication device(s) 40, emergency services provider communication device(s) 50, healthcare records computer(s) 60, RFID reader systems 80, and/or venue/vehicle computers 90.

In a preferred embodiment, each of the personal monitoring device(s) 10, the central processing computer(s) 20, the user communication device(s) 30, the law enforcement communication device(s) 40, the emergency services provider communication device(s) 50, the healthcare records computer(s) 60, the RFID reader systems 80, and/or the venue/vehicle computers 90, can be linked to or with any other personal monitoring device(s) 10, central processing computer(s) 20, user communication device(s) 30, law enforcement communication device(s) 40, emergency services provider communication device(s) 50, healthcare records computer(s) 60, RFID reader systems 80, and/or venue/vehicle computers 90, via a wired link or line or a wireless link.

In a preferred embodiment, each of the personal monitoring device(s) 10, the central processing computer(s) 20, the user communication device(s) 30, the law enforcement communication device(s) 40, the emergency services provider communication device(s) 50, the healthcare records computer(s) 60, the RFID reader systems 80, and/or the venue/vehicle computers 90, can be connected with, or linked to or with, the central processing computer(s) 20 as shown in FIG. 1.

In a preferred embodiment, any and/or all of the signals, data, information, messages, reports, notification messages, or any other communications, described herein as being transmitted from one device, computer, or communication device, to another device, computer, or communication device, can be, or can be included in, or can be attached to, an e-mail message, an instant messaging message, an electronic transmission, or an electronic data transmission or electronic data interchange, or can be transmitted via any other data or information transmission, and/or can be transmitted via or using any appropriate or necessary computer(s) or device(s).

In the preferred embodiment, each of the personal monitoring device(s) 10, the central processing computer(s) 20, the user communication device(s) 30, the law enforcement communication device(s) 40, the emergency services provider communication device(s) 50, the healthcare records computer(s) 60, the RFID reader systems 80, and/or the venue/vehicle computers 90, can transmit data and/or information using TCP/IP, as well as any other Internet and/or World Wide Web, and/or communication, protocols.

The apparatus 100 of the present invention can utilize electronic commerce technologies and security methods, techniques and technologies, including any encryption or security technologies and/or techniques, in any and/or all of the instances of data and/or information processing, and/or data and/or information transmission described herein.

Figure 2:
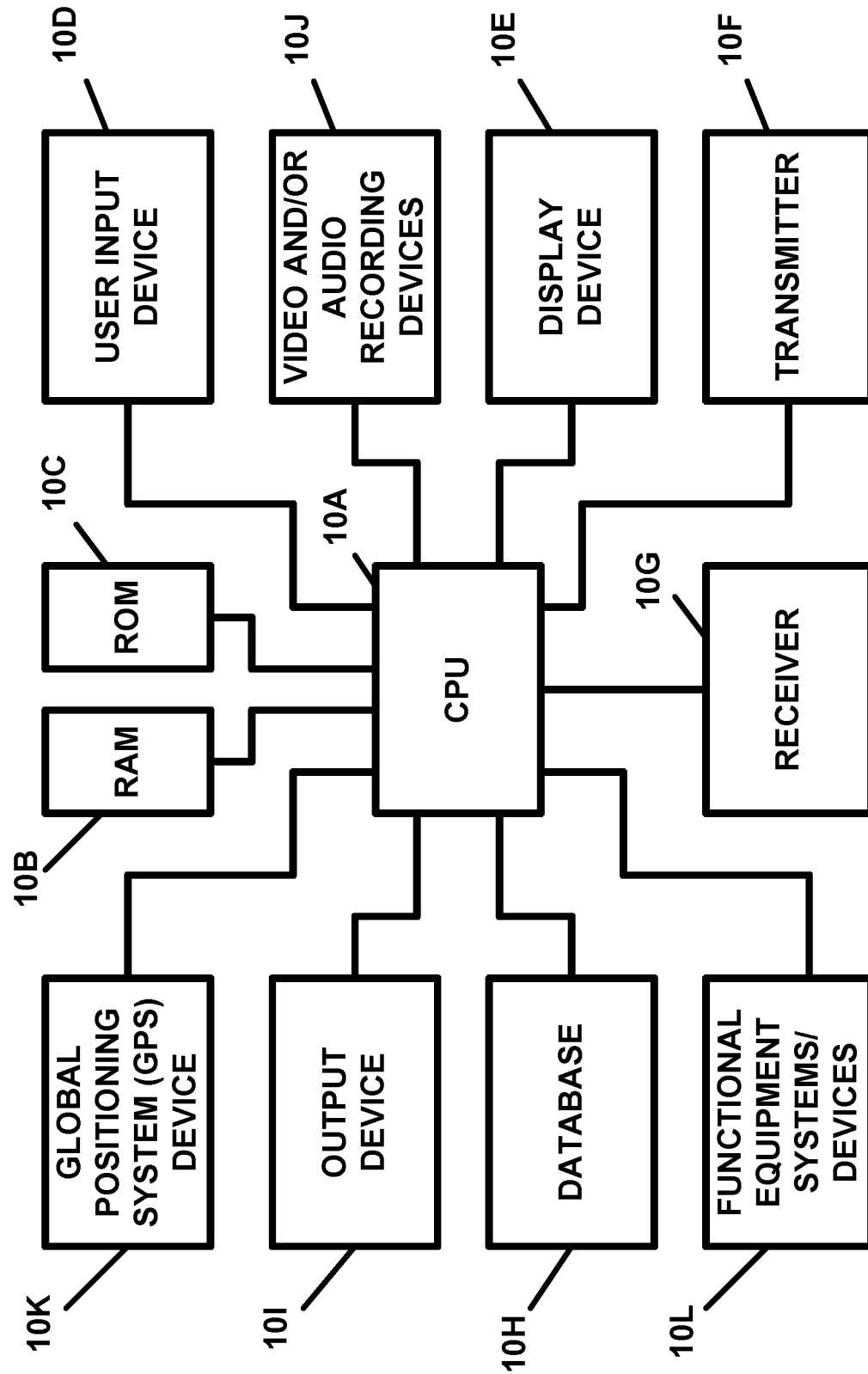
FIG. 2 illustrates the personal monitoring device of FIG. 1, in block diagram form.

FIG. 2 illustrates the personal monitoring device 10 of FIG. 1, in block diagram form. In a preferred embodiment, the personal monitoring device 10 can be a cellular telephone, a wireless telephone, a mobile telephone, a Smartphone, a smartphone, or a personal digital assistant, or the personal monitoring device 10 can be or can be a component of a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The personal monitoring device 10 can also be a server computer, or any computer capable of being utilized in a network or capable of being utilized with other computers in a network.

The personal monitoring device 10 can also be any communication device, computer, personal computer, laptop computer, notebook computer, Smartphone or smartphone, smart telephone, cellular telephone, personal digital assistant, tablet, tablet computer, watch, smart watch, or wearable device or computer, an implantable device or computer, an item of jewelry, eyeglasses, or any accessory, or any combination of same, or any equivalent of same.

With reference to FIG. 2, in the preferred embodiment, the personal monitoring device 10 includes a central processing unit or CPU 10A, which in the preferred embodiment, is a microprocessor. The CPU 10A can also be a microcomputer, a minicomputer, a macro-computer, and/or a mainframe computer, depending upon the application.

The personal monitoring device 10 also includes a random access memory device(s) 10B (RAM), a read only memory device(s) 10C (ROM), each of which is connected to, or linked with, the CPU 10A, and a user input device 10D, for inputting and/or entering data and/or information and/or instructions and/or commands into the personal monitoring device 10, which can include any one or more of a keyboard, a scanner, a user pointing device, such as, for example, a mouse, a stylus, a touch pad, and/or an audio input device, a microphone, an audio recording device, and/or a video input device, a camera or any number of cameras, a video recording device, and/or any device, electronic and/or otherwise, which can be utilized for inputting and/or entering data and/or information and/or instructions and/or commands into the personal monitoring device 10.

The input device(s) 10D is/are also connected to, or linked with, the CPU 10A. In a preferred embodiment, the input device(s) 10D can also be or can include a pulse rate monitor or measurement device or equipment, a heart rate monitor of measurement device or equipment, a blood sugar monitor or measurement device or equipment, a blood pressure monitor or measurement device or equipment, a blood alcohol monitor or measurement device or equipment, a pacemaker, a defibrillator, a thermometer for measuring an individual's body temperature, or any other device, monitor, or measurement, device or equipment, and/or any electrical or bio-medical device or equipment, which can measure an individual's physical condition, health condition, health status, healthcare condition, or physiological condition or status, or any other biological or biometric data and/or information.

In a preferred embodiment, any of the herein-described pulse rate monitors or measurement devices or equipment, heart rate monitors of measurement devices or equipment, blood sugar monitors or measurement devices or equipment, blood pressure monitors or measurement devices or equipment, blood alcohol monitors or measurement devices or equipment, pacemakers, defibrillators, thermometers, or any other devices, monitors, or measurement devices or equipment, and/or any electrical or bio-medical devices or equipment, can be wirelessly linked with and/or to the CPU 10A and/or to the personal monitoring device 10 and can be wearable, attachable to clothing, or implantable. In a preferred embodiment, the input device(s) 10D can also include a thermometer for measuring the temperature on the exterior of the personal monitoring device 10.

In preferred embodiment, any of the input device(s) 10D described or identified herein can be either connected to, or linked with, or with the CPU 10A directly or indirectly, and/or or can be wirelessly linked to or with the personal monitoring device 10, the CPU 10A, or any other component of the personal monitoring device 10 with or using a Bluetooth device or system and/or any suitable wireless device or wireless linking device or wireless linking system.

The personal monitoring device 10 can also include a display device 10E for displaying data and/or information to a user or operator. In the preferred embodiment, the display device 10E is also connected to, or linked with, the CPU 10A. The personal monitoring device 10 also includes a transmitter(s) 10F, for transmitting signals and/or data and/or information to any one or more of the central processing computer(s) 20, the user communication device(s) 30, the law enforcement communication device(s) 40, the emergency services provider communication device(s) 50, the healthcare records computer(s) 60, the RFID reader system(s) 80, the venue/vehicle computer(s) 90, and/or any other personal monitoring device(s) 10, which can be utilized in conjunction with the present invention. In the preferred embodiment, the transmitter(s) 10F is/are also connected to, or linked with, the CPU 10A. The personal monitoring device 10 also includes a receiver(s) 10G, for receiving signals and/or data and/or information from any one or more of the central processing computer(s) 20, the user communication device(s) 30, the law enforcement communication device(s) 40, the emergency services provider communication device(s) 50, the healthcare records computer(s) 60, the RFID reader system(s) 80, the venue/vehicle computer(s) 90, and/or any other personal monitoring device(s) 10, which can be utilized in conjunction with the present invention. In the preferred embodiment, the receiver(s) 10G is/are also connected to, or linked with, the CPU 10A.

The personal monitoring device 10 also includes a database(s) 10H. In the preferred embodiment, the database(s) 10H is/are also connected to, or linked with, the CPU 10A. The database(s) 10H can contain and/or can be linked to any of the data and/or information described herein as being stored in the respective database(s) of any of the central processing computer(s) 20, the user communication device(s) 30, the law enforcement communication device(s) 40, the emergency services provider communication device(s) 50, the healthcare records computer(s) 60, the RFID reader system(s) 80, and/or the venue/vehicle computer(s) 90, described herein.

In a preferred embodiment, the database 10H can contain and/or can include any data and/or information, and/or any link or links to any data and/or information, needed or desired for enabling and/or for allowing the personal monitoring device 10 and/or the apparatus 100 and/or any of the computers or communication devices described herein as being utilized in conjunction with the apparatus 100 and method of the present invention to perform any and/or all of the functionality described herein which is capable of being performed by the personal monitoring device 10 and/or the apparatus 100 of the present invention.

In a preferred embodiment, the database 10H can contain and/or can include any software, software programs, algorithms, or software applications ("apps") needed or desired for enabling and/or for allowing the personal monitoring device 10 and/or the apparatus 100 and/or any of the computers or communication devices described herein as being utilized in conjunction with the apparatus 100 and method of the present invention to perform any and/or all of the functionality described herein which is capable of being performed by the personal monitoring device 10 and/or the apparatus 100 of the present invention.

In a preferred embodiment, the database(s) 10H can contain and/or can include any data and/or information regarding the user or the individual, or any users or individuals, who or which utilize the personal monitoring device 10. Any data and/or information regarding the user or individual who is using the personal monitoring device 10 to be monitored, can include, but is not limited to, the user's or the individual's name, address, home telephone number, e-mail address, IP address, test messaging number, text messaging address, cellular telephone number, the telephone number assigned to the personal monitoring device 10, date or birth, gender, height, weight, identification photograph, social security number or any other suitable identification information, and/or any other data and/or information regarding the user of the individual.

The database 10H can also contain and/or can include any data and/or information regarding the user's or the individual's personal monitoring device 10 which can include, but which is not limited to, the type of device, such as for example, a cellular telephone, Smartphone, smartphone, personal digital assistant, or any other device described herein which can be utilized as a personal monitoring device 10, the manufacturing and model number of personal communication device 10, a serial number of the personal monitoring device 10, any other identifying data and/or information assigned to, associated with, or relating to, the personal monitoring device 10, the telephone number associated with, or assigned to, the personal communication device 10, the cellular telephone number associated with, or assigned to, the personal communication device 10, the wireless or mobile telephone number associated with, or assigned to, the personal communication device 10, an IP address associated with, or assigned to, the personal monitoring device 10, an email address associated with, or assigned to the personal monitoring device 10, a text messaging number associated with, or assigned to, the personal monitoring device 10, and/or any other data and/or information associated with the personal monitoring device 10. The database 10H can also contain and/or can include any of the above-described information for any other personal monitoring device 10 or any number of personal monitoring devices 10 which is/are used by the user or individual.

The database 10H can also contain and/or can include any data and/or information regarding a person who is monitoring the user or the individual. In a preferred embodiment, the a person who is monitoring the user or the individual can be, but is not limited to, the user's or individual's parent or parents, spouse, sibling, relative, friend, nanny, au pair, caregiver, teacher, employer, or any other person or entity, who or which is monitoring the user or individual (hereafter also referred to as "monitoring person"). For each monitoring person and, therefore, for each respective parent, spouse, sibling, relative, friend, nanny, au pair, caregiver, teacher, employer, or any other person or entity, who monitors the user of the individual or of or for the user or individual, the database 10H can contain and/or can include any data and/or information regarding the name, address, telephone number, cellular telephone number, user communication device telephone number or cellular telephone number, e-mail address, text messaging number, and/or any other data and/or information, and/or contact information, of, for, or regarding, the monitoring person. The database 10H can also contain and/or can include any other data and/or information, described herein as being stored for or regarding the user or individual, for or regarding the monitoring person.

The database 10H can also contain and/or can include any data and/or information regarding places, locations, or venues, to which the user or individual travels. The database 10H can also contain and/or can include any data and/or information regarding the daily schedule or daily schedules of or for the user or the individual, and/or any data and/or information regarding the daily routine or daily routines of or for the user or individual, any places where the user or individual is or has to be at a given time, and/or any other data and/or information regarding the user's or the individual's daily routines, weekly routines, travel routines, travel routes used, alternate travel routes used, travel times and/or time of travel regarding any travel by the user or individual, and/or any other data and/or information regarding the user's or the individual's routines that can be utilized in performing a personal monitoring service for or regarding the user or the individual.

For example, in the case of a child being monitored, the database 10H can contain and/or can include any data and/or information regarding the daily weekday schedule for the child such as, for example, the child's home address, the time or approximate time when the child leaves home for school, a preferred travel route the child takes to go to school, any alternate travel routes to the school, the time or the approximate time the child arrives at school or the time school starts for the child, the time or the approximate time the child leaves school or the time school ends for the day, a travel route to an after school activity, if applicable, a travel route to the after school activity, an alternate travel route to the after school activity, a time or an approximate time of a travel to an after school activity, a time or an approximate time when the child leaves the venue of the after school activity, a travel route from the venue of the after school activity to the child's home, a travel route to the child's home, an alternate travel route to the child's home, and/or a time or an approximate time when the child is expected to arrive at home.

As and for another example, in the case of an adult of any age being monitored, the database 10H can contain and/or can include any data and/or information regarding the daily weekday schedule for the adult such as, for example, the adult's home address, the time or approximate time when the adult leaves home for work or some other activity or venue, a preferred travel route the adult takes to go to work or some other activity or venue, any alternate travel routes to the work, activity, or venue, the time or the approximate time the adult arrives at work, the activity, or the venue, the time or the approximate time the adult leaves work, the activity, or the venue, a travel route to another activity or venue, if applicable, a travel route to the other activity or venue, an alternate travel route to the other or venue, a time or an approximate time of a travel to the other activity or venue, a time or an approximate time when the adult leaves the other activity or venue, a travel route from the other activity or venue back to the adult's home, a travel route to the adult's home, an alternate travel route to the adult's home, and/or a time or an approximate time when the adult is expected to arrive at home.

The database 10H can also contain and/or can include any data and/or information regarding any school(s), workplace(s), club(s), activity venue(s), recreational venue(s), entertainment venue(s), or any other place(s), location(s), and/or other venue(s), of the user or individual and/or to which the user or individual travels and/or at which the user or individual is known to spend time. The database 10H can also contain and/or can include any data and/or information regarding the location(s) of any school(s), workplace(s), club(s), activity venue(s), recreational venue(s), entertainment venue(s), or any other place(s), location(s), and/or other venue(s), of the user or individual, which data and/or information can include the name, the address, the telephone number, the website address, the IP address, a description of same, schedule information of or for same, and/or any other information regarding same.

The database 10H can also contain and/or can include any data and/or information regarding any weekday or weekend day schedules or itineraries of the user or individual. The database 10H can also contain and/or can include any data and/or information regarding emergency contacts for the user or the individual, including, for each emergency contact individual, his or her name, telephone number, cellular telephone number, text messaging number, e-mail address, or IP address, or any other information.

The database 10H can also contain and/or can include any data and/or information regarding any personal monitoring accounts the user or individual has or is associated with. The database 10H can also contain and/or can include any data and/or information regarding any persons responsible for monitoring the user or the individual including for each person, his or her name, telephone number, cellular telephone number, text messaging number, e-mail address, or IP address, or any other information. The database 10H can also contain and/or can include any data and/or information regarding any and/or all personal monitoring devices 10 assigned to or associated with the user or individual and/or can contain and/or can include data and/or information regarding with any the user's or individual's personal monitoring accounts.

The database 10H can also contains and/or can include any data and/or information regarding any of the central processing computer(s) 20, any pertinent user communication device(s) 30, any law enforcement communication device(s) 40, any emergency services provider communication device(s) 50, and/or the healthcare records computer(s) 60, described herein, and/or can contain and/or can include any link(s) or hyperlink(s) to same.

The database 10H can also contain and/or can include an electronic healthcare record of the user or the individual and/or any data and/or information regarding same or contained in same, any data and/or information which may be contained in the electronic healthcare record of the user or the individual, any personal healthcare record of the user or individual, any data and/or information which may be contained in the personal healthcare record of the user or the individual, any healthcare information regarding the user or the individual, any information regarding any healthcare condition or special needs of the user or the individual, any information regarding any medicines, prescribed medications, drugs, or prescribed drugs, which are needed by the user or the individual, any information regarding any allergies of the user or the individual, or any other information regarding any healthcare conditions, needs, or treatments, of, for, or regarding, the user or the individual. The database 10H can also contain and/or can include a link or hyperlink to the healthcare records computer 60 and/or to the user's or the individual's electronic healthcare record stored therein.

The database 10H can also contain and/or can include any data and/or information regarding the daily schedule for each weekday or each weekend day for the user or the individual, travel routes travelled for each day and trip, and/or time(s) associated with each trip or travel segment of each trip.

The database 10H can also contain and/or can include any data and/or information regarding the name, address, telephone number(s), cellular telephone number(s), mobile or wireless telephone number(s), e-mail address(es), text messaging address(es), IP address(es), or any other contact information for or regarding any herein-described monitoring person of or for the user or the individual or for each or any parent, sibling, family member, relative, caregiver, nanny, au pair, healthcare provider(s), healthcare insurer(s) or healthcare payer(s), or any other person or entity of or for the user or the individual.

It is important to note, as used throughout the application, the term or phrase "text messaging number" includes any and all kinds of messaging numbers, including, but not limited to, a text messaging number, an SMS messaging number, and MMS messaging number, or any other number, address, or identifier, used or needed in order to send a text message or any other message to any user, individual, person, or entity who or which uses the apparatus 100 of the present invention.

The database 10H can also contain and/or include any software, software program(s), algorithm(s), or software applications ("apps"), such as those known by those skilled in the art at the time of the filing of this application, which can allow the personal monitoring device 10 to ascertain, determine, locate, and/or display, a location or position of any user communication device 30 associated with any user or individual, including, but not limited to, any user or individual who is to be monitoring the user or individual who is using or who is associated with the personal monitoring device 10, or any other authorized or designated user or individual who might be able to provide assistance to the user or individual who is using or who is associated with the personal monitoring device 10.

The database 10H can also contain and/or can include navigation software for allowing the personal monitoring device 10 to calculate travel routes from one place or point to another, to detect departures from a travel route and to re-calculate another travel route, and/or for allowing the personal monitoring device 10 to calculate and/or to store travel routes and/or any data and/or information regarding same which are used by the user or individual as well as alternate travel routes for same. The database 10H can also contain and/or can include any data and/or information regarding any allowed travel routes for the user or individual as well as disallowed travel routes for the user of individual. The database 10H can also contain and/or include map data and/or map information including, but not limited to, digitized map data and/or information and/or data and/or information for updating any map data and/or information.

The database 10H can also contain and/or include data and/or information regarding travel records for the user or individual which can contain and/or include data and/or information regarding a date and time of travel and/or travel routes taken or travelled by, and/or any other data and/or information regarding, the user or individual for or during any period of time or during and/or for or relating to any schedule or routine.

The database 10H can also contain and/or include a pre-recorded audio message(s) and/or a pre-recorded audio and video message(s), which can be recorded by any person authorized to monitor the user or individual and which can provided via the personal monitoring device 10 at any time and/or for any reason. For example, an audio and/or an audio and video recording can be played via the personal monitoring device 10 in order to assist, calm, or comfort, a lost child, to help re-orient a child, to give or provide the child or any one with whom the child comes into contact with, instructions, contact information, emergency contact information, directions, or any other information, and/or can be played to clam, comfort, or assist, a lost, disoriented, or ill, adult or child of any age, or to give or provide the child or any one with whom the child comes into contact with, instructions, contact information, emergency contact information, directions, or any other information.

The database 10H can also contain and/or can include any data, information, software, software programs, algorithms, and/or software applications (or "apps") which are needed or desired for allowing the personal monitoring device 10 to perform any and/or all of the functions and/or functionality described herein as being capable of being performed by same and/or by the apparatus 100 and method of the present invention.

The database 10H can also contain and/or can include any of the data and/or information described herein as being stored in any of the databases of the central processing computer(s) 20, the user communication device(s) 30, the law enforcement communication device(s) 40, the emergency services provider communication device(s) 50, the healthcare records computer(s) 60, the RFID reader system(s) 80, and/or the venue/vehicle computer(s) 90, described herein.

The personal monitoring device 10 also includes an output device(s) 10I for outputting any of the data, information, and/or reports, described herein as being generated by or via the personal monitoring device 10. In the preferred embodiment, the output device(s) 10I can be a display screen, a speaker, a printer, a display of any type or kind, an indicator light, a transmitter, a modem, and/or any other device which can be used to output data or information of any kind or type. In the preferred embodiment, the output device(s) 10I can also include a beacon or a homing beacon which can transmit or provide a signal, a distress signal, or any other indication, from the personal monitoring device 10 which can be utilized determine the position, location, and/or movement, of the personal monitoring device 10. In the preferred embodiment, the output device(s) 10I is/are also connected to, or linked with, the CPU 10A.

The personal monitoring device 10 also includes a video and/or audio recording device(s) 10J which can include a camera and/or a video recording device for recording pictures or video and/or video clips and/or a microphone or an audio recording device for recording audio or audio clips which can be recorded by, and/or transmitted live, by or from the personal monitoring device 10, or which can be recorded by, and stored at or in, the personal monitoring device 10 for transmission by or from the personal monitoring device 10 at a later time. The video and/or audio recording device(s) 10J can be utilized to facilitate video conferencing, video chatting, and/or audio conferencing, and/or video and audio conferencing, between users of the personal monitoring device 10 and any user of any other computer or communication device 10, 20, 30, 40, 50, 60, 80, and/or 90, described herein. In the preferred embodiment, the video and/or audio recording device(s) 10J is/are also connected to, or linked with, the CPU 10A.

With reference to FIG. 2, the personal monitoring device 10 can also include a global positioning system (GPS) device 10K which can be utilized to determine or ascertain the location or position of the personal monitoring device 10 at any time and/or to track movement of the personal monitoring device 10. In a preferred embodiment, the global positioning system (GPS) device 10K can be connected to, or linked with, the CPU 10A.

The personal monitoring device 10 also includes device functional equipment systems or devices 10L, which can include any the necessary communications systems or devices which are typically found in cellular telephones or wireless telephones and/or which can allow the personal monitoring device 10 to function as a cellular telephone or a wireless telephone. In a preferred embodiment, the functional equipment systems or devices 10L can also include a global positioning system (GPS) device which can be utilized to determine or ascertain the location or position of the personal monitoring device 10 at any time and which can be also be used to track movement of the personal monitoring device 10.

In a preferred embodiment, the functional equipment systems or devices 10L can also include navigation equipment or devices which are typically found in navigation devices or equipment and which an be utilized to allow the personal monitoring device 10 to function and/or to operate as a GPS equipped navigation device. In a preferred embodiment, the personal monitoring device 10 can function as a stand alone navigation device, meaning that it can perform any and/or all needed and desired navigation tasks and functions without any interaction with an external computer or device, and/or without having to access a computer over any communication network in order to obtain navigation data, information, and/or instructions, for providing navigation data, information, and/or instructions, to a user of the personal monitoring device 10.

In another preferred embodiment, the functional equipment systems or devices 10L can also include a "kill" switch or associated hardware and/or software for disabling and/or deactivating the personal monitoring device 10 in instances when same might be lost or stolen, so as to prevent its use by another person and/or to prevent any access to any data and/or information stored therein, thereby rendering the personal monitoring device 10 useless to another person after being reported, or discovered as being, lost or stolen.

In another preferred embodiment, the personal monitoring device 10 can also operate in conjunction with an external computer or device in order to obtain navigation data, information, and/or instructions, so as to provide same to a user of the personal monitoring device 10. In another preferred embodiment, the personal monitoring device 10 can process navigation data, information, and/or instructions, on its own as well as receive at least some navigation data, information, and/or instructions, from an external computer or device, in order to provide navigation data, information, and/or instructions, to a user of the personal monitoring device 10. In a preferred embodiment, the functional equipment systems or devices 10L are also connected to, or linked with, the CPU 10A.

In a preferred embodiment, the functional equipment systems or devices 10L can also include any combination of hardware and/or software for disabling the on/off switch of the personal monitoring device 10, so that the personal monitoring device 10 cannot be shut-off, or so that no operation or function of the personal monitoring device 10 can be terminated, and/or so that a telephone call, a telephone communication link, or a communication line or link, cannot be turned off or terminated, by or at the personal communication device 10. In this regard, in the case of an emergency, no telephone call and/or communication line or link between the personal monitoring device 10 and any user communication device(s) 30, the or any central processing computer(s) 20, the or any law enforcement communication device(s) 40, the or any emergency services provider communication device(s) 50, and/or the or any healthcare records computer(s) 60, can be terminated at or by the personal monitoring device 10, so that a communication line, link, or channel can always be maintained with the personal monitoring device 10.

In this regard, for example, if a child is lost, a telephone call and/or communication line, link, or channel, with and between the child and his or her parent can be maintained without the risk of the call being terminated at or by the personal monitoring device 10. In this regard, the parent can continue to speak with and communication with the child, can obtain position or location information from or via the personal monitoring device 10, can track the personal monitoring device 10, and/or can obtain any other information from and/or via the personal monitoring device 10, without losing contact with the child and/or his or her personal monitoring device 10.

In a preferred embodiment, the functional equipment systems or devices 10L can also include any combination of hardware and/or software for allowing the personal monitoring device 10 and any components or devices therein or associated therewith to be remotely accessed, controlled, and/or monitored, by or using any authorized user communication device 30 used by an authorized user or individual, the or any central processing computer(s) 20, the or any law enforcement communication device(s) 40, the or any emergency services provider communication device(s) 50, and/or the or any healthcare records computer(s) 60.

In a preferred embodiment, the personal monitoring device 10 can also include an RFID tag 70 (shown in FIG. 3) which can be attached to, connected to, located on, or located within or inside a housing of, the personal monitoring device 10.

Figure 3:
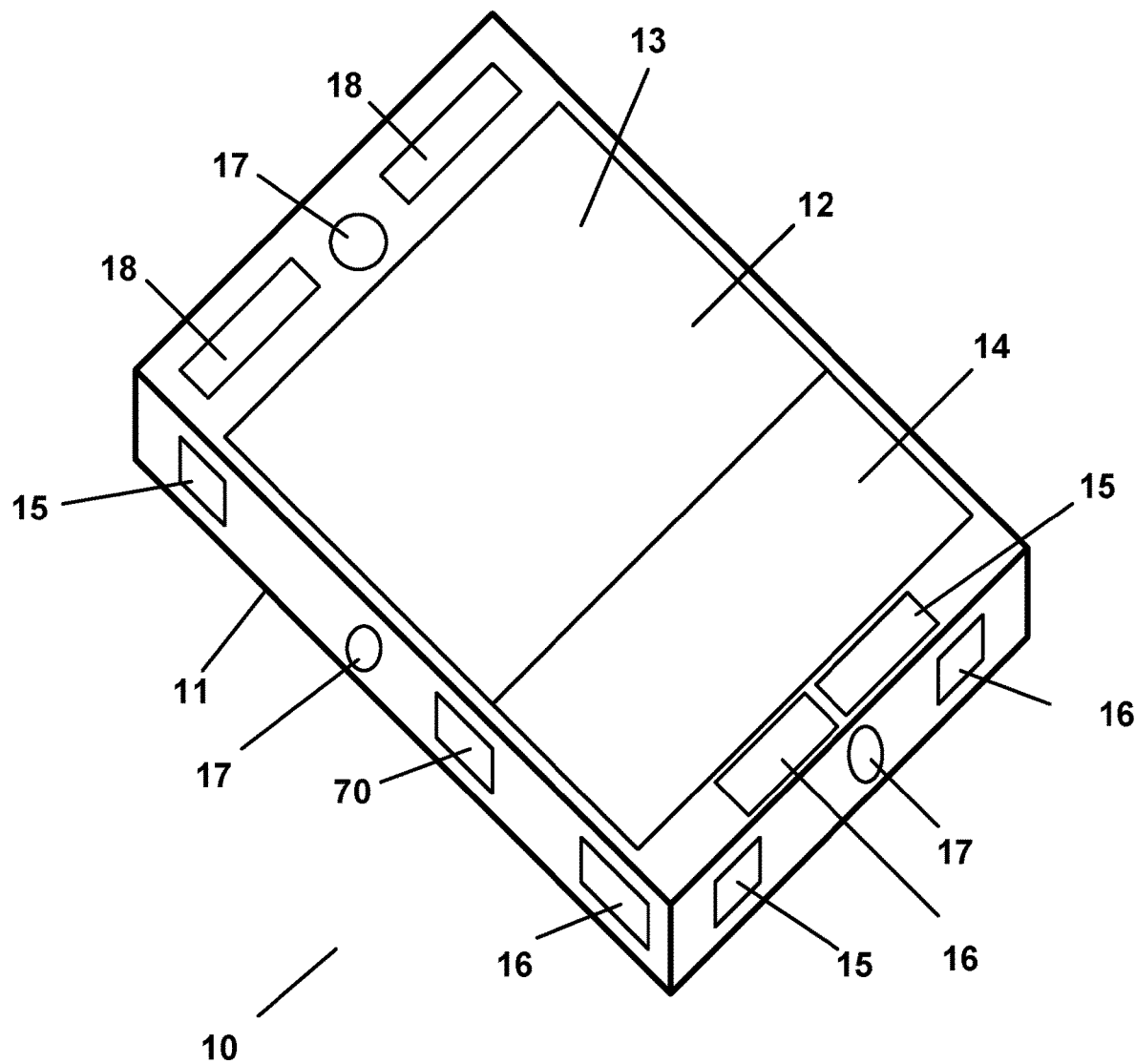
FIG. 3 illustrates the personal monitoring device of FIG. 1 in a three-dimensional perspective view.

FIG. 3 illustrates the personal monitoring device 10 of FIG. 1 in a three-dimensional perspective view. In a preferred embodiment, the personal monitoring device 10 can be, or can be implemented in or with, a cellular telephone, a Smartphone, a smartphone, or a personal digital assistant, which can be equipped with all of the necessary hardware and software needed to perform all of the functions and functionality described herein as being performed by the personal monitoring device 10 of the present invention. In another preferred embodiment, the personal monitoring device 10 can be designed to be of any size or shape, and/or the personal monitoring device 10 can be implemented using a watch, a wristwatch, an necklace, a bracelet, a ring, or any other article of jewelry, of the personal monitoring device 10 can be secured to a belt, a necklace, a bracelet, eyeglasses, a watch, a wristwatch, and/or can be attached to, secured to, or placed inside or within, any article of clothing, a jacket, a coat, a shirt, a blouse, a dress, a skirt, a pair of pants, shoes, sneakers, boots, a hat, gloves, socks, stockings, a tie, a scarf, or any other wearable item or accessory. In this regard, and depending of the use, application, or deployment, of the personal monitoring device 10 in any given setting or situation, the personal monitoring device 10 can be designed and/or configures to be of any size, shape, type, or kind, of device.

With reference to FIG. 3, in a preferred embodiment, the personal monitoring device 10 can include a housing 11, a display screen 12 which can be a component of the display device 10E. In the preferred embodiment, the display screen 12 can of the touch screen type or kind and can be utilized to view and to input data, information, messages, or instructions. In a preferred embodiment, the display screen 12 can include a display section 13 and a keyboard section 14. In a preferred embodiment, the keyboard section 14 can be called upon when needed and can also be dispensed with when not being used so as to facilitate the use of the entirety of the display screen 12 when desired.

In a preferred embodiment, the personal monitoring device 10 can also be equipped with a flashlight, a flashlight bulb, or with any suitable software application which can turn the display screen 12, or any portion of the display screen 12, into a flashlight. In this regard, the personal monitoring device 10 can be equipped with a flashlight or a flashlight functionality.

With reference once again to FIG. 3, the personal monitoring device 10 can also include one or more microphones 15, which can be a component of the video and/or audio recording device(s) 10J and/or the input device 10D and, which can be located on one or more, or on any or all surfaces of the personal monitoring device 10 in order to allow for any user or other individual to utilize the personal monitoring device 10 to communicate with others, to allow others to monitor audio and/or sounds at or in the vicinity of the personal monitoring device 10, and/or to allow one to use, control an operation of, to enter voice commands into, and/or to record audio information or an audio clip with and/or using, the personal monitoring device 10, and/or to allow one to simply utilize the personal monitoring device 10 to communicate with another individual or entity in a hand-free mode of operation. Any number of microphones 15 can be utilized in connection with the personal monitoring device 10.

With reference once again to FIG. 3, the personal monitoring device 10 can also include one or more speakers 16, which can be a component of the output device 10I and, which can be located on one or more, or on any or all, surfaces of the personal monitoring device 10 in order to provide audible data, information, instructions, or communications, to any user, or individual who may be using, or who may be in the vicinity of, the personal monitoring device 10.

With reference once again to FIG. 3, the personal monitoring device 10 can also include one or more cameras 17, which can be a component of the video and/or audio recording device(s) 10J and/or the input device 10I and, which can be located on one or more, or on any or all, surfaces of the personal monitoring device 10 in order to take or record a picture, a photograph, or an image, and/or to record video information or a video clip, with the personal monitoring device 10, to record a picture, a photograph, or an image, and/or to record video information or a video clip, of a user of the personal monitoring device 10 or any individual using the personal monitoring device 10 or in the vicinity of the personal monitoring device 10, to record a picture, a photograph, or an image, and/or to record video information or a video clip, of a vicinity in which the personal monitoring device 10 is located or of a surrounding of same, and/or to allow a user or any individual to engage in a video conference or video chat with another individual or other individuals using the personal monitoring device 10.

In a preferred embodiment, any one or more cameras 17 can be a wide angle lens camera or a camera having a wide angle lens for obtaining maximum viewing area. In a preferred embodiment, any one or more cameras 17 can also be a night vision camera, an infrared camera, or a camera equipped with, or utilized in connection with, night vision capability.

With reference once again to FIG. 3, the personal monitoring device 10 can include a plurality of indicator lights 18, one of which can be used to provide an indication that the user of the personal monitoring device 10 is located with a "safe" zone of travel and the other which can be used to provide an indication that the user of the personal monitoring device 10 is located outside of a "safe" zone of travel, is lost, is ill, is possibly the victim of foul play, or is otherwise in need of help or assistance. In a preferred embodiment, the indicator light which is used to indicate the that user in within his or her "safe" zone can be an green light when illuminated, and the indicator light which is used to indicate the that user outside his or her "safe" zone of travel, is lost, is ill, is possibly the victim of foul play, or is otherwise in need of help or assistance, can be a red light when illuminated. In another preferred embodiment, the indicator lights 19 can be provided via the display screen or in or via a portion or section of the display screen 12.

With reference once again to FIG. 3, the personal monitoring device 10 can include an RFID tag 70 as shown. In a preferred embodiment, the RFID tag 70 can be attached to, connected to, or located at, any part, side, or portion of the housing 11. In another preferred embodiment, the RFID tag 70 can be located within, or inside, the housing 11 of, the personal monitoring device 10. In a preferred embodiment, for a passive RFID tag 70, the RFID tag 70 need not be connected electrically to any component of the personal monitoring device 10. In a preferred embodiment, for an active RFID tag 70, the RFID tag 70 can be electrically connected to the power source (not shown) of the personal monitoring device 10 and/or to the CPU 10A and/or any other component of the personal monitoring device 10.

In another preferred embodiment, the personal monitoring device 10 can include any suitable attachment device or element (not shown) which is attached or connected to, or linked with, the housing 11 and/or the personal monitoring device 10 and which can be used to secure, to mount, or to otherwise attach, the personal monitoring device 10 to, on, or in, a belt, an article of clothing, a watch, a wristwatch, a necklace, a bracelet, eyeglasses, an accessory of any type or kind, a jacket, a coat, a shirt, a blouse, a dress, a skirt, a pair of pants, shoes, sneakers, boots, a hat, gloves, socks, stockings, a tie, a scarf, or any other wearable item or accessory.

In a preferred embodiment, the personal monitoring device 10, its housing 11, and its various component parts described herein, can be constructed or rugged materials in order to protect the personal monitoring device 10 against impacts. In a preferred embodiment, the personal monitoring device 10, its housing 11, and its various component parts described herein, can also be sealed, in any appropriate manner, so as to provide for a personal monitoring device 10 which can be waterproof. In a preferred embodiment, the personal monitoring device 10 can also be designed and manufactured to as to include any suitable or buoyant material(s) which can allow the personal monitoring device 10 to float on water. In a preferred embodiment, the housing 11, or any portion or component of same, can also include made with or from, or can contain a phosphorescent material so that the housing 11, or any portion of the housing 11, of the personal monitoring device 10 can glow-in-the dark or otherwise exhibit glow-in-the-dark or luminescent properties.

Figure 4:
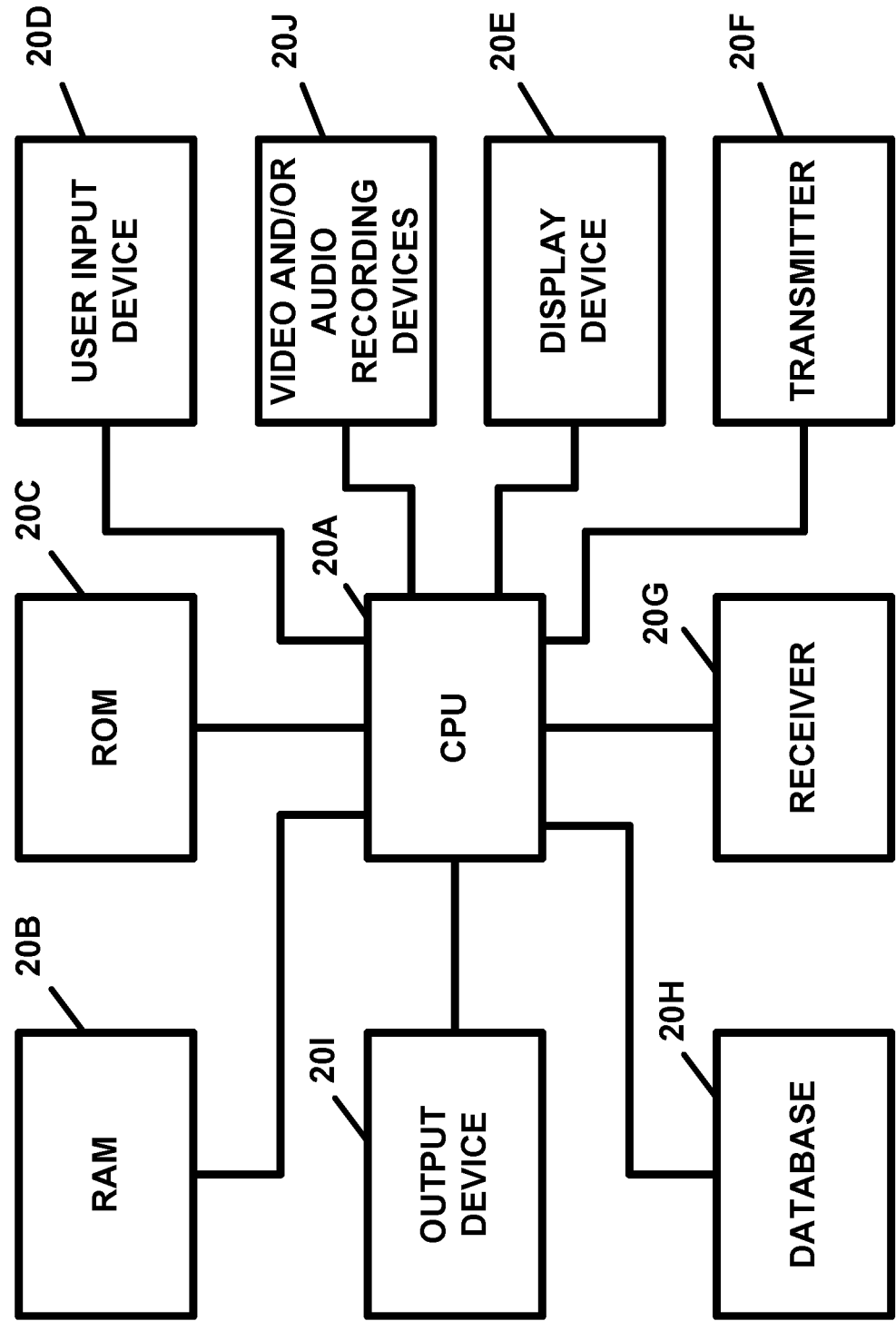
FIG. 4 illustrates the central processing computer of FIG. 1, in block diagram form.

FIG. 4 illustrates the central processing computer 20 of FIG. 1, in block diagram form. In the preferred embodiment, the central processing computer 20 can be any computer capable of performing the functionality of the central processing computer 20 as described herein, a server computer, a computer system, a group of computers, or any computer capable of being utilized in a network or capable of being utilized with other computers in a network, which can provide the functionality of, and which can be utilized as, a central processing computer 20. The central processing computer 20 can also be any suitable server computer or server computer system, a cloud computer or cloud computer system, or any computer or computer system capable of being utilized in a network or capable of being utilized with other computers or computer systems in a network. The central processing computer 20 can also be an Internet server computer and/or a web site server computer. In the preferred embodiment, the central processing computer 20 includes a central processing unit or CPU 20A, which in the preferred embodiment, is a microprocessor. The CPU 20A can also be a microcomputer, a minicomputer, a macro-computer, and/or a mainframe computer, depending upon the application.

The central processing computer 20 also includes a random access memory device(s) 20B (RAM), a read only memory device(s) 20C (ROM), each of which is connected to, or linked with, the CPU 20A, and a user input device 20D, for inputting and/or entering data and/or information and/or instructions and/or commands into the central processing computer 20, which can include any one or more of a keyboard, a scanner, a user pointing device, such as, for example, a mouse, a touch pad, and/or an audio input device and/or a video input device, a microphone or audio recording device, a camera or a video recording device, and/or any device, electronic and/or otherwise which can be utilized for inputting and/or entering data and/or information, as well as instructions and/or commands, into the central processing computer 20. The central processing computer 20 also includes a display device 20E for displaying data and/or information to a user or operator. In the preferred embodiment, the display device 20E is also connected to, or linked with, the CPU 20A.

The central processing computer 20 also includes a transmitter(s) 20F, for transmitting signals and/or data and/or information to any one or more of the personal monitoring device(s) 10, the user communication device(s) 30, the law enforcement communication device(s) 40, the emergency services provider communication device(s) 50, the healthcare records computer(s) 60, the RFID reader system(s) 80, the venue/vehicle computer(s) 90, and/or any other central processing computer(s) 20, which can be utilized in conjunction with the present invention. In the preferred embodiment, the transmitter(s) 20F is/are also connected to, or linked with, the CPU 20A. The central processing computer 20 also includes a receiver(s) 20G, for receiving signals and/or data and/or information from any one or more of the personal monitoring device(s) 10, the user communication device(s) 30, the law enforcement communication device(s) 40, the emergency services provider communication device(s) 50, the healthcare records computer(s) 60, the RFID reader system(s) 80, the venue/vehicle computer(s) 90, and/or any other central processing computer(s) 20, which may be utilized in conjunction with the present invention. In the preferred embodiment, the receiver(s) 20G is/are also connected to, or linked with, the CPU 20A.

The central processing computer 20 also includes a database(s) 20H which, in the preferred embodiment, contains and/or includes any and/or all of the data and/or information needed or desired for or by the central processing computer 20 to perform all of the operations, actions, functions, and/or functionality, described herein as being provided by, and/or as being performed by, the central processing computer 20 and/or the apparatus 100 of the present invention. In the preferred embodiment, the database(s) 20H is/are also connected to, or linked with, the CPU 20A.

In a preferred embodiment, the database(s) 20H can contain and/or include any and/or all of any needed or desired data and information regarding each of the users or individuals being monitored, or are to be monitored, by, with, or using, the apparatus 100, including, but not limited to, any of the data and/or information described herein as being stored in the database 10H of any personal monitoring device 10 associated with or used by the respective user or individual.

In a preferred embodiment, the database(s) 20H can also contain and/or include any and/or all of any needed or desired data and information regarding each of the users or individuals who utilize the apparatus 100 of the present invention to monitor any other user or individual, including, but not limited to, any of the data and/or information described herein as being stored in the database 30H of any user communication device 30 associated with or used by the respective user or individual desiring to monitor any other user or individual.

In a preferred embodiment, for each user or individual who or which uses the apparatus 100 and method of the present invention to monitor another user or individual, the database 20H can contain and/or include, but not be limited to, any data and/or information regarding the user's or the individual's name, address, telephone number(s), cellular telephone number(s), mobile or wireless telephone number(s), e-mail address or e-mail addresses, and/or text message, instant message, SMS message, or MMS message, IP address(es), or any other messaging, telephone number, or other, address or identifier, as well as any data and/or information regarding the user's or the individual's user communication device 30, including, but not limited to, the manufacturer, model number, and/or serial number of same, as well as any telephone number, e-mail address, instant message number or address, SMS message number or address, MMS message number or address, IP address, or any other contact information of, for, or associated with the user communication device 30, for each user communication device 30 used by or associated with the user or individual. The database 20H can also contain and/or include any data and/or information regarding any other user(s) or individual(s) being monitored, or to be monitored, by the user or individual.

In a preferred embodiment, for each user or individual who or which is being monitored, or is to be monitored, by, with, or using, the apparatus 100 and method of the present invention, the database 20H can contain and/or include, but not be limited to, any data and/or information regarding the user's or the individual's name, address, telephone number(s), cellular telephone number(s), mobile or wireless telephone number(s), e-mail address or e-mail addresses, and/or text message, instant message, SMS message, or MMS message, IP address(es), or any other messaging, telephone number, or other, address or identifier, as well as any data and/or information regarding the user's or the individual's personal monitoring device 10, including, but not limited to, the manufacturer, model number, and/or serial number of same, as well as any telephone number, e-mail address, instant message number or address, SMS message number or address, MMS message number or address, IP address, or any other contact information of, for, or associated with the personal monitoring device 10, for each personal monitoring device 10 used by or associated with the user or individual.

For each user or individual who or which utilizes the apparatus 100 and method of the present invention to monitor another user or individual, the database 20H, in a preferred embodiment, can contain and/or include any data and/or information regarding the user(s) or individual(s) being monitored or to be monitored.

For each user or individual being monitored by, or to be monitored by, another user or individual, the database 20H, in a preferred embodiment, can contain and/or include any data and/or information regarding the user(s) or individual(s) who is to monitor that user or individual.

In a preferred embodiment, the database 20H can contain and/or include any data and/or information regarding any personal monitoring account(s) associated with any user(s) or individual(s) who are being monitored, or to be monitored, by, with, or using, the apparatus 100 of the present invention including, but not limited to any number or identifier for the respective personal monitoring account, account number, any user(s) or individual(s) being monitored, or to be monitored, under the personal monitoring account, and/or any user(s) or individual(s) authorized to use the personal monitoring account to monitor another user(s) or individual.

In a preferred embodiment, the database 20H can contain and/or include, for each user or individual being monitored, or to be monitored, by, with, or using, the apparatus 100 and method of the present invention, data and/or information regarding places, locations, or venues, to which the user or individual travels, along with any data and/or information regarding the daily schedule or daily schedules of or for the user or the individual, and/or any data and/or information regarding the daily routine or daily routines of or for the user or individual, any places where the user or individual is or has to be at a given time, and/or any other data and/or information regarding the user's or the individual's daily routines, weekly routines, travel routines, travel routes used, alternate travel routes used, travel times and/or time of travel regarding any travel by the user or individual, and/or any other data and/or information regarding the user's or the individual's routines that can be utilized in performing a personal monitoring service for or regarding the user or the individual.

For example, in the case of a child being monitored, the database 20H can contain and/or can include any data and/or information regarding the daily weekday schedule for the child such as, for example, the child's home address, the time or approximate time when the child leaves home for school, a preferred travel route the child takes to go to school, any alternate travel routes to the school, the time or the approximate time the child arrives at school or the time school starts for the child, the time or the approximate time the child leaves school or the time school ends for the day, a travel route to an after school activity, if applicable, a travel route to the after school activity, an alternate travel route to the after school activity, a time or an approximate time of a travel to an after school activity, a time or an approximate time when the child leaves the venue of the after school activity, a travel route from the venue of the after school activity to the child's home, a travel route to the child's home, an alternate travel route to the child's home, and/or a time or an approximate time when the child is expected to arrive at home.

As and for another example, in the case of an adult of any age being monitored, the database 20H can contain and/or can include any data and/or information regarding the daily weekday schedule for the adult such as, for example, the adult's home address, the time or approximate time when the adult leaves home for work or some other activity or venue, a preferred travel route the adult takes to go to work or some other activity or venue, any alternate travel routes to the work, activity, or venue, the time or the approximate time the adult arrives at work, the activity, or the venue, the time or the approximate time the adult leaves work, the activity, or the venue, a travel route to another activity or venue, if applicable, a travel route to the other activity or venue, an alternate travel route to the other or venue, a time or an approximate time of a travel to the other activity or venue, a time or an approximate time when the adult leaves the other activity or venue, a travel route from the other activity or venue back to the adult's home, a travel route to the adult's home, an alternate travel route to the adult's home, and/or a time or an approximate time when the adult is expected to arrive at home.

For each user or individual being monitored, or to be monitored, by, with, or using, the apparatus 100 of the present invention, the database 20H can also contain and/or can include any data and/or information regarding any school(s), workplace(s), club(s), activity venue(s), recreational venue(s), entertainment venue(s), or any other place(s), location(s), and/or other venue(s), of the user or individual and/or to which the user or individual travels and/or at which the user or individual is known to spend time. The database 20H can also contain and/or can include any data and/or information regarding the location(s) of any school(s), workplace(s), club(s), activity venue(s), recreational venue(s), entertainment venue(s), or any other place(s), location(s), and/or other venue(s), of the user or individual, which data and/or information can include the name, the address, the telephone number, the website address, the IP address, a description of same, schedule information of or for same, and/or any other information regarding same.

The database 20H can also contain and/or can include, for each user or individual monitored, or to be monitored, by, with, or using, the apparatus 100 of the present invention, any data and/or information regarding any weekday or weekend day schedules or itineraries of the user or individual. The database 20H can also contain and/or can include any data and/or information regarding emergency contacts for the user or the individual, including, for each emergency contact individual, his or her name, telephone number, cellular telephone number, text messaging number, e-mail address, or IP address, or any other information.

The database 20H can also contain and/or include any data and/or information regarding schedules, travel schedules, allowed travel routes, disallowed travel route, allowed places, locations, or venues, disallowed places, locations, or venues, and/or limitations or restrictions regarding any of same, for each user or individual monitored, or to be monitored, by, with, or using, the apparatus 100 of the present invention. The database 20H can also contain and/or include, for each user or individual monitored, or to be monitored, by, with, or using, the apparatus 100 of the present invention, data and/or information regarding past travels, movements, or activities, including, but not limited to, travel routes and dates and/or times of same, as well as future travel plans, movements, or activities, for each such user or individual.

The database 20H can also contain and/or include, for each user or individual who is being monitored, or who is to b monitored by, with, or using, the apparatus 100 of the present invention, a pre-recorded a audio message(s) and/or a pre-recorded audio and video message(s), which can be recorded by any person authorized to monitor the user or individual and which can downloaded to the personal monitoring device 10 at any time and/or for any reason. For example, an audio and/or an audio and video recording can be played at the personal monitoring device 10 in order to assist, calm, or comfort, a lost child, to help re-orient a child, to give or provide the child or any one with whom the child comes into contact with, instructions, contact information, emergency contact information, directions, or any other information, and/or can be played at or via the personal monitoring device 10 in order to clam, comfort, or assist, a lost, disoriented, or ill, adult or child of any age, or to give or provide the child or any one with whom the child comes into contact with, instructions, contact information, emergency contact information, directions, or any other information.

The database 20H can also contain and/or include any data and/or information for calculating, tracking, and/or monitoring, travel routes and travel activities for monitored, or to be monitored, by, with, or using, the apparatus 100 of the present invention. The database 20H can also contain and/or include any stored video and/or audio which is recorded by any personal monitoring device 10, as well as any tracking information regarding the personal monitoring device 10 for any personal monitoring device 10 utilized in connection with the apparatus 100 and method of the present invention.

The database 20H can also contain and/or include any data and/or information, as well as any software, software programs, algorithms, and/or software application, for enabling the central processing computer 20, any user communication device 30 associated with an authorized user or individual, any authorized law enforcement personnel, or any authorized emergency services personnel, to access, to monitor or to monitor an operation of, or to control or to control an operation of, a personal monitoring device 10 user by or associated with a user or individual monitored, or to be monitored, by, with, or using, the apparatus 100 of the present invention. In this regard, an authorized user, individual, or personnel can access, monitor, or control, a respective personal monitoring device 10 via the central processing computer 20.

The database 20H can also contain and/or include, for each user or individual monitored, or to be monitored, by, with, or using, the apparatus 100 of the present invention, and for each user or individual who is monitoring, or who is to be monitoring, any other user or individual, an electronic healthcare record, an electronic medical record, an electronic dental record, a healthcare record, and/or a personal healthcare record, for the respective user or individual, which can include any data and/or information typically found in any electronic healthcare records, electronic medical records, electronic dental records, healthcare records, and/or personal healthcare records. The database 20H can also include for each user or individual, information regarding any healthcare conditions of the user or individual, any medicines, medications, or drugs, the user or individual is taking or required to take, any allergies the user or individual may have, and/or any other information which may be needed or useful for the user's or the individual's well being.

The database 20H can also contain and/or include any and/or all data and/or information regarding any and/or all personal monitoring devices 10, any other central processing computer(s) 20, any and/or all user communication devices 30, any and/or all law enforcement communication device(s) 40, any and/or emergency services provider communication device(s) 50, and/or any and/or all healthcare records computer(s) 60, utilized in connection with the apparatus 100 of the present invention, as well any data and/or information stored therein, and/or any link(s) or hyperlink(s) to same or to any data and/or information stored in same.

The database 20H can also contain and/or include any and/or all of the data and/or information described herein as being stored in any of the herein-described databases 10H for any and/or all of the personal monitoring devices 10 utilized with the apparatus 100 and/or can also contain and/or can include any of the data and/or information described herein as being stored in any of the databases of the user communication device(s) 30, the law enforcement communication device(s) 40, the emergency services provider communication device(s) 50, the healthcare records computer(s) 60, the RFID reader system(s) 80, and/or the venue/vehicle computer(s) 90, described herein.

It is to also be understood that the database 20H, in a preferred embodiment, can also contain and/or include any data and/or information, and/or any software, software programs, algorithms, and/or soft applications, needed or desired, whether described herein or not, for allowing the central processing computer 20, the apparatus 100, and/or any of the herein-described personal monitoring devices 10, user communication devices 30, law enforcement communication device(s) 40, emergency services provider communication device(s) 50, and/or any and/or all healthcare records computer(s) 60, to perform the functions described herein as being performed and/or provided by the apparatus 100 and method of the present invention and/or by the central processing computer 20, any personal monitoring device 10, any user communication device 30, any law enforcement communication device 40, any emergency services provider communication device 50, and/or any healthcare records computer 60.

The database 20H can also contain and/or include any software, software program(s), algorithm(s), or software applications ("apps"), such as those known by those skilled in the art at the time of the filing of this application, which can be downloaded at any time to any personal monitoring device 10, and which can allow the personal monitoring device 10 to ascertain, determine, locate, and/or display, a location or position of any user communication device 30 associated with any user or individual, including, but not limited to, any user or individual who is to be monitoring the user or individual who is using or who is associated with the personal monitoring device 10, or any other authorized or designated user or individual who might be able to provide assistance to the user or individual who is using or who is associated with the personal monitoring device 10.

The database 20H can also contain and/or include information regarding each of the herein-described RFID reader systems 80 utilized in connection with the apparatus 100 of the present invention, the respective venue or vehicle in which the RFID system(s) 80 is/are deployed, assigned, or utilized, and/or any RFID readers which are utilized in or in connection with the respective RFID reader system(s) 80. The database 20H can also include the name, address, phone number, position or location information, latitude information or latitude, longitude information or longitude, and/or any other needed or desired information, for or regarding each venue and for or regarding each vehicle in which an RFID reader system 80 is deployed, assigned, or utilized.

In a preferred embodiment, for each venue RFID reader system 80 which is utilized, the database 20H can contain data and/or information which can include, but which is not limited to, a model name of same, an identification number for same, a manufacturer of same, a model number of same, and the type of RFID reader(s) utilized in the same. For each RFID reader system 80 utilized, the database 20H can also include information regarding, for each RFID reader utilized in or with the same, the model name of same, an identification number for same, a manufacturer of same, a model number of same, and/or information regarding the type(s), model(s), and/or model number(s), of the RFID tag(s) which can be read by the respective RFID reader, and/or information regarding whether the RFID reader(s) reads passive RFID tags or active RFID tags.

The database 20H can also contain or include, for each venue or vehicle, the RFID reader system(s) 80 deployed in, assigned to, or utilized in, the same, and information regarding the RFID reader(s) used in same. In a preferred embodiment, for each RFID reader utilized in or at a venue or vehicle, the database 20H can contain information regarding and identification of the entrance point(s) to the venue or the vehicle at which RFID reader(s) is/are stationed, along with information identifying the or each RFID reader, and the exit point(s) of the venue or the vehicle at which the RFID reader(s) is/are stationed, along with information identifying the or each RFID reader.

The database 20H can also contain and/or include any software, software program(s), algorithm(s), or software applications ("apps"), such as those known by those skilled in the art at the time of the filing of this application, which can be downloaded at any time to any user communication device 30, and which can allow the user communication device 30 to ascertain, determine, locate, and/or display, a location or position of any personal monitoring device 10 used by or associated with any user or individual who is being monitoring by the user or individual who is using or who is associated with the user communication device 30.

In a preferred embodiment, the database(s) 20H can also contain and/or include any software programs, software algorithms, and/or software applications ("apps") deemed to be necessary, desirable, and/or useful, in utilizing the apparatus 100 and method of the present invention in the various embodiments described herein. In a preferred embodiment, the database(s) 20H can also contain and/or include any other data and/or information deemed to be necessary, desirable, and/or useful, in utilizing the apparatus 100 and method of the present invention in the various embodiments described herein. The database(s) 20H can also contain and/or include any other data and/or information which is or may be needed and/or desired in performing any and/or all of the features and/or functionality described herein as being provided by the apparatus 100 of the present invention and/or the central processing computer 20.

The database(s) 20H can also contain and/or include any other data and/or information which is or may be needed and/or desired in performing any and/or all of the features and/or functionality described herein as being generated by, and/or provided by, the apparatus 100 of the present invention and/or described herein as being generated by, and/or provided by, the central processing computer 20 and/or any of the communication devices or computers 10, 30, 40, 50, 60, 80, and/or 90. The database(s) 20H can also contain and/or include any of the data and/or information described herein as being stored in any of the databases 10H of the personal monitoring devices 10 utilized in connection with the apparatus 100 and any data and/or information described herein as being stored in any of the databases of the user communication device(s) 30, the law enforcement communication device(s) 40, the emergency services provider communication device(s) 50, the healthcare records computer(s) 60, the RFID reader system(s) 80, and/or the venue/vehicle computer(s) 90, described herein.

The central processing computer 20 also includes an output device(s) 20I for outputting any of the data, information, messages and/or reports, described herein as being generated by or via the central processing computer 20. In the preferred embodiment, the output device(s) 20I can be a printer, a display, a transmitter, a modem, and/or any other device which can be used to output data or information of any kind or type. In the preferred embodiment, the output device(s) 20I is/are also connected to, or linked with, the CPU 20A.

The central processing computer 20 also includes a video and/or audio recording device(s) 20J which can include a camera and/or a video recording device for recording pictures or video and/or video clips and/or a microphone or an audio recording device for recording audio or audio clips which can be recorded by, and/or transmitted live, by or from the central processing computer 20, or which can be recorded by, and stored at or in, the central processing computer 20 for transmission by or from the central processing computer 20 at a later time. The video and/or audio recording device(s) 20J can also be utilized to facilitate one-way broadcasts from the central processing computer 20, and/or can be utilized to facilitate video conferencing, video chatting, and/or audio conferencing, and/or video and audio conferencing, between users of the central processing computer 20 and any of the herein-described users, individuals, providers, or entities, who or which utilize the apparatus 100 and method of the present invention. In the preferred embodiment, the video and/or audio recording device(s) 20J is/are also connected to, or linked with, the CPU 20A.

Figure 5:
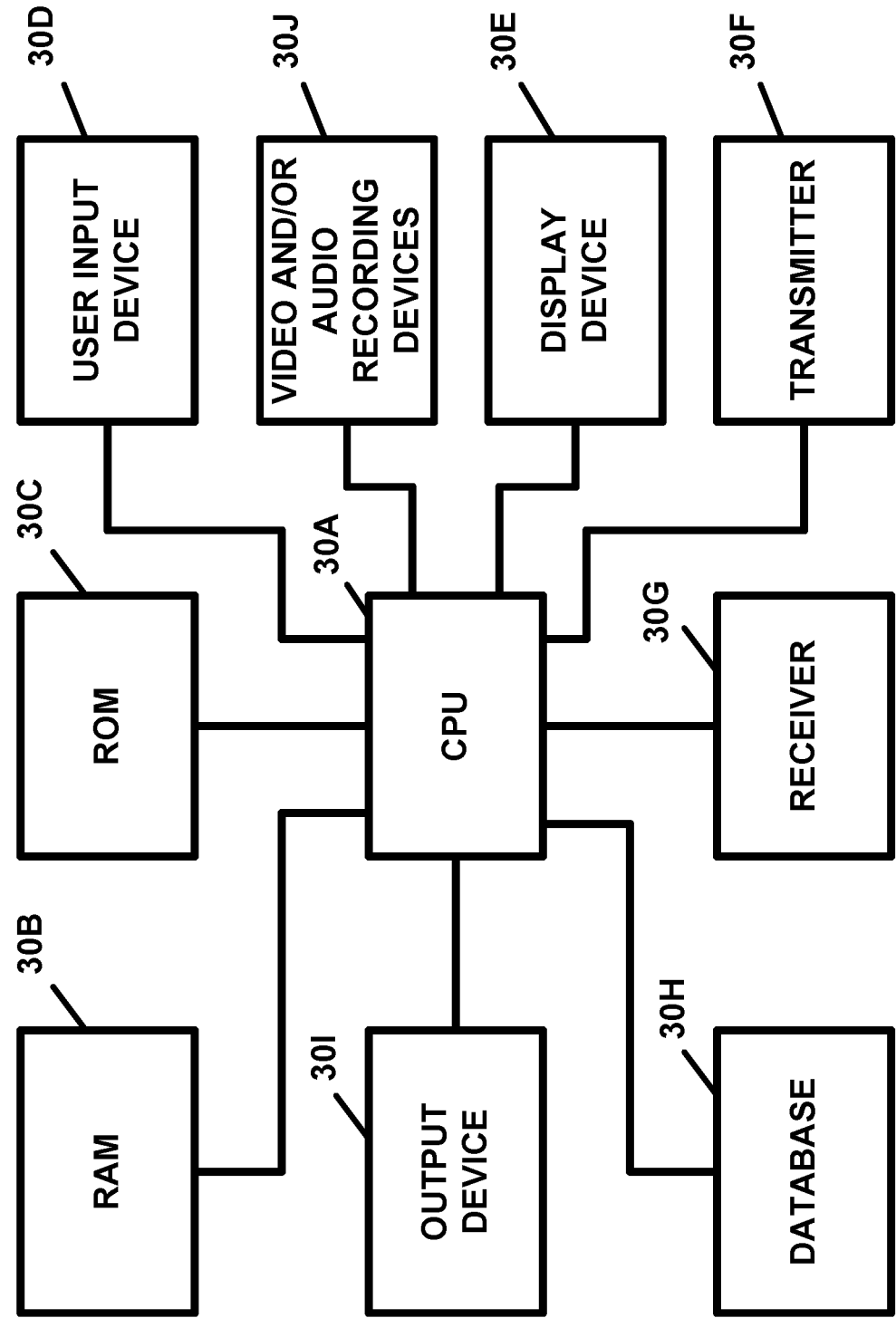
FIG. 5 illustrates the user communication device of FIG. 1, in block diagram form.

FIG. 5 illustrates the user communication device 30 of FIG. 1, in block diagram form. The user communication device 30, in the preferred embodiment, can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The user communication device 30 can also be a server computer, or any computer capable of being utilized in a network or capable of being utilized with other computers in a network.

With reference to FIG. 5, in the preferred embodiment, the user communication device 30 includes a central processing unit or CPU 30A, which in the preferred embodiment, is a microprocessor. The CPU 30A can also be a microcomputer, a minicomputer, a macro-computer, and/or a mainframe computer, depending upon the application.

The user communication device 30 also includes a random access memory device(s) 30B (RAM), a read only memory device(s) 30C (ROM), each of which is connected to, or linked with, the CPU 30A, and a user input device 30D, for inputting and/or entering data and/or information and/or instructions and/or commands into the user communication device 30, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the user communication device 30. The input device(s) 30D is/are also connected to, or linked with, the CPU 30A.

The user communication device 30 also includes a display device 30E for displaying data and/or information to a user or operator. In the preferred embodiment, the display device 30E is also connected to, or linked with, the CPU 30A. The user communication device 30 also includes a transmitter(s) 30F, for transmitting signals and/or data and/or information to any one or more of the personal monitoring device(s) 10, the central processing computer(s) 20, the law enforcement communication device(s) 40, the emergency services provider communication device(s) 50, the healthcare records computer(s) 60, the RFID reader system(s) 80, the venue/vehicle computer(s) 90, and/or any other user communication device(s) 30, which can be utilized in conjunction with the present invention. In the preferred embodiment, the transmitter(s) 30F is/are also connected to, or linked with, the CPU 30A. The user communication device 30 also includes a receiver(s) 30G, for receiving signals and/or data and/or information from any one or more of the personal monitoring device(s) 10, the central processing computer(s) 20, the law enforcement communication device(s) 40, the emergency services provider communication device(s) 50, the healthcare records computer(s) 60, the RFID reader system(s) 80, the venue/vehicle computer(s) 90, and/or any other user communication device(s) 30, which can be utilized in conjunction with the present invention. In the preferred embodiment, the receiver(s) 30G is/are also connected to, or linked with, the CPU 30A.

The user communication device 30 also includes a database(s) 30H. In the preferred embodiment, the database(s) 30H is/are also connected to, or linked with, the CPU 30A. The database(s) 30H can contain and/or be linked to any of the data and/or information described herein as being stored in the database(s) 20H as well as any data and/or information described herein as being stored in the database 10H of each user or individual monitored by the user or individual who is associated with, or who uses the user communication device.

The database(s) 30H can contain and/or include data and/or information regarding the user or the individual, or any users or individuals, who or which utilize the user communication device 30, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, IP address(es), or any other messaging, telephone number, or other, address or identifier.

In a preferred embodiment, the database 30H can contain and/or can include any data and/or information, and/or any link or links to any data and/or information, needed or desired for enabling and/or for allowing the user communication device 30H and/or the apparatus 100 and/or any of the computers or communication devices described herein as being utilized in conjunction with the apparatus 100 and method of the present invention to perform any and/or all of the functionality described herein which is capable of being performed by the user communication device 30 and/or the apparatus 100 of the present invention.

In a preferred embodiment, the database 30H can contain and/or can include any software, software programs, algorithms, or software applications ("apps") needed or desired for enabling and/or for allowing the user communication device 30 and/or the apparatus 100 and/or any of the computers or communication devices described herein as being utilized in conjunction with the apparatus 100 and method of the present invention to perform any and/or all of the functionality described herein which is capable of being performed by the user communication device 30 and/or the apparatus 100 of the present invention.

In a preferred embodiment, the database(s) 30H can contain and/or can include any data and/or information regarding the user communication device 30, the name of the user or the individual, or any users or individuals, including, but is not limited to, who utilize the user communication device 30, including, but not limited to, the user's or the individual's name, address, home telephone number, e-mail address, IP address, test messaging number, text messaging address, cellular telephone number, and the telephone number assigned to the user communication device 30, as well as the date of birth, gender, height, weight, identification photograph, social security number or any other suitable identification information, and/or any other data and/or information regarding the user of the user communication device 30.

In a preferred embodiment, the database(s) 30H can contain and/or can include, for each user or individual who is to be monitored or who is being monitored by, with, or using, the user communication device 30, any data and/or information regarding the user or the individual, or any users or individuals, including, but is not limited to, the user's or the individual's name, address, home telephone number, e-mail address, IP address, test messaging number, text messaging address, cellular telephone number, the telephone number assigned to the personal monitoring device 10, date or birth, gender, height, weight, identification photograph, social security number or any other suitable identification information, and/or any other data and/or information regarding the user of the individual being to be monitored or is to be monitored.

The database 30H can also contain and/or can include for each user, individual, or person, who is to be monitored or who is being monitored by, with, or using, the user communication device 30, any data and/or information regarding the user, the individual's, or the person's, personal monitoring device 10 which can include, but which is not limited to, the type of device, such as for example, a cellular telephone, Smartphone, smartphone, personal digital assistant, or any other device described herein which can be utilized as a personal monitoring device 10, the manufacturing and model number of personal communication device 10, a serial number of the personal monitoring device 10, any other identifying data and/or information assigned to, associated with, or relating to, the personal monitoring device 10, the telephone number associated with, or assigned to, the personal communication device 10, the cellular telephone number associated with, or assigned to, the personal communication device 10, the wireless or mobile telephone number associated with, or assigned to, the personal communication device 10, an IP address associated with, or assigned to, the personal monitoring device 10, an email address associated with, or assigned to the personal monitoring device 10, a text messaging number associated with, or assigned to, the personal monitoring device 10, and/or any other data and/or information associated with the personal monitoring device 10. The database 30H can also contain and/or can include any of the above-described information for any other personal monitoring device(s) 10 or any number of personal monitoring devices 10 which is/are used by the user or individual being monitored or to be monitored.

The database 10H can also contain and/or can include any data and/or information regarding the user or individual who uses the user communication device 30. In a preferred embodiment, the user or individual who is using the user communication device 30 can be, but is not limited to, a parent or parents, spouse, sibling, relative, friend, nanny, au pair, caregiver, teacher, employer, or any other person or entity, of the user or individual being monitored or to be monitored. In a preferred embodiment, the database 30H can contain and/or can include the name, address, telephone number, cellular telephone number, user communication device telephone number or cellular telephone number, e-mail address, IP address, text messaging number, and/or any other data and/or information, and/or contact information, of, for, or regarding, the user or individual who is using the user communication device 30. The database 30H can also contain and/or can include any other data and/or information, described herein as being stored for or regarding the user or individual who uses the user communication device 30.

The database 30H can also contain and/or can include, for each user or individual being monitored by or to be monitored by, with, or using, the user communication device 30, any data and/or information regarding places, locations, or venues, to which each user or individual being monitored by or to be monitored by the user communication device 30, travels. The database 30H can also contain and/or can include data and/or information regarding the daily schedule or daily schedules of or for the each user or individual being monitored by or to be monitored by, with, or using, the user communication device 30, and/or any data and/or information regarding the daily routine or daily routines of or for the each user or individual being monitored by or to be monitored by, with, or using, the user communication device 30, any places where the user or individual being monitored or to be monitored, is or has to be at a given time, and/or any other data and/or information regarding the daily routines, weekly routines, travel routines, travel routes used, alternate travel routes used, travel times and/or time of travel regarding any travel by, the user or individual being monitored or to be monitored, and/or any other data and/or information regarding the routines that can be utilized in performing a personal monitoring service for or regarding each user, individual, or person, being monitored or to be monitored by, with, or using, the user communication device 30.

For example, in the case of a child being monitored by, with, or using, the user communication device 30, the database 30H can contain and/or can include, for that child, any data and/or information regarding the daily weekday schedule for the child such as, for example, the child's home address, the time or approximate time when the child leaves home for school, a preferred travel route the child takes to go to school, any alternate travel routes to the school, the time or the approximate time the child arrives at school or the time school starts for the child, the time or the approximate time the child leaves school or the time school ends for the day, a travel route to an after school activity, if applicable, a travel route to the after school activity, an alternate travel route to the after school activity, a time or an approximate time of a travel to an after school activity, a time or an approximate time when the child leaves the venue of the after school activity, a travel route from the venue of the after school activity to the child's home, a travel route to the child's home, an alternate travel route to the child's home, and/or a time or an approximate time when the child is expected to arrive at home.

As and for another example, in the case of an adult of any age being monitored by, with, or using, the user communication device 30, the database 30H can contain and/or can include, for that adult, any data and/or information regarding the daily weekday schedule for the adult such as, for example, the adult's home address, the time or approximate time when the adult leaves home for work or some other activity or venue, a preferred travel route the adult takes to go to work or some other activity or venue, any alternate travel routes to the work, activity, or venue, the time or the approximate time the adult arrives at work, the activity, or the venue, the time or the approximate time the adult leaves work, the activity, or the venue, a travel route to another activity or venue, if applicable, a travel route to the other activity or venue, an alternate travel route to the other or venue, a time or an approximate time of a travel to the other activity or venue, a time or an approximate time when the adult leaves the other activity or venue, a travel route from the other activity or venue back to the adult's home, a travel route to the adult's home, an alternate travel route to the adult's home, and/or a time or an approximate time when the adult is expected to arrive at home.

The database 30H can also contain and/or can include, for each user, individual, or person, being monitored by, with, or using, the user communication device 30, any data and/or information regarding any school(s), workplace(s), club(s), activity venue(s), recreational venue(s), entertainment venue(s), or any other place(s), location(s), and/or other venue(s), of the respective user, individual, or person, and/or to which the user, individual, or person, travels and/or at which the user, individual, or person, is known to spend time. The database 30H can also contain and/or can include for each user, individual, or person, being monitored by, with, or using, the user communication device 30, any data and/or information regarding the location(s) of any school(s), workplace(s), club(s), activity venue(s), recreational venue(s), entertainment venue(s), or any other place(s), location(s), and/or other venue(s), of the respective user, individual, or person, which data and/or information can include the name, the address, the telephone number, the website address, the IP address, a description of same, schedule information of or for same, and/or any other information regarding same.

The database 30H can also contain and/or can include any data and/or information regarding any weekday or weekend day schedules or itineraries of any user, individual, or person, who is monitored by or is being monitored by, with, or using, the user communication device 30. The database 30H can also contain and/or can include any data and/or information regarding emergency contacts for the user of, or the individual who uses, the user communication device 30, as well as any information regarding any emergency contact for each user, individual, or person, monitored or being monitored by, with, or using, the user communication device 30, including, including, for the user or and/or each user or individual monitored or being monitored by, with, or using, the user communication device 30, any data and/or information regarding each respective emergency contact individual, his or her name, telephone number, cellular telephone number, text messaging number, e-mail address, or IP address, or any other information.

The database 30H can also contain and/or can include any data and/or information regarding any personal monitoring accounts associated with the user communication device 30. The database 30H can also contain and/or can include any data and/or information regarding any persons responsible for monitoring the user or the individual who uses the user communication device 30 as well as any data and/or information regarding the each user, individual, or person, who is to be monitored by, with, or using, the user communication device 30, including, but not limited to, for each user, individual, or person, his or her name, telephone number, cellular telephone number, text messaging number, e-mail address, or IP address, or any other information. The database 30H can also contain and/or can include any data and/or information regarding any and/or all personal monitoring devices 10 assigned to or associated with the user communication device 30 and/or can contain and/or can include any data and/or information regarding with any personal monitoring accounts which are associated with, or which can be monitored or serviced by, the user communication device 30.

The database 30H can also contain and/or can include any data and/or information regarding any of the personal monitoring devices 10, any central processing computer(s) 20, any other user communication device(s) 30, any law enforcement communication device(s) 40, any emergency services provider communication device(s) 50, and/or the healthcare records computer(s) 60, described herein, and/or can contain and/or can include any link(s) or hyperlink(s) to same.

The database 30H can also contain and/or can include an electronic healthcare record of the user or the individual who is using the user communication device 30, as well an electronic healthcare record of each user, individual, or person, monitored by, with, or using, the user communication device 30, as well as any data and/or information which may be contained in the electronic healthcare record of each respective user or individual, any personal healthcare record of each respective user or individual, any data and/or information which may be contained in the personal healthcare record of each respective user or individual, any healthcare information regarding each respective user or individual, any information regarding any healthcare condition or special needs of each respective user or individual, any information regarding any medicines, prescribed medications, drugs, or prescribed drugs, which are needed by each respective user or individual, any information regarding any allergies of each respective user or individual, or any other information regarding any healthcare conditions, needs, or treatments, of, for, or regarding, each respective user or individual. The database 30H can also contain and/or can include a link or hyperlink to the healthcare records computer 60 and/or to any pertinent records, data, and/or information, stored therein as well as any of the law enforcement communication device(s) 40, the emergency services provider communication device(s) 50, the healthcare records computer(s) 60, the RFID reader system(s) 80, and/or the venue/vehicle computer(s) 90, described herein.

The database 30H can also contain and/or can include data and/or information regarding the daily schedule for each weekday or each weekend day for the each user, individual, or person, monitored by, with, or using, the user communication device 30, travel routes travelled for each day and trip, and/or time(s) associated with each trip or travel segment of each trip.

The database 30H can also contain and/or can include, for any user, individual, or person, monitored by, with, or using, the user communication device 30, any data and/or information regarding the name, address, telephone number(s), cellular telephone number(s), mobile or wireless telephone number(s), e-mail address(es), text messaging address(es), IP address(es), or any other contact information for or regarding the user, individual, or person, or any users or individuals authorized to monitor that user, individual, or person.

It is important to note, as used throughout the application, the term or phrase "text messaging number" includes any and all kinds of messaging numbers, including, but not limited to, a text messaging number, an SMS messaging number, and MMS messaging number, or any other number, address, or identifier, used or needed in order to send a text message or any other message to any user, individual, person, or entity who or which uses the apparatus 100 of the present invention.

The database 30H can also contain and/or include any software, software program(s), algorithm(s), or software applications ("apps"), such as those known by those skilled in the art at the time of the filing of this application, which can be downloaded at any time to the user communication device 30, and which can allow the user communication device 30 to ascertain, determine, locate, and/or display, a location or position of any personal monitoring device 10 used by or associated with any user or individual who is being monitoring by the user or individual who is using or who is associated with the user communication device 30.

The database 30H can also contain and/or can include navigation software for allowing the user communication device 30 to calculate travel routes, for the user or individual using the user communication device 30, as well as for each and/or any user, individual, or person, or their personal monitoring device 10, which is monitored or being monitored, by, with, or using, the user communication device 30, for travel from one place or point to another, to detect departures from a travel route and to re-calculate another travel route, and/or for allowing the user communication device 30 to calculate and/or store travel routes and/or any data and/or information regarding same as well as alternate travel routes for same. The database 30H can also contain and/or can include any data and/or information regarding allowed travel routes for any user, individual, or person, monitored or being monitored, by, with, or using, the user communication device 30, as well as any disallowed travel routes for the user, individual, or person, monitored or being monitored, by, with, or using, the user communication device 30. The database 30H can also contain and/or can include map data and/or map information including, but not limited to, digitized map data and/or information and/or data and/or information for updating any map data and/or information.

The database 30H can also contain and/or include, for any user, individual, or person, monitored or being monitored, by, with, or using, the user communication device 30, any data and/or information regarding travel records for each respective user, individual, or person, which can contain and/or include data and/or information regarding a date and time of travel and/or travel routes taken or travelled by, and/or any other data and/or information regarding, the respective user, individual, or person, for or during any period of time or during and/or for or relating to any schedule or routine.

The database 30H can also contain and/or include a pre-recorded audio message(s) and/or a pre-recorded audio and video message(s), which can be recorded by any person authorized to monitor the user or individual and which can be uploaded to the central processing computer 20, and/or which can be transmitted to the personal monitoring device 10, at any time, and which can be provided at and/or via the personal monitoring device 10 at any time and/or for any reason. For example, an audio and/or an audio and video recording can be played via the personal monitoring device 10 in order to assist, calm, or comfort, a lost child, to help re-orient a child, to give or provide the child or any one with whom the child comes into contact with, instructions, contact information, emergency contact information, directions, or any other information, and/or can be played to clam, comfort, or assist, a lost, disoriented, or ill, adult or child of any age, or to give or provide the child or any one with whom the child comes into contact with, instructions, contact information, emergency contact information, directions, or any other information.

The database 30H can also contain and/or include any data and/or information, and/or any software, software programs, algorithms, or software applications for controlling and/or monitoring any operation or function of any personal monitoring device 10 associated with any user of individual who is monitored or being monitored by, with, or using, the user communication device 30. The database 30H can also contain and/or include any data and/or information, and/or any software, software programs, algorithms, or software applications for tracking the position, location, or whereabouts, of any personal monitoring device 10 associated with any user of individual who is monitored or to be monitored by, with, or using, the user communication device 30.

The database 30H can also contain and/or can include any data, information, software, software programs, algorithms, and/or software applications (or "apps") which are needed or desired for allowing the user communication device 30 to perform any and/or all of the functions and/or functionality described herein as being capable of being performed by same and/or by the apparatus 100 and method of the present invention.

The database 30H can also contain and/or include any and/or all of the data and/or information described herein as being stored in any of the herein-described databases 10H for any and/or all of the personal monitoring devices 10 utilized with the apparatus 100, any and/or any and/or all of the data and/or information described herein as being stored in the database 20H of the central processing computer 20, and/or any and/or all of the data and/or information described herein as being stored in any of the databases of the law enforcement communication device(s) 40, the emergency services provider communication device(s) 50, the healthcare records computer(s) 60, the RFID reader system(s) 80, and/or the venue/vehicle computer(s) 90, described herein.

The user communication device 30 also includes an output device(s) 30I for outputting any of the data, information, and/or reports, described herein as being generated by or via the user communication device 30. In the preferred embodiment, the output device(s) 30I can be a display screen, a speaker, a printer, a display of any type or kind, an indicator light, a transmitter, a modem, and/or any other device which can be used to output data or information of any kind or type. In the preferred embodiment, the output device(s) 30I is/are also connected to, or linked with, the CPU 30A.

The user communication device 30 also includes a video and/or audio recording device(s) 30J which can include a camera and/or a video recording device for recording pictures or video and/or video clips and/or a microphone or an audio recording device for recording audio or audio clips which can be recorded by, and/or transmitted live, by or from the user communication device 30, or which can be recorded by, and stored at or in, the user communication device 30 for transmission by or from the user communication device 30 at a later time. The video and/or audio recording device(s) 30J can be utilized to facilitate video conferencing, video chatting, and/or audio conferencing, and/or video and audio conferencing, between users of the user communication device 30 and any user of any other computer or communication device 10, 20, 30, 40, 50, 60, 80, and/or 90, described herein. In the preferred embodiment, the video and/or audio recording device(s) 30J is/are also connected to, or linked with, the CPU 30A.

In another preferred embodiment, the user communication device 30 can also include a "kill" switch or associated hardware and/or software (not shown) for disabling and/or deactivating the user communication device 30 in instances when same might be lost or stolen, so as to prevent its use by another person and/or to prevent any access to any data and/or information stored therein, thereby rendering the user communication device 30 useless to another person after being reported, or being discovered, as being lost or stolen.

Figure 6:
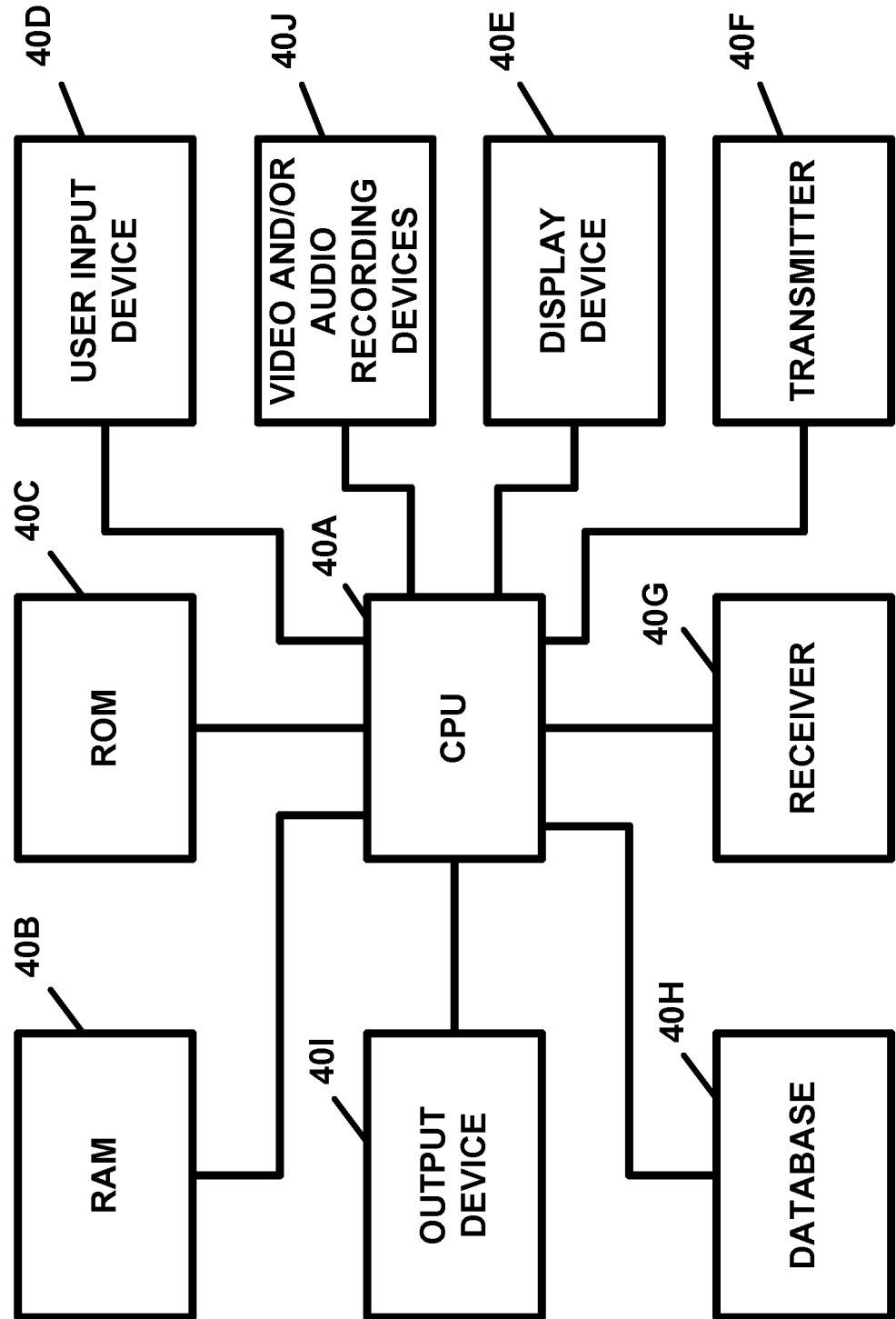
FIG. 6 illustrates the law enforcement communication device of FIG. 1, in block diagram form.

FIG. 6 illustrates the law enforcement communication device 40 of FIG. 1, in block diagram form. The law enforcement communication device 40, in the preferred embodiment, can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The law enforcement communication device 40 can also be a server computer, or any computer capable of being utilized in a network or capable of being utilized with other computers in a network.

With reference to FIG. 6, in the preferred embodiment, the law enforcement communication device 40 includes a central processing unit or CPU 40A, which in the preferred embodiment, is a microprocessor. The CPU 40A can also be a microcomputer, a minicomputer, a macro-computer, and/or a mainframe computer, depending upon the application.

The law enforcement communication device 40 also includes a random access memory device(s) 40B (RAM), a read only memory device(s) 40C (ROM), each of which is connected to, or linked with, the CPU 40A, and a user input device 40D, for inputting and/or entering data and/or information and/or instructions and/or commands into the law enforcement communication device 40, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the law enforcement communication device 40. The input device(s) 40D is/are also connected to, or linked with, the CPU 40A.

The law enforcement communication device 40 also includes a display device 40E for displaying data and/or information to a user or operator. In the preferred embodiment, the display device 40E is also connected to, or linked with, the CPU 40A. The law enforcement communication device 40 also includes a transmitter(s) 40F, for transmitting signals and/or data and/or information to any one or more of the personal monitoring device(s) 10, the central processing computer(s) 20, the user communication device(s) 30, the emergency services provider communication device(s) 50, the healthcare records computer(s) 60, the RFID reader system(s) 80, the venue/vehicle computer(s) 90, and/or the healthcare records computer(s) 60, and/or any other the law enforcement communication device(s) 40, which can be utilized in conjunction with the present invention. In the preferred embodiment, the transmitter(s) 40F is/are also connected to, or linked with, the CPU 40A. The law enforcement communication device 40 also includes a receiver(s) 40G, for receiving signals and/or data and/or information from any one or more of the personal monitoring device(s) 10, the central processing computer(s) 20, the user communication device(s) 30, the emergency services provider communication device(s) 50, the healthcare records computer(s) 60, the RFID reader system(s) 80, the venue/vehicle computer(s) 90, and/or any other law enforcement communication device(s) 40, which can be utilized in conjunction with the present invention. In the preferred embodiment, the receiver(s) 40G is/are also connected to, or linked with, the CPU 40A.

The law enforcement communication device 40 also includes a database(s) 40H. In the preferred embodiment, the database(s) 40H is/are also connected to, or linked with, the CPU 40A. The database(s) 40H can contain and/or include, and/or can contain and/or include a link(s) or hyperlink(s) to, and/or can be linked to or with, any of the data and/or information described herein as being stored in the database(s) 10H, 20H, 30H, and/or in any of the databases of any of the emergency services provider communication device(s) 50, the healthcare records computer(s) 60, the RFID reader system(s) 80, and/or the venue/vehicle computer(s) 90, described herein, for any user or individual monitored, or to be monitored, by, with, or using, the apparatus 100 of the present invention and/or for any personal monitoring account being serviced by the apparatus 100 of the present invention. The database(s) 40H can also contain and/or include, and/or can contain and/or include a link(s) or hyperlink(s) to, and/or can be linked to or with, any of the data and/or information described herein as being stored in the database(s) 10H, 20H, 30H, and/or in any of the databases of any of the emergency services provider communication device(s) 50, the healthcare records computer(s) 60, the RFID reader system(s) 80, and/or the venue/vehicle computer(s) 90, described herein, for or regarding any user or individual who or which uses a user communication device 30 to monitor another user or individual. The database(s) 40H can also contain and/or include, and/or can contain and/or include a link(s) or hyperlink(s) to, and/or can be linked to or with, any of the data and/or information described herein as being stored in the database(s) 10H, 20H, 30H, and/or in any of the databases of any of the emergency services provider communication device(s) 50, the healthcare records computer(s) 60, the RFID reader system(s) 80, and/or the venue/vehicle computer(s) 90, described herein, for or regarding any user or individual who or which uses a personal monitoring device 10 to allow himself or herself to be monitored by another user or individual via the apparatus 100 and method of the present invention.

The database(s) 40H can also contain and/or include any data and/or information regarding the user or the individual, or any users or individuals, who or which utilize any user communication device 30 or any user or individual who utilizes a personal monitoring device 10, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, or any other messaging, telephone number or other address or identifier.

The database 40H can also contain and/or include any other data and/or information, and/or any software, software programs, algorithms, and/or software applications, described herein or otherwise, which are needed or desired for enabling the law enforcement communication device 40 to perform any and/or all of the functions and/or functionality described herein as being performed by same.

The law enforcement communication device 40 also includes an output device(s) 40I for outputting any of the data, information, and/or reports, described herein as being generated by or via the law enforcement communication device(s) 40. In the preferred embodiment, the output device 40I can be a display screen, a speaker, a printer, a display of any type or kind, an indicator light, a transmitter, a modem, and/or any other device which can be used to output data or information of any kind or type. In the preferred embodiment, the output device(s) 40I is/are also connected to, or linked with, the CPU 40A.

The law enforcement communication device 40 also includes a video and/or audio recording device(s) 40J which can include a camera and/or a video recording device for recording pictures or video and/or video clips and/or a microphone or an audio recording device for recording audio or audio clips which can be recorded by, and/or transmitted live, by or from the law enforcement communication device 40, or which can be recorded by, and stored at or in, the law enforcement communication device 40 for transmission by or from the law enforcement communication device 40 at a later time. The video and/or audio recording device(s) 40J can be utilized to facilitate video conferencing, video chatting, and/or audio conferencing, and/or video and audio conferencing, between users of the law enforcement communication device 40 and any user of any other computer or communication device 10, 20, 30, 40, 50, 60, 80, and/or 90, described herein. The video and/or audio recording device(s) 40J can also be utilized to facilitate one-way broadcasts from the law enforcement communication device 40. In the preferred embodiment, the video and/or audio recording device(s) 40J is/are also connected to, or linked with, the CPU 40A.

Figure 7:
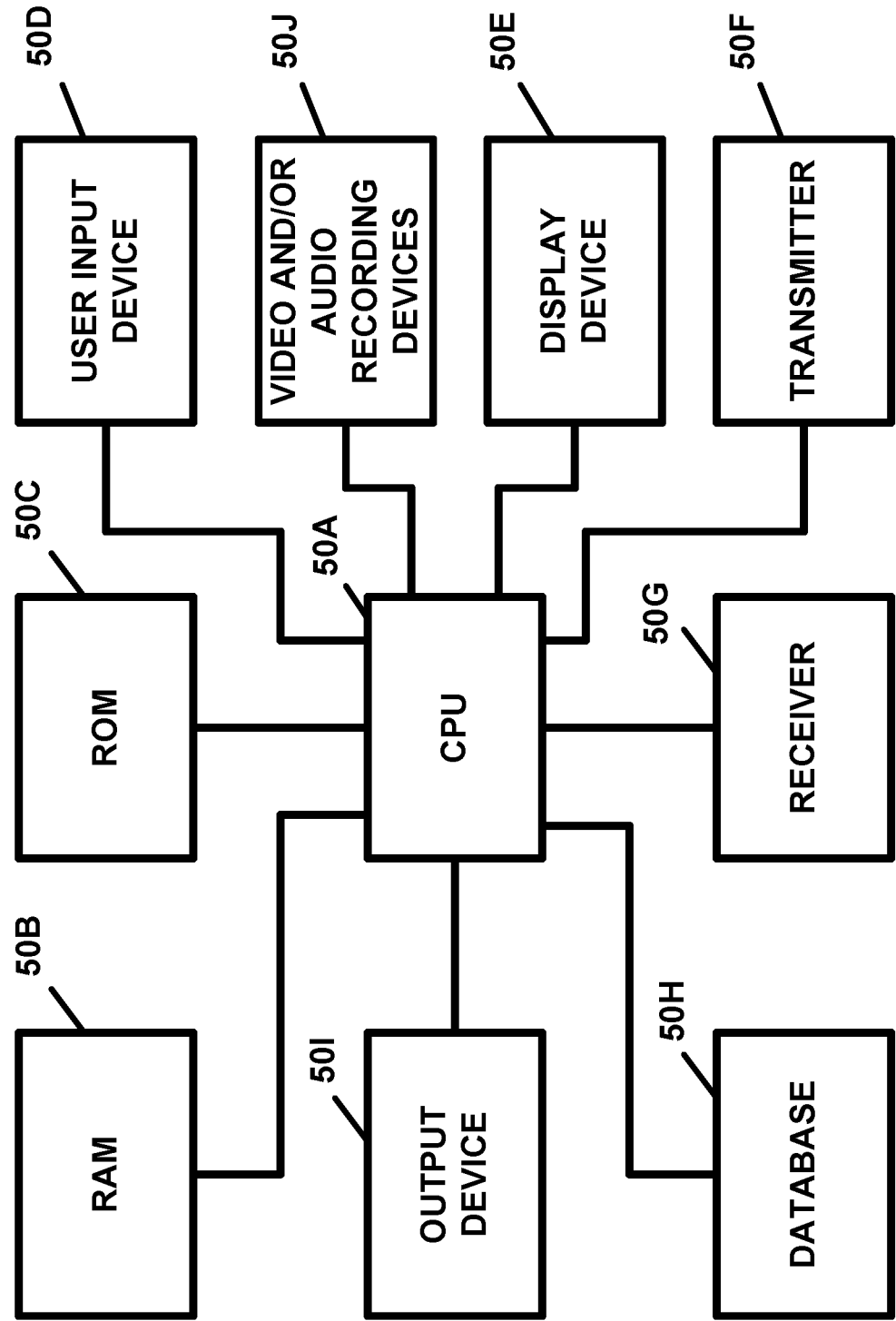
FIG. 7 illustrates the emergency services provider communication device of FIG. 1, in block diagram form.

FIG. 7 illustrates the emergency services provider communication device 50 of FIG. 1, in block diagram form. The emergency services provider communication device 50, in the preferred embodiment, can be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The emergency services provider communication device 50 can also be a server computer, or any computer capable of being utilized in a network or capable of being utilized with other computers in a network.

With reference to FIG. 7, in the preferred embodiment, the emergency services provider communication device 50 includes a central processing unit or CPU 50A, which in the preferred embodiment, is a microprocessor. The CPU 50A can also be a microcomputer, a minicomputer, a macrocomputer, and/or a mainframe computer, depending upon the application.

The emergency services provider communication device 50 also includes a random access memory device(s) 50B (RAM), a read only memory device(s) 50C (ROM), each of which is connected to, or linked with, the CPU 50A, and a user input device 50D, inputting and/or entering data and/or information and/or instructions and/or commands into the emergency services provider communication device 50, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the emergency services provider communication device 50. The input device(s) 50D is/are also connected to, or linked with, the CPU 50A.

The emergency services provider communication device 50 also includes a display device 50E for displaying data and/or information to a user or operator. In the preferred embodiment, the display device 50E is also connected to, or linked with, the CPU 50A. The emergency services provider communication device 50 also includes a transmitter(s) 50F, for transmitting signals and/or data and/or information to any one or more of the personal monitoring device(s) 10, the central processing computer(s) 20, the user communication device(s) 30, the law enforcement communication device(s) 40, and/or the healthcare records computer(s) 60, and/or any other emergency services provider communication device(s) 50, which can be utilized in conjunction with the present invention. In the preferred embodiment, the transmitter(s) 50F is/are also connected to, or linked with, the CPU 50A.

The emergency services provider communication device(s) 50 also includes a receiver(s) 50G, for receiving signals and/or data and/or information from any one or more of the personal monitoring device(s) 10, the central processing computer(s) 20, the user communication device(s) 30, law enforcement communication device(s) 40, and/or the healthcare records computer(s) 60, and/or any other the emergency services provider communication device(s) 50, which can be utilized in conjunction with the present invention. In the preferred embodiment, the receiver(s) 50G is/are also connected to, or linked with, the CPU 50A.

The emergency services provider communication device 50 also includes a database(s) 50H. In the preferred embodiment, the database(s) 50H is/are also connected to, or linked with, the CPU 50A. The database(s) 50H can contain and/or include, and/or can contain and/or include a link(s) or hyperlink(s) to, and/or can be linked to or with, any of the data and/or information described herein as being stored in the database(s) 10H, 20H, 30H, and/or 40H, and/or in any of the databases of any of the healthcare records computer(s) 60, the RFID reader system(s) 80, and/or the venue/vehicle computer(s) 90, described herein, for any user or individual monitored, or to be monitored, by, with, or using, the apparatus 100 of the present invention and/or for any personal monitoring account being serviced by the apparatus 100 of the present invention. The database(s) 50H can also contain and/or include, and/or can contain and/or include a link(s) or hyperlink(s) to, and/or can be linked to or with, any of the data and/or information described herein as being stored in the database(s) 10H, 20H, 30H, and/or 40H, and/or in any of the databases of any of the healthcare records computer(s) 60, the RFID reader system(s) 80, and/or the venue/vehicle computer(s) 90, described herein, for or regarding any user or individual who or which uses a user communication device 30 to monitor another user or individual. The database(s) 50H can also contain and/or include, and/or can contain and/or include a link(s) or hyperlink(s) to, and/or can be linked to or with, any of the data and/or information described herein as being stored in the database(s) 10H, 20H, 30H, and/or 40H, and/or in any of the databases of any of the healthcare records computer(s) 60, the RFID reader system(s) 80, and/or the venue/vehicle computer(s) 90, described herein, for or regarding any user or individual who or which uses a personal monitoring device 10 to allow himself or herself to be monitored by another user or individual via the apparatus 100 and method of the present invention.

The database(s) 50H can also contain and/or include any data and/or information regarding the user or the individual, or any users or individuals, who or which utilize any user communication device 30 or any user or individual who utilizes a personal monitoring device 10, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, or any other messaging, telephone number or other address or identifier.

The database 50H can also contain and/or include any other data and/or information, and/or any software, software programs, algorithms, and/or software applications, described herein or otherwise, which are needed or desired for enabling the emergency services provider communication device 50 to perform any and/or all of the functions and/or functionality described herein as being performed by same.

The emergency services provider communication device 50 also includes an output device(s) 50I for outputting any of the data, information, and/or reports, described herein as being generated by or via the emergency services provider communication device 50. In the preferred embodiment, the output device(s) 50I can be a display screen, a speaker, a printer, a display of any type or kind, an indicator light, a transmitter, a modem, and/or any other device which can be used to output data or information of any kind or type. In the preferred embodiment, the output device(s) 50I is/are also connected to, or linked with, the CPU 50A.

The emergency services provider communication device 50 also includes a video and/or audio recording device(s) 50J which can include a camera and/or a video recording device for recording pictures or video and/or video clips and/or a microphone or an audio recording device for recording audio or audio clips which can be recorded by, and/or transmitted live, by or from the emergency services provider communication device 50, or which can be recorded by, and stored at or in, the emergency services provider communication device 50 for transmission by or from the emergency services provider communication device 50 at a later time. The video and/or audio recording device(s) 50J can be utilized to facilitate video conferencing, video chatting, and/or audio conferencing, and/or video and audio conferencing, between users of the emergency services provider communication device 50 and any user of any other computer or communication device 10, 20, 30, 40, 50, 60, 80, and/or 90, described herein. The video and/or audio recording device(s) 50J can also be utilized to facilitate one-way broadcasts from the emergency services provider communication device 50. In the preferred embodiment, the video and/or audio recording device(s) 50J is/are also connected to, or linked with, the CPU 50A.

Figure 8:
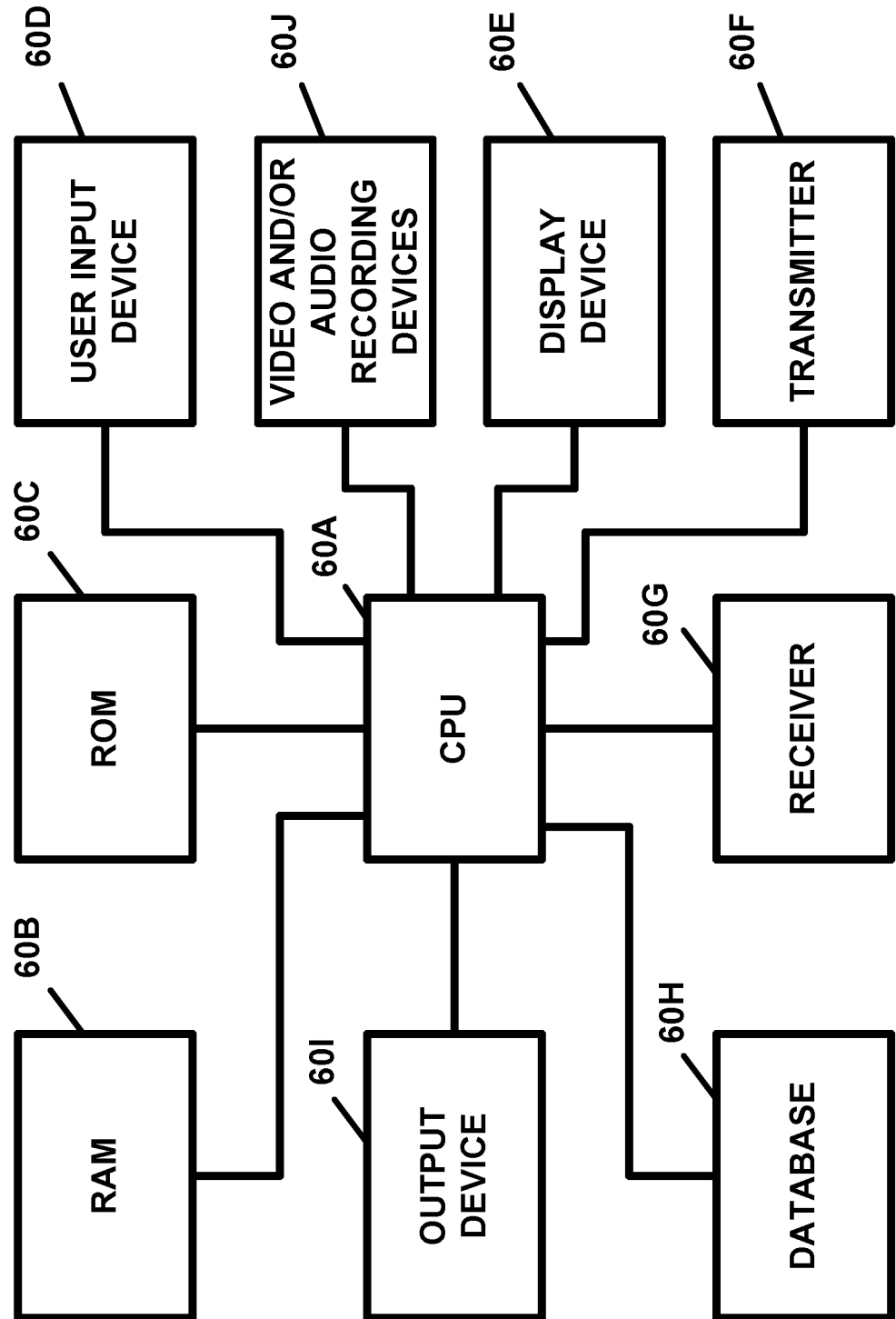
FIG. 8 illustrates the healthcare records computer of FIG. 1, in block diagram form.

FIG. 8 illustrates the healthcare records computer 60 of FIG. 1, in block diagram form. The healthcare records computer 60, in a preferred embodiment, can also be any computer or computer system, or any group of computers. The healthcare records computer 60, in the preferred embodiment, can also be a personal computer, a home computer, a laptop computer, a notebook computer, a tablet computer, a tablet, a hand-held computer, a palmtop computer, a personal communication device, a cellular telephone, a wireless telephone, a mobile telephone, a Smartphone, a smartphone, a personal digital assistant, a digital television, an interactive television, a digital television, a telephone, a digital telephone, a television, an interactive television, a beeper, a pager, and/or a watch or a Smart watch, and/or any wearable device, computer or communication device. The healthcare records computer 60 can also be server computer, or any computer capable of being utilized in a network or capable of being utilized with other computers in a network.

With reference to FIG. 8, in the preferred embodiment, the healthcare records computer 60 includes a central processing unit or CPU 60A, which in the preferred embodiment, is a microprocessor. The CPU 60A can also be a microcomputer, a minicomputer, a macro-computer, and/or a mainframe computer, depending upon the application.

The healthcare records computer 60 also includes a random access memory device(s) 60B (RAM), a read only memory device(s) 60C (ROM), each of which is connected to, or linked with, the CPU 60A, and a user input device 60D, for inputting and/or entering data and/or information and/or instructions and/or commands into the healthcare records computer 60, which can include any one or more of a keyboard, a scanner, a user pointing device, such as, for example, a mouse, a touch pad, and/or an audio input device and/or a video input device, and/or any device, electronic and/or otherwise which can be utilized for inputting and/or entering data and/or information and/or instructions and/or commands into the healthcare records computer 60. The input device(s) 60D is/are also connected to, or linked with, the CPU 60A.

The healthcare records computer 60 also includes a display device 60E for displaying data and/or information to a user or operator. In the preferred embodiment, the display device 60E is also connected to, or linked with, the CPU 60A. The healthcare records computer 60 also includes a transmitter(s) 60F, for transmitting signals and/or data and/or information to any one or more of the personal monitoring device(s) 10, the central processing computer(s) 20, the user communication device(s) 30, the law enforcement communication device(s) 40, the emergency services provider communication device(s) 50, the RFID reader system(s) 80, and/or the venue/vehicle computer(s) 90, and/or any other healthcare records computer(s) 60, which can be utilized in conjunction with the present invention. In the preferred embodiment, the transmitter(s) 60F is/are also connected to, or linked with, the CPU 60A. The healthcare records computer 60 also includes a receiver(s) 60G, for receiving signals and/or data and/or information from any one or more of the personal monitoring device(s) 10, the central processing computer(s) 20, the user communication device(s) 30, the law enforcement communication device(s) 40, the emergency services provider communication device(s) 50, the RFID reader system(s) 80, and/or the venue/vehicle computer(s) 90, and/or any other healthcare records computer(s) 60, which can be utilized in conjunction with the present invention. In the preferred embodiment, the receiver(s) 60G is/are also connected to, or linked with, the CPU 60A.

The healthcare records computer 60 also includes a database(s) 60H. In the preferred embodiment, the database(s) 60H is/are also connected to, or linked with, the CPU 60A. The database(s) 60H can contain and/or include, and/or can contain and/or include a link(s) or hyperlink(s) to, and/or can be linked to or with, any of the data and/or information described herein as being stored in the database(s) 10H, 20H, 30H, 40H, 50H, and/or in any of the databases of any of the RFID reader system(s) 80, and/or the venue/vehicle computer(s) 90, described herein, for any user or individual monitored, or to be monitored, by, with, or using, the apparatus 100 of the present invention and/or for any personal monitoring account being serviced by the apparatus 100 of the present invention. The database(s) 60H can also contain and/or include, and/or can contain and/or include a link(s) or hyperlink(s) to, and/or can be linked to or with, any of the data and/or information described herein as being stored in the database(s) 10H, 20H, 30H, 40H, 50H, and/or in any of the databases of any of the RFID reader system(s) 80, and/or the venue/vehicle computer(s) 90, described herein, for or regarding any user or individual who or which uses a user communication device 30 to monitor another user or individual. The database(s) 60H can also contain and/or include, and/or can contain and/or include a link(s) or hyperlink(s) to, and/or can be linked to or with, any of the data and/or information described herein as being stored in the database(s) 10H, 20H, 30H, 40H, 50H, and/or in any of the databases of any of the RFID reader system(s) 80, and/or the venue/vehicle computer(s) 90, described herein, for or regarding any user or individual who or which uses a personal monitoring device 10 to allow himself or herself to be monitored by another user or individual via the apparatus 100 and method of the present invention.

The database 60H can also contain and/or include, for each user or individual monitored, or to be monitored, by, with, or using, the apparatus 100 of the present invention, and for each user or individual who is monitoring, or who is to be monitoring, any other user or individual, an electronic healthcare record, an electronic medical record, an electronic dental record, a healthcare record, and/or a personal healthcare record, for the respective user or individual, which can include any data and/or information typically found in any electronic healthcare records, electronic medical records, electronic dental records, healthcare records, and/or personal healthcare records. The database 60H can also include for each user or individual, information regarding any healthcare conditions of the user or individual, any medicines, medications, or drugs, the user or individual is taking or required to take, any allergies the user or individual may have, and/or any other information which may be needed or useful for the user's or the individual's well being.

The database(s) 60H can also contain and/or include any data and/or information regarding the user or the individual, or any users or individuals, who or which utilize any user communication device 30 or any user or individual who utilizes a personal monitoring device 10, which can include, but which is not limited to, the user's or the individual's, or each user's or each individual's, name, address, telephone number(s), cellular telephone number(s), mobile or wireless telephone number(s), e-mail address or e-mail addresses, and/or text message, instant message, SMS message, or MMS message, or any other messaging, telephone number or other address or identifier.

The database 60H can also contain and/or include any other data and/or information, and/or any software, software programs, algorithms, and/or software applications, described herein or otherwise, which are needed or desired for enabling the healthcare records computer 60 to perform any and/or all of the functions and/or functionality described herein as being performed by same.

The healthcare records computer 60 also includes an output device(s) 60I for outputting any of the data, information, and/or reports, described herein as being generated by or via the healthcare records computer 60. In the preferred embodiment, the output device(s) 60I can be a display screen, a speaker, a printer, a display of any type or kind, an indicator light, a transmitter, a modem, and/or any other device which can be used to output data or information of any kind or type. In the preferred embodiment, the output device(s) 60I is/are also connected to, or linked with, the CPU 60A.

The healthcare records computer 60 also includes a video and/or audio recording device(s) 60J which can include a camera and/or a video recording device for recording pictures or video and/or video clips and/or a microphone or an audio recording device for recording audio or audio clips which can be recorded by, and/or transmitted live, by or from the healthcare records computer 60, or which can be recorded by, and stored at or in, the healthcare records computer 60 for transmission by or from the healthcare records computer 60 at a later time. The video and/or audio recording device(s) 60J can be utilized to facilitate video conferencing, video chatting, and/or audio conferencing, and/or video and audio conferencing, between users of the healthcare records computer 60 and any user of any other computer or communication device 10, 20, 30, 40, 50, 60, 80, and/or 90, described herein. The video and/or audio recording device(s) 60J can also be utilized to facilitate one-way broadcasts from the healthcare records computer

60. In the preferred embodiment, the video and/or audio recording device(s) 60J is/are also connected to, or linked with, the CPU 60A.

Figure 9:
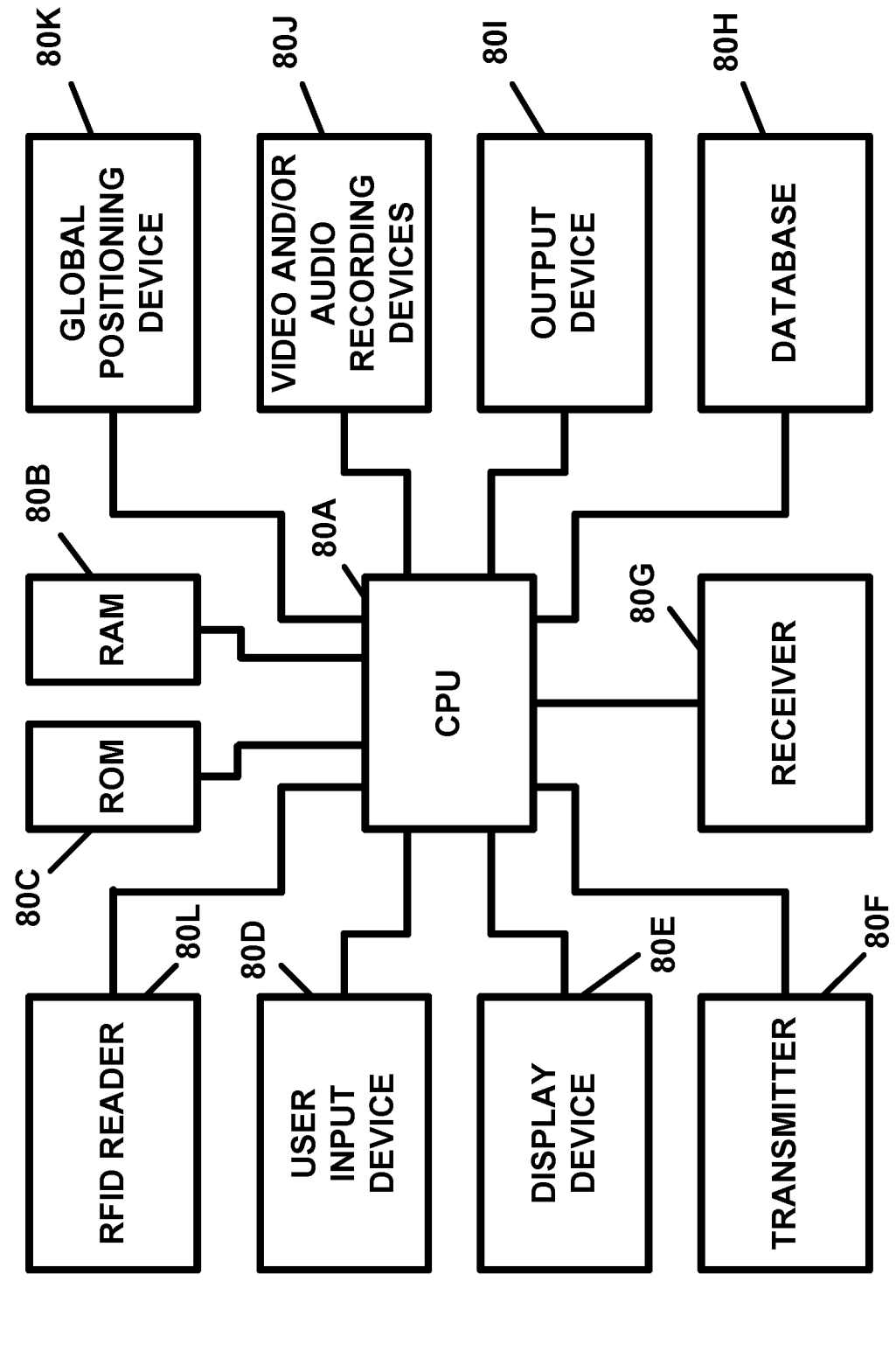
FIG. 9 illustrates the RFID reader system of FIG. 1, in block diagram form.

FIG. 9 illustrates the RFID reader system 80 of FIG. 1, in block diagram form. In a preferred embodiment, the RFID reader system 80 can include any number of RFID readers which can service any single venue or any single vehicle, or the RFID reader system 80 can include any number of RFID readers which can service any number of venues and/or any number of vehicles. With reference to FIG. 9, in the preferred embodiment, the RFID reader system 80 includes a central processing unit or CPU 80A which, in the preferred embodiment, is a microprocessor. The CPU 90A may also be a microcomputer, a minicomputer, a macro-computer, and/or a mainframe computer, depending upon the application. The CPU 80A is specially programmed and/or specially configured to perform any and/or all of the functionality described herein as being performed by the RFID reader system 80.

The RFID reader system 80 also includes a random access memory (RAM) device(s) 80B and a read only (ROM) memory device(s) 80C, each of which is connected to the CPU 80A, and a user input device(s) 80D, for entering data or information and/or instructions and/or commands into the RFID reader system 80. The user input device(s) 80D can be or can include any one or more of a keyboard, a touch screen keyboard, a scanner, a user pointing device, such as, for example, a mouse, an audio input device, a microphone, a camera, a video recording device, a touch pad, or a touch screen, or any other device or component for allowing data, information, or instructions and/or commands, to be entered into the RFID reader system 80. The user input device(s) 80D is/are also connected to the CPU 80A.

The RFID reader system 80 also includes a display device 80E for displaying data and/or information to a user. The RFID reader system 80 also includes a transmitter 80F, for transmitting signals and/or data and/or information to any one or more of the personal monitoring device(s) 10, the central processing computer(s) 20, the user communication device(s) 30, the law enforcement communication device(s) 40, the emergency services provider communication device(s) 50, and/or the venue/vehicle computer(s) 90, or to any of the other RFID reader systems 80. The RFID reader system 80 also includes a receiver 80G, for receiving signals and/or data and/or information from any one or more of the personal monitoring device(s) 10, the central processing computer(s) 20, the user communication device(s) 30, the law enforcement communication device(s) 40, the emergency services provider communication device(s) 50, and/or the venue/vehicle computer(s) 90, or from any of the other RFID reader systems 80.

The RFID reader system 80 also includes a database(s) 80H. The database(s) 80H can contain and/or be linked to any of the data and/or information described herein as being stored in the database 20H. The database(s) 80H can also contain and/or include any data and/or information regarding any RFID tags 70 which are, which have been, or which are to be read, by the RFID reader system 80, the venue or vehicle in or for which the RFID tags 70 can be used and the RFID readers (denoted by the reference numeral 80L) which can be used to read or scan the RFID tags 70. The database(s) 80H can also contain and/or include information regarding the RFID readers 80L, the manufacturer of same, the model number of same, and the RFID tags 70 which can be read or scanned by the same.

The database(s) 80H can also contain and/or include, for each RFID reader 80L utilized in the RFID reader system 80, information regarding the respective venue or the respective vehicle in or for which the RFID reader 80L is deployed, assigned, or utilized, and information regarding the respective entrance, exit, door, doorway, gateway, or other means by which an individual using a personal monitoring device 10 can enter and/or exit the respective venue or the respective vehicle, to which the RFID reader 80L is assigned.

The database(s) 80H can also contain and/or include, for each RFID reader 80L, any position or location information regarding the same, information regarding the RFID reader's 80L position or location in or on the respective venue or the respective vehicle, latitude information or latitude of the RFID reader 80L, longitude information or longitude of the RFID reader 80L, and/or any other information regarding the RFID reader 80L including manufacturer information, model number, serial number, whether the RFID reader 80L is a passive RFID tag reader or an active RFID tag reader, and/or any other data and/or information deemed needed, required, or desired, for allowing the RFID reader system 80 to perform all of the functions and functionalities described herein as being performed by the RFID reader system 80 and/or the central processing computer 20, and/or the apparatus 100 of the present invention.

The database 40H can also contain and/or include any data and/or information described herein as being contained and/or included in any of the herein-described and respective databases 10H, 20H, 30, 40H, 50H, 60H, and/or 80H of any other RFID reader systems 80. and/or any databases of and for any of the venue/vehicle computer(s) 90, described herein as being utilized in connection, and/or in conjunction with, the apparatus 100 of the present invention.

The database 80H can also contain and/or include any data and/or information which may be required, and/or which may be desired, for performing any of the functionality and/or processing routines described herein as being performed by the RFID reader system 80 and/or the apparatus 100. The database 80H can also be connected to the CPU 80A.

The RFID reader system 80 also includes an output device(s) 80I for outputting any of the data and/or information described herein as being generated by or via the RFID reader system 80. In the preferred embodiment, the output device(s) 80I can be a printer, a display, a transmitter, a modem, and/or any other device which can be used to output data or information of any kind or type. The output device(s) 80I can also be connected to the CPU 80A.

The RFID reader system 80 can also include a video and/or audio recording device(s) 80J which can include a camera and/or a video recording device for recording pictures or video and/or video clips and/or a microphone or an audio recording device for recording audio or audio clips which can be recorded by, and/or transmitted live, by or from the RFID reader system 80, or which can be recorded by, and stored at or in, the RFID reader system 80 for transmission by or from the RFID reader system 80 at a later time. The video and/or audio recording device(s) 80J can also be utilized to facilitate one-way broadcasts from the RFID reader system 80, and/or can be utilized to facilitate video conferencing, video chatting, and/or audio conferencing, and/or video and audio conferencing, between any of the herein-described users, individuals, parties, or entities, who or which utilize the apparatus 100 and method of the present invention. In this regard, the video and/or audio recording device(s) 80J can be utilized to facilitate video conferencing, video chatting, and/or audio conferencing, and/or video and audio conferencing, between users of the RFID reader system 80 and any user of any other computer or communication device 10, 20, 30, 40, 50, 60, 80, and/or 90, described herein. The video and/or audio recording device(s) 80J can also be utilized to facilitate one-way broadcasts from the RFID reader system 80. In a preferred embodiment, the user or operator of the RFID reader system 80 can also engage in telephone calls and video conferencing calls via the same. The user or operator of the RFID reader system 80 can also use the video and/or audio recording device(s) 80J to record and broadcast or transmit content via its transmitter 80F. The video and/or audio recording device(s) 80J can also be connected to the CPU 80A.

With reference to FIG. 9, the RFID reader system 80, in the preferred embodiment, also includes a global positioning device 80K for determining the position or location of the RFID reader system 80. The global positioning device 80K can also be connected to the CPU 80A.

With reference to FIG. 9, the RFID reader system 80, in the preferred embodiment, can also include an RFID reader 80L, or any number of RFID readers 80L which can be any commercially available RFID reader device which can be suitable for use with the kind or type of RFID reader system 80 and RFID tags 70 which are utilized in connection with the apparatus 100 of the present invention. The RFID reader 80L can be any suitable and commercially available RFID reader which can be integrated with the respective RFID reader system 80, can be integrated into a case or other housing of and/or for the respective RFID reader system 80, or can be located externally from and/or can be wirelessly linked to or with, the respective RFID reader system 80 and/or the CPU 80A of same, such as by using any suitable wireless communication technology and/or a Bluetooth communication link. In such an embodiment, the RFID reader system 80 can be programmed with or equipped with any suitable hardware and software programs or software applications ("apps") needed or desired for enabling the RFID reader system 80 and the RFID reader(s) 80L to communicate with each other and work together to provide the respective RFID reader system 80 with all necessary or desired RFID reading capabilities and functionalities.

In a preferred embodiment, any number of RFID readers 80L can be utilized to service any single venue or any single vehicle. In a preferred embodiment, each RFID reader 80L can be stationed or positioned at, or adjacent to, a particular entrance, exit, door, doorway, and/or gateway, of, or any other entrance or exit means, of a respective vehicle or a respective vehicle, by or via which an individual, using a personal monitoring device 10, can enter and/or exit the respective venue or the respective vehicle.

Figure 10:
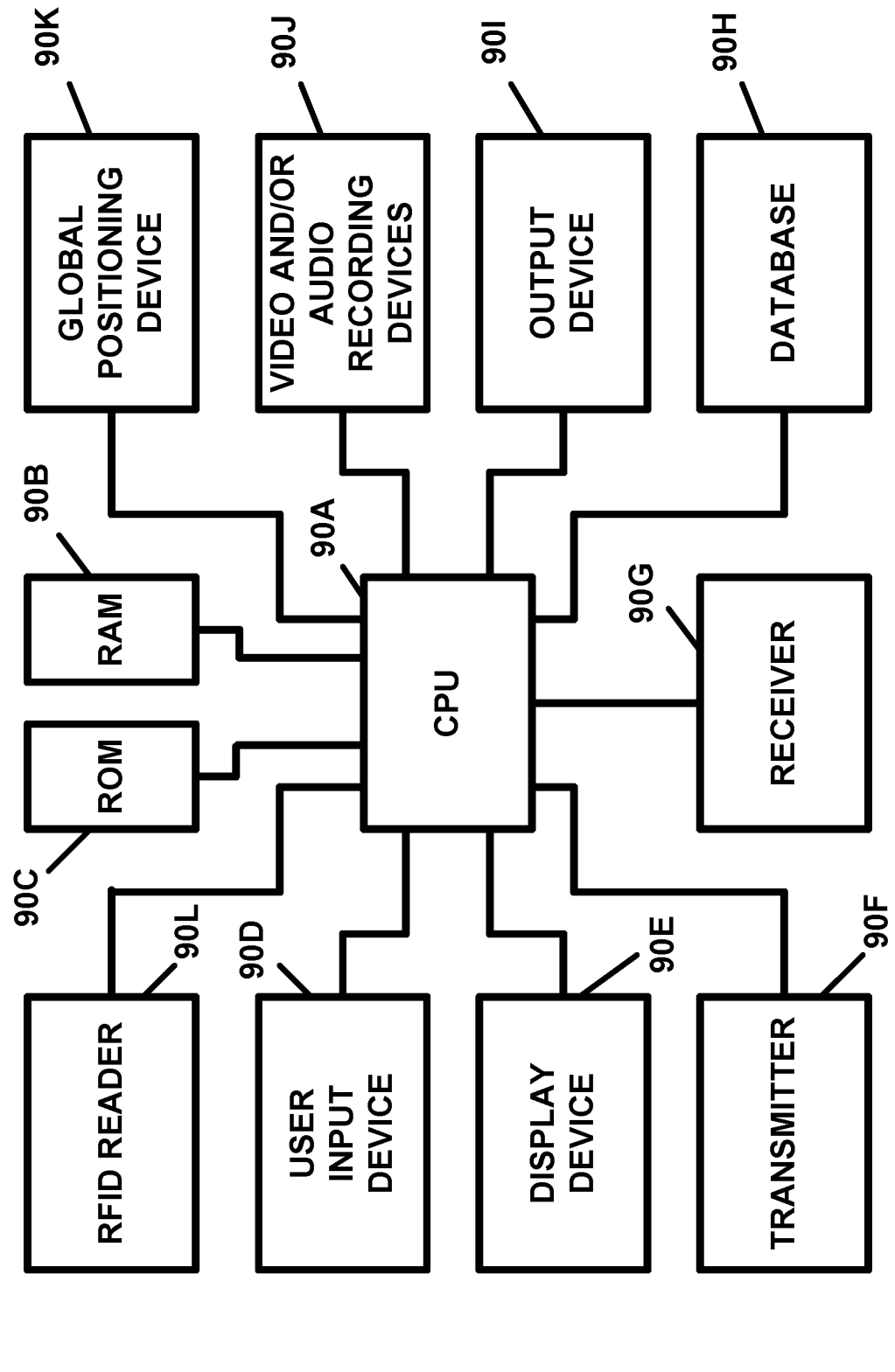
FIG. 10 illustrates the venue/vehicle computer of FIG. 1, in block diagram form.

FIG. 10 illustrates the venue/vehicle computer 90 of FIG. 1, in block diagram form. With reference to FIG. 10, in the preferred embodiment, the venue/vehicle computer 90 includes a central processing unit or CPU 90A which, in the preferred embodiment, is a microprocessor. The CPU 90A may also be a microcomputer, a minicomputer, a macro-computer, and/or a mainframe computer, depending upon the application. The CPU 90A is specially programmed and/or specially configured to perform any and/or all of the functionality described herein as being performed by the venue/vehicle computer 90. In a preferred embodiment, each venue/vehicle computer 90 can be associated with, assigned to, and/or deployed at, on, or in, any respective venue or any respective vehicle.

The venue/vehicle computer 90 also includes a random access memory (RAM) device(s) 90B and a read only (ROM) memory device(s) 90C, each of which is connected to the CPU 90A, and a user input device(s) 90D, for entering data or information and/or instructions and/or commands into the venue/vehicle computer 90. The user input device(s) 90D can be or can include any one or more of a keyboard, a touch screen keyboard, a scanner, a user pointing device, such as, for example, a mouse, an audio input device, a microphone, a camera, a video recording device, a touch pad, or a touch screen, or any other device or component for allowing data, information, or instructions and/or commands, to be entered into the venue/vehicle computer 90. The user input device(s) 90D is/are also connected to the CPU 90A.

The venue/vehicle computer 90 also includes a display device 90E for displaying data and/or information to a user. The venue/vehicle computer 90 also includes a transmitter 90F, for transmitting signals and/or data and/or information to any one or more of the personal monitoring device(s) 10, the central processing computer(s) 20, the user communication device(s) 30, the law enforcement communication device(s) 40, the emergency services provider communication device(s) 50, the healthcare records computers 60, and/or RFID reader systems 80, and/or to any other venue/vehicle computer(s) 90. The venue/vehicle computer 90 also includes a receiver 90G, for receiving signals and/or data and/or information from any one or more of the personal monitoring device(s) 10, the central processing computer(s) 20, the user communication device(s) 30, the law enforcement communication device(s) 40, the emergency services provider communication device(s) 50, the healthcare records computers 60, and/or RFID reader systems 80, and/or to any other venue/vehicle computer(s) 90.

The venue/vehicle computer 90 also includes a database (s) 90H. The database 90H can contain and/or be linked to any of the data and/or information described herein as being stored in the databases 10H, 20H, 30H, 40H, 50H, 60H, and/or 80H, described herein. The database 90H can also contain and/or include any data and/or information regarding the respective venue or the respective vehicle associated with the respective venue/vehicle computer 90, and/or data and/or information regarding the name, address, telephone number, email address, text, SMS, or instant messaging, number, website address, url, and/or any other identifying and/or contact information for the respective venue or the respective vehicle. The database 90H can also contain and/or include, for the respective venue or the respective vehicle associated with the respective venue/vehicle computer 90, and/or a calendar, a calendar of events, a schedule, and/or an itinerary, of or for each respective venue and/or of or for each respective vehicle. The database 90H can also contain and/or include data and/or information regarding any and/or all RFID reader systems 80 and/or any and/or all RFID readers 80L associated with same, which are assigned to, and/or deployed at, on, or in, the respective venue and/or the respective vehicle which is associated. The database 90H can also contain and/or include data and/or information regarding each RFID reader 80L and/or RFID reader 90L (shown in FIG. 10) which is utilized in, on, or at, the respective venue or the respective vehicle and information regarding where each RFID reader 80L and/or RFID reader 90L is located in, on, or at, the respective venue or the respective vehicle, including, but not limited to, information regarding each respective entrance, exit, door, doorway, gateway, or other means by which an individual using a personal monitoring device 10 can enter and/or exit the respective venue or the respective vehicle, to which, or adjacent to which, each respective RFID reader 80L and/or RFID reader 90L is assigned and/or deployed.

The database(s) 90H can also contain and/or include any data and/or information needed or desired for performing all of the functions and/or functionalities described herein as being performed by the venue/vehicle computer 90 and/or the apparatus 100 of the present invention. The database 90H can also be connected to the CPU 90A.

The venue/vehicle computer 90 also includes an output device(s) 90I for outputting any of the data and/or information described herein as being generated by or via the venue/vehicle computer 90. In the preferred embodiment, the output device(s) 90I can be a printer, a display, a transmitter, a modem, and/or any other device which can be used to output data or information of any kind or type. The output device(s) 90I can also be connected to the CPU 90A.

The venue/vehicle computer 90 can also include a video and/or audio recording device(s) 90J which can include a camera and/or a video recording device for recording pictures or video and/or video clips and/or a microphone or an audio recording device for recording audio or audio clips which can be recorded by, and/or transmitted live, by or from the venue/vehicle computer 90, or which can be recorded by, and stored at or in, the venue/vehicle computer 90 for transmission by or from the venue/vehicle computer 90 at a later time. The video and/or audio recording device(s) 90J can also be utilized to facilitate one-way broadcasts from the venue/vehicle computer 90, and/or can be utilized to facilitate video conferencing, video chatting, and/or audio conferencing, and/or video and audio conferencing, between any of the herein-described users, individuals, parties, or entities, who or which utilize the apparatus 100 and method of the present invention. In a preferred embodiment, the video and/or audio recording device(s) 90J can be utilized to facilitate video conferencing, video chatting, and/or audio conferencing, and/or video and audio conferencing, between users of the venue/vehicle computer 90 and any user of any other computer or communication device 10, 20, 30, 40, 50, 60, 80, and/or 90, described herein. In this regard, the user or operator of the venue/vehicle computer 90 can engage in telephone calls and video conferencing calls via the same. The user or operator of the venue/vehicle computer 90 can also use the video and/or audio recording device(s) 90J to record and broadcast or transmit content via its transmitter 90F. The video and/or audio recording device(s) 90J can also be connected to the CPU 90A.

With reference to FIG. 10, the venue/vehicle computer 90, in the preferred embodiment, also includes a global positioning device 90K for determining the position or location of the venue/vehicle computer 90. The global positioning device 90K can also be connected to the CPU 90A.

With reference once again to FIG. 10, the venue/vehicle computer 90, in the preferred embodiment, can also include one or more RFID readers 90L, or one or more of the RFID readers 80L, described herein, which can be any commercially available RFID reader of RFID reader device(s) which can be suitable for use with the kind or type of venue or vehicle which is utilized, which can be suitable for the venue/vehicle computer 90 which is utilized, and/or which can be suitable for the particular RFID reading functionality required at the respective venue or the respective vehicle. In a preferred embodiment, one or more RFID readers 90L, or RFID readers 80L, can be stationed at, or positioned at, a respective entrance, exit, door, doorway, gateway, or other means by which an individual using a personal monitoring device 10 can enter and/or exit the respective venue or the respective vehicle. In this manner, the RFID reader(s) 90L can read or scan a respective RFID tag(s) 70 which are attached to or affixed to, or which are placed on or inside, the respective personal monitoring device 10 being used by the individual as they enter and/or exit the respective venue or the respective vehicle. In a preferred embodiment, the RFID readers 90L can be, or can include, any of the herein-described RFID readers 80L of any of the herein-described RFID reader systems 80. In this regard, in a preferred embodiment, the RFID readers 90L and the RFID readers 80L can be the same RFID readers, and can be utilized in any RFID reader system 80, and/or in or with any venue/vehicle computer 90, described herein.

In a preferred embodiment, the apparatus 100 and method of the present invention can be utilized to monitor an individual or individuals of any age. In this regard, the apparatus 100 and/or the personal monitoring device 10 can be utilized to monitor any child, infant, teenager or young adult, adult of any age, and/or elderly individual. In a preferred embodiment, the apparatus 100 and/or the personal monitoring device 10 can also be utilized to monitor any child, infant, teenager or young adult, adult of any age, and/or elderly individual, who may or may not be inflicted with a condition, illness, or disease, or who may or may not be inflicted with autism, Alzheimer's disease, memory loss, or be ill with any temporary or permanent illness, sickness, disease, or condition. In a preferred embodiment, the apparatus 100 and/or the personal monitoring device 10 can also be utilized to monitor any child, infant, teenager or young adult, adult of any age, and/or elderly individual, as a safety precaution.

In a preferred embodiment, any user or individual who utilizes a personal monitoring device 10, or who has a personal monitoring device 10 assigned to him or her, or who has a personal monitoring device 10 associated with him or her, can be referred to herein, or can be defined herein as being, a "monitored individual". In a preferred embodiment, any user or individual who utilizes a user communication device 30 to monitor a monitored individual can be referred to herein, or can be defined herein as being, a "monitoring individual".

In a preferred embodiment, it is envisioned that a personal monitoring device 10 can be programmed with, or can have stored therein or therewith, information regarding the monitored individual's home address, residence address, school residence address or place, workplace address, or other address, place, or location, which is considered to be that monitored individual's place of safety or "home base" or "safe location". In a preferred embodiment, it is envisioned that the personal monitoring device 10 can be programmed with, or can have stored therein or therewith, information regarding any address(es), place(s), or location(s), to which the monitored individual typically travels on a daily basis. For example, the personal monitoring device 10 can be programmed with, or can have stored therein or therewith, information regarding the monitored individual's school address, place, or location, workplace address, place, or location, employment address, place, or location, activity or event address, place, or location, or any other address, place, or location, to which the monitored individual is known to travel on a weekday basis, on a weekend daily basis, or on any daily basis.

In a preferred embodiment, the personal monitoring device 10 can also be programmed with the monitored individual's travel itineraries and/or travel schedules for traveling to and between one address, place, or location to another address, place, or location. In a preferred embodiment, the personal monitoring device 10 can also be programmed with travel routes or directions for traveling to and between one address, place, or location to another address, place, or location. In a preferred embodiment, the personal monitoring device 10 can also be programmed with software programs, navigation programs, or any algorithms or software applications, for identifying, determining, ascertaining, or calculating, any travel routes or directions for traveling to and between one address, place, or location to another address, place, or location.

In a preferred embodiment, the personal monitoring device 10 can be utilized in connection with, or in conjunction with, the RFID tags 70 in order to detect and/or to ascertain when the monitored individual enters into or onto, and/or exits from, any venue or any vehicle, and/or to detect and/or to ascertain when the monitored individual enters into or onto, and/or exits from, any venue or any vehicle during his or her daily activities and/or daily travels, regardless of whether or not the monitored individual is traveling in accordance with his or her travel itinerary or schedule.

In a preferred embodiment, the personal monitoring device 10 can also be utilized in connection with, or in conjunction with, the apparatus 100, the central processing computer 20, a user communication device 30 associated with, or used by, any user or individual authorized to, or assigned to, monitor the monitored individual, any law enforcement communication device 40, and/or any emergency services provider communication device 50. In another preferred embodiment, the personal monitoring device 10 can also be utilized as a stand-alone device by the monitored individual to allow the monitored individual to monitor his or her travels, whereabouts, or environment.

In a preferred embodiment, the personal monitoring device 10 can also be utilized to record, and/or to report on, the travels and/or travel history of or for a monitored individual for any given period of time. In a preferred embodiment, the personal monitoring device 10 and/or the central processing computer 20 can also utilize artificial intelligence (AI) and/or machine learning algorithms and/or programs in order to modify the stored or expected travel itinerary or schedule of a monitored individual.

In a preferred embodiment, the apparatus 100 and method of the present invention can be utilized in order to monitor a monitored individual's entry into or onto, and/or exit from, a respective venue or a respective vehicle. In particular, the apparatus 100 of the present invention can be utilized, in a preferred embodiment, in order to detect and/or to ascertain, and/or to report and/or to provide notification, to an authorized user or to a monitoring individual, regarding when a monitored individual enters into or onto, and/or exits from, a venue, and/or enters into or onto, or exits from, a vehicle during the course of their daily activities and/or travels. In a preferred embodiment, the respective venue or vehicle can be equipped with an RFID reader(s) 80L of a respective RFID reader system 80, or an RFID reader(s) 90L of a respective venue/vehicle computer 90. In a preferred embodiment, an RFID reader 80L or an RFID reader 90L can be positioned at, or can be stationed at, a respective door, doorway, gate, or gateway, for each door, doorway, gate, or gateway, which serves as an entry point into, or exit point from, the respective venue or the respective vehicle.

In a preferred embodiment, each time a monitored individual enters into or onto the respective venue or into or onto the respective vehicle, the RFID tag 70, of or associated with the monitored individual's personal monitoring device 10, can be read by the respective RFID reader 80L or RFID reader 90L which is positioned at the respective door, doorway, gate, or gateway, of the respective venue or the respective vehicle through which the monitored individual enters the same. In a preferred embodiment, the detection of the RFID tag 70 can be reported, by and/or from the RFID reader system 80 or the venue/vehicle computer 90, associated with the respective RFID reader 80L or RFID reader 90L, to the central processing computer 20, to the user communication device 30, and/or to the personal monitoring device 10, via a transmission of an appropriate signal from the respective RFID reader system 80 or the respective venue/vehicle computer 90 to the central processing computer 20, to the user communication device 30, and/or to the personal monitoring device 10. Thereafter, in a preferred embodiment, the respective reader system 80 or the respective venue/vehicle computer 90, and/or the central processing computer 20, can generate an entry notification message and/or an entry alert message which can contain and/or can include information identifying the monitoring individual, information regarding the date and time when the monitoring individual entered into or onto the respective venue or entered into or onto the respective vehicle, and/or information identifying the respective venue or the respective vehicle. In another preferred embodiment, the personal monitoring device 10 can also generate the herein-described entry notification message and/or entry alert message.

In a preferred embodiment, in the case of the monitored individual entering into or onto a venue, the entry notification message and/or entry alert message can contain and/or can include information regarding the address of the venue and a contact individual and contact telephone number for the venue. In a preferred embodiment, in the case of the monitored individual entering into or onto a vehicle, the entry notification message and/or entry alert message can contain and/or can include information for identifying the vehicle, identifying the type of vehicle (such as, for example, a private car or vehicle, a car service vehicle, a ride-sharing vehicle (such as an Uber vehicle or a LYFT vehicle), a mass transportation vehicle, a bus, a train, a subway train, a boat of any type, kind or size, or an aircraft or helicopter of any type, kind, or size), and/or make and model information and/or vehicle identification information for the vehicle, information regarding the vehicle operator, and/or contact information for the vehicle and/or the vehicle operator and/or a telephone number for the vehicle owner or the vehicle operator. In a preferred embodiment, in the case of the monitored individual entering into or onto a vehicle, the entry notification message and/or entry alert message can also contain and/or can include information regarding the position or location of the vehicle at the time the monitored individual enters into to onto the vehicle. In a preferred embodiment, the position or location of the vehicle can be determined and/or ascertained by the global positioning device 90K of the venue/vehicle computer 90 associated with the respective venue or the respective vehicle.

In a preferred embodiment, the respective reader system 80 or the respective venue/vehicle computer 90, and/or the central processing computer 20, can transmit the entry notification message and/or the entry alert message to the user communication device 30 which is used by, associated with, or assigned to, the monitoring individual for the monitored individual. In a preferred embodiment, for example, the monitoring individual can be a parent, a grandparent, a sibling, a relative, a friend, a guardian, or any other authorized person. In a situation where the monitored individual may be monitored by more than one monitoring individual, then the respective reader system 80 or the respective venue/vehicle computer 90, and/or the central processing computer 20, can transmit the entry notification message and/or the entry alert message to the user communication device 30 which is used by, associated with, or assigned to, each such monitoring individual. In a preferred embodiment, the respective reader system 80 and/or the central processing computer 20 can also transmit the entry notification message and/or the entry alert message to any law enforcement communication device(s) 40 and/or to any emergency services provider communication device(s) 50, if needed or desired. In another preferred embodiment, the personal monitoring device 10 can transmit the entry notification message and/or the entry alert message to the user communication device(s) 30 which is used by, associated with, or assigned to, the monitoring individual(s) for the monitored individual, and/or to any law enforcement communication device(s) 40, and/or to any emergency services provider communication device(s) 50, if needed or desired.

In a preferred embodiment, any data and/or information contained in the entry notification message and/or the entry alert message can be stored in a travel log or travel history for the monitored individual, which travel log or travel history can be stored in any of the databases 10H, 20H, 30H, 40H, and/or 50H, of the respective devices, computers, or communications devices described herein.

In a preferred embodiment, each time a monitored individual exits from the respective venue or from the respective vehicle, the RFID tag 70, of or associated with the monitored individual's personal monitoring device 10, can be read by the respective RFID reader 80L or RFID reader 90L which is positioned at the respective door, doorway, gate, or gateway, of the respective venue or the respective vehicle through which the monitored individual exits the same. In a preferred embodiment, the detection of the RFID tag 70 can be reported, by and/or from the RFID reader system 80 or the venue/vehicle computer 90, associated with the respective RFID reader 80L or RFID reader 90L, to the central processing computer 20, to the user communication device 30, and/or to the personal monitoring device 10, via a transmission of an appropriate signal from the respective RFID reader system 80 or the respective venue/vehicle computer 90 to the central processing computer 20, to the user communication device 30, and/or to the personal monitoring device 10. Thereafter, in a preferred embodiment, the respective reader system 80 or the respective venue/vehicle computer 90, and/or the central processing computer 20, can generate an exit notification message and/or an exit alert message which can contain and/or can include information identifying the monitoring individual, information regarding the date and time when the monitoring individual exited from the respective venue or exited from the respective vehicle, and/or information identifying the respective venue or the respective vehicle. In another preferred embodiment, the personal monitoring device 10 can also generate the herein-described exit notification message and/or exit alert message.

In a preferred embodiment, in the case of the monitored individual exiting from a venue, the exit notification message and/or exit alert message can contain and/or can include information regarding the address of the venue and a contact individual and contact telephone number for the venue. In a preferred embodiment, in the case of the monitored individual exiting from a vehicle, the exit notification message and/or exit alert message can contain and/or can include information for identifying the vehicle, identifying the type of vehicle (such as, for example, a private car or vehicle, a car service vehicle, a ride-sharing vehicle (such as an Uber vehicle or a LYFT vehicle), a mass transportation vehicle, a bus, a train, a subway train, a boat of any type, kind or size, or an aircraft or helicopter of any type, kind, or size), and/or make and model information and/or vehicle identification information for the vehicle, information regarding the vehicle operator, and/or contact information for the vehicle and/or the vehicle operator and/or a telephone number for the vehicle owner or the vehicle operator. In a preferred embodiment, in the case of the monitored individual exiting from a vehicle, the exit notification message and/or exit alert message can also contain and/or can include information regarding the position or location of the vehicle at the time the monitored individual exited from the vehicle. In a preferred embodiment, the position or location of the vehicle can be determined and/or ascertained by the global positioning device 90K of the venue/vehicle computer 90 associated with the respective venue or the respective vehicle.

In a preferred embodiment, the respective reader system 80 or the respective venue/vehicle computer 90, and/or the central processing computer 20, can transmit the exit notification message and/or the exit alert message to the user communication device 30 which is used by, associated with, or assigned to, the monitoring individual for the monitored individual. In a situation where the monitored individual may be monitored by more than one monitoring individual, then the respective reader system 80 or the respective venue/vehicle computer 90, and/or the central processing computer 20, can transmit the exit notification message and/or the exit alert message to the user communication device 30 which is used by, associated with, or assigned to, each such monitoring individual. In a preferred embodiment, the respective reader system 80 or the respective venue/vehicle computer 90, and/or the central processing computer 20, can also transmit the exit notification message and/or the exit alert message to any law enforcement communication device(s) 40 and/or to any emergency services provider communication device(s) 50, if needed or desired. In another preferred embodiment, the personal monitoring device 10 can transmit the exit notification message and/or the exit alert message to the user communication device(s) 30 which is used by, associated with, or assigned to, the monitoring individual(s) for the monitored individual, and/or to any law enforcement communication device(s) 40, and/or to any emergency services provider communication device(s) 50, if needed or desired.

In a preferred embodiment, any data and/or information contained in the exit notification message and/or the exit alert message can be stored in a travel log or travel history of or for the monitored individual, which travel log or travel history can be stored in any of the databases 10H, 20H, 30H, 40H, and/or 50H, of the respective devices, computers, or communications devices described herein.

In a preferred embodiment, at any time, the monitoring individual can utilize the user communication device 30 in order to access the central processing computer 20 in order to monitor the position or location of the personal monitoring device 10 and the monitored individual via the central processing computer 20. In a preferred embodiment, at any time, the monitoring individual can also utilize the user communication device 30 to communicate with the personal monitoring device 10 and the monitored individual. In a preferred embodiment, at any time, any user or operator of any law enforcement communication device(s) 40 and/or of any emergency services provider communication device(s) 50 can also utilize the same in order to monitor the position or location of the personal monitoring device 10 and the monitored individual via the central processing computer 20 and/or in order to communicate with the personal monitoring device 10 and the monitored individual and/or to communicate with any authorized user of any user communication device 30 used to monitor the monitored individual.

Figure 11:
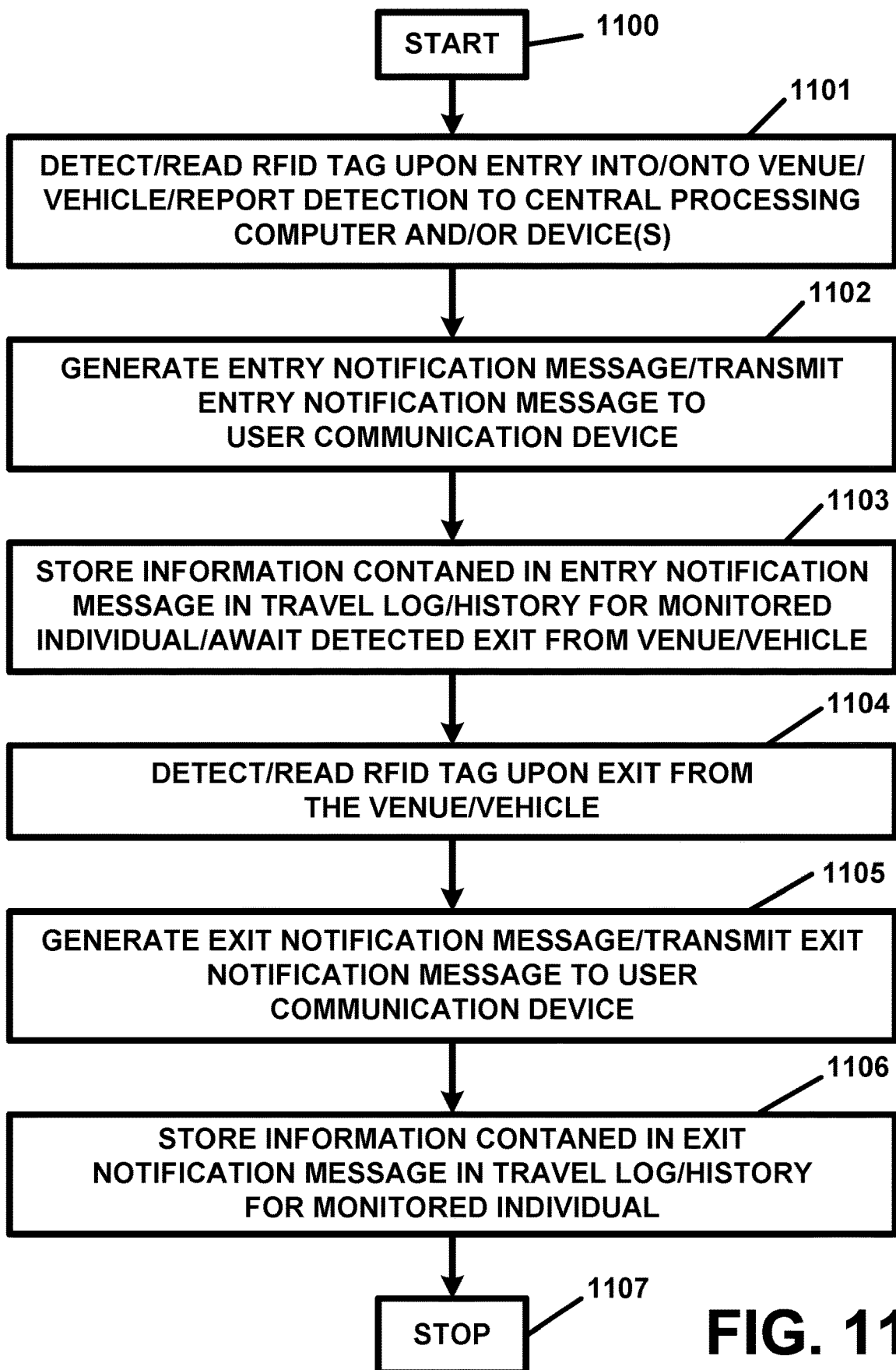
FIG. 11 illustrates a preferred embodiment method for utilizing the apparatus of the present invention, in flow diagram form.

FIG. 11 illustrates a preferred embodiment method for utilizing the apparatus 100 and method of the present invention in order to monitor a monitored individual, in flow diagram form. In particular, the apparatus 100 of the preferred embodiment of FIG. 11 can be utilized in order to detect and/or to ascertain, and/or to report and/or to provide notification, to an authorized user or to a monitoring individual, regarding when a monitored individual enters into or onto, and/or exits from, a venue, and/or enters into or onto, or exits from, a vehicle during the course of their daily activities and/or travels. As noted herein, in a preferred embodiment, the respective venue or vehicle can be equipped with an RFID reader(s) 80L of a respective RFID reader system 80, or an RFID reader(s) 90L of a respective venue/vehicle computer 90. In a preferred embodiment, an RFID reader 80L or an RFID reader 90L can be positioned at, or can be stationed at, a respective door, doorway, gate, or gateway, for each door, doorway, gate, or gateway, which serves as an entry point into, or exit point from, the respective venue or the respective vehicle.

With reference to FIG. 11, the operation of the apparatus 100 commences at step 1100. At step 1101, when the monitored individual enters into or onto the respective venue or into or onto the respective vehicle, the RFID tag 70, of or associated with the monitored individual's personal monitoring device 10, can be detected and/or read by the respective RFID reader 80L or RFID reader 90L which is positioned at the respective door, doorway, gate, or gateway, of the respective venue or the respective vehicle through which the monitored individual enters. At step 1101, the detection of the RFID tag 70 can be reported, by and/or from the RFID reader system 80 or the venue/vehicle computer 90, associated with the respective RFID reader 80L or RFID reader 90L, to the central processing computer 20, to the user communication device 30, and/or to the personal monitoring device 10, via a transmission of an appropriate signal from the respective RFID reader system 80 or the respective venue/vehicle computer 90 to the central processing computer 20, to the user communication device 30, and/or to the personal monitoring device 10.

Thereafter, at step 1102, the respective reader system 80 or the respective venue/vehicle computer 90, and/or the central processing computer 20, can generate an entry notification message and/or an entry alert message which can contain and/or can include information identifying the monitoring individual, information regarding the date and time when the monitoring individual entered into or onto the respective venue or entered into or onto the respective vehicle, and/or information identifying the respective venue or the respective vehicle. In another preferred embodiment, at step 1102, the personal monitoring device 10 can also generate the herein-described entry notification message and/or entry alert message.

In a preferred embodiment, in the case of the monitored individual entering into or onto a venue, the entry notification message and/or entry alert message can contain and/or can include information regarding the address of the venue and a contact individual and contact telephone number for the venue. In a preferred embodiment, in the case of the monitored individual entering into or onto a vehicle, the entry notification message and/or entry alert message can contain and/or can include information for identifying the vehicle, identifying the type of vehicle (such as, for example, a private car or vehicle, a car service vehicle, a ride-sharing vehicle (such as an Uber vehicle or a LYFT vehicle), a mass transportation vehicle, a bus, a train, a subway train, a boat of any type, kind or size, or an aircraft or helicopter of any type, kind, or size), and/or make and model information and/or vehicle identification information for the vehicle, information regarding the vehicle operator, and/or contact information for the vehicle and/or the vehicle operator and/or a telephone number for the vehicle owner or the vehicle operator. In a preferred embodiment, in the case of the monitored individual entering into or onto a vehicle, the entry notification message and/or entry alert message can also contain and/or can include information regarding the position or location of the vehicle at the time the monitored individual enters into to onto the vehicle. In a preferred embodiment, the position or location of the vehicle can be determined and/or ascertained by the global positioning device 90K of the venue/vehicle computer 90 associated with the respective venue or the respective vehicle.

At step 1102, the respective reader system 80 or the respective venue/vehicle computer 90, and/or the central processing computer 20, can transmit the entry notification message and/or the entry alert message to the user communication device 30 which is used by, associated with, or assigned to, the monitoring individual for the monitored individual. In a preferred embodiment, for example, the monitoring individual can be a parent, a grandparent, a sibling, a relative, a friend, a guardian, or any other authorized person. In a situation where the monitored individual may be monitored by more than one monitoring individual, then the respective reader system 80 or the respective venue/vehicle computer 90, and/or the central processing computer 20, at step 1102, can transmit the entry notification message and/or the entry alert message to the user communication device 30 which is used by, associated with, or assigned to, each such monitoring individual.

In a preferred embodiment, the respective reader system 80 or the respective venue/vehicle computer 90, and/or the central processing computer 20, can also, at step 1102, transmit the entry notification message and/or the entry alert message to any law enforcement communication device(s) 40 and/or to any emergency services provider communication device(s) 50, if needed or desired. In another preferred embodiment, the personal monitoring device 10, at step 1102, can also transmit the entry notification message and/or the entry alert message to the user communication device(s) 30 which is used by, associated with, or assigned to, the monitoring individual(s) for the monitored individual, and/or to any law enforcement communication device(s) 40, and/or to any emergency services provider communication device(s) 50, if needed or desired.

In a preferred embodiment, at any time during step 1102, the monitoring individual can utilize the user communication device 30 in order to access the central processing computer 20 in order to monitor the position or location of the personal monitoring device 10 and the monitored individual via the central processing computer 20. In a preferred embodiment, in the case of the monitored individual entering a vehicle, the monitoring individual can track and view the movement of the vehicle on a digital map which is displayed via the display device 30E of the user communication device 30. In a preferred embodiment, at any time during step 1102, the monitoring individual can also utilize the user communication device 30 to communicate with the personal monitoring device 10 and the monitored individual.

In a preferred embodiment, at step 1102, any user or operator of any law enforcement communication device(s) 40 and/or of any emergency services provider communication device(s) 50 can also utilize the same in order to monitor the position or location of the personal monitoring device 10 and the monitored individual via the central processing computer 20 and/or in order to communicate with the personal monitoring device 10 and the monitored individual and/or to communicate with any authorized user of any user communication device 30 used to monitor the monitored individual. In a preferred embodiment, in the case of the monitored individual entering a vehicle, the user or operator of the respective law enforcement communication device(s) 40 or the respective emergency services provider communication device(s) 50 can also track and view the movement of the vehicle on a digital map which is displayed via the respective display device 40E or 50E of the respective law enforcement communication device(s) 40 or the respective emergency services provider communication device(s) 50.

At step 1103, any data and/or information contained in the entry notification message and/or the entry alert message, the date and time of the generation of same, and/or any other data and/or information regarding the same, can be stored in a travel log or travel history of or for the monitored individual, which travel log or travel history can be stored in any of the databases 10H, 20H, 30H, 40H, and/or 50H, of the respective devices, computers, or communications devices described herein. Thereafter, the apparatus 100 can await the detection of the monitored individual exiting from the respective venue or the respective vehicle.

At step 1104, when the monitored individual exits from the respective venue or from the respective vehicle, the RFID tag 70, of or associated with the monitored individual's personal monitoring device 10, can be detected and/or read by the respective RFID reader 80L or RFID reader 90L which is positioned at the respective door, doorway, gate, or gateway, of the respective venue or the respective vehicle through which the monitored individual exits the same. At step 1105, the detection of the RFID tag 70 can be reported, by and/or from the RFID reader system 80 or the venue/vehicle computer 90, associated with the respective RFID reader 80L or RFID reader 90L, to the central processing computer 20, to the user communication device 30, and/or to the personal monitoring device 10, via a transmission of an appropriate signal from the respective RFID reader system 80 or the respective venue/vehicle computer 90 to the central processing computer 20, to the user communication device 30, and/or to the personal monitoring device 10.

At step 1105, the respective reader system 80 or the respective venue/vehicle computer 90, and/or the central processing computer 20, can generate an exit notification message and/or an exit alert message which can contain and/or can include information identifying the monitoring individual, information regarding the date and time when the monitoring individual exited from the respective venue or exited from the respective vehicle, and/or information identifying the respective venue or the respective vehicle. In another preferred embodiment, the personal monitoring device 10 can also generate the herein-described exit notification message and/or exit alert message.

In a preferred embodiment, in the case of the monitored individual exiting from a venue, the exit notification message and/or exit alert message can contain and/or can include information regarding the address of the venue and a contact individual and contact telephone number for the venue. In a preferred embodiment, in the case of the monitored individual exiting from a vehicle, the exit notification message and/or exit alert message can contain and/or can include information for identifying the vehicle, identifying the type of vehicle (such as, for example, a private car or vehicle, a car service vehicle, a ride-sharing vehicle (such as an Uber vehicle or a LYFT vehicle), a mass transportation vehicle, a bus, a train, a subway train, a boat of any type, kind or size, or an aircraft or helicopter of any type, kind, or size), and/or make and model information and/or vehicle identification information for the vehicle, information regarding the vehicle operator, and/or contact information for the vehicle and/or the vehicle operator and/or a telephone number for the vehicle owner or the vehicle operator. In a preferred embodiment, in the case of the monitored individual exiting from a vehicle, the exit notification message and/or exit alert message can also contain and/or can include information regarding the position or location of the vehicle at the time the monitored individual exited from the vehicle. In a preferred embodiment, the position or location of the vehicle can be determined and/or ascertained by the global positioning device 90K of the venue/vehicle computer 90 associated with the respective venue or the respective vehicle.

At step 1105, the respective reader system 80 or the respective venue/vehicle computer 90, and/or the central processing computer 20, can transmit the exit notification message and/or the exit alert message to the user communication device 30 which is used by, associated with, or assigned to, the monitoring individual for the monitored individual. In a situation where the monitored individual may be monitored by more than one monitoring individual, then the respective reader system 80 or the respective venue/vehicle computer 90, and/or the central processing computer 20 can, at step 1105, transmit the exit notification message and/or the exit alert message to the user communication device 30 which is used by, associated with, or assigned to, each such monitoring individual. At step 1105, the respective reader system 80 or the respective venue/vehicle computer 90, and/or the central processing computer 20, can also transmit the exit notification message and/or the exit alert message to any law enforcement communication device(s) 40 and/or to any emergency services provider communication device(s) 50, if needed or desired. In another preferred embodiment, the personal monitoring device 10, at step 1105, can also transmit the exit notification message and/or the exit alert message to the user communication device(s) 30 which is used by, associated with, or assigned to, the monitoring individual(s) for the monitored individual, and/or to any law enforcement communication device(s) 40, and/or to any emergency services provider communication device(s) 50, if needed or desired.

In a preferred embodiment, at any time during 1105, the monitoring individual can utilize the user communication device 30 in order to access the central processing computer 20 in order to monitor the position or location of the personal monitoring device 10 and the monitored individual via the central processing computer 20. In a preferred embodiment, at any time during 1105, the monitoring individual can also utilize the user communication device 30 to communicate with the personal monitoring device 10 and the monitored individual. In a preferred embodiment, at step 1105, any user or operator of any law enforcement communication device(s) 40 and/or of any emergency services provider communication device(s) 50 can also utilize the same in order to monitor the position or location of the personal monitoring device 10 and the monitored individual via the central processing computer 20 and/or in order to communicate with the personal monitoring device 10 and the monitored individual and/or to communicate with any authorized user of any user communication device 30 used to monitor the monitored individual.

At step 1106, any data and/or information contained in the exit notification message and/or the exit alert message can be stored in a travel log or travel history of or for the monitored individual, which travel log or travel history can be stored in any of the databases 10H, 20H, 30H, 40H, and/or 50H, of the respective devices, computers, or communications devices described herein. Thereafter, the operation of the apparatus 100 will cease at step 1107.

In a preferred embodiment, the travel log or travel history of or for the monitored individual can be accessed at any time by any respective user of a personal monitoring device 10, the central processing computer 20, a user communication device 30, a law enforcement communication device 40, or an emergency services provider communication device 50. Further, any authorized user of any personal monitoring device 10, user communication device 30, law enforcement communication device 40, or emergency services provider communication device 50, can also access the central processing computer 20 in order to request and receive any travel log or travel history of or for the monitored individual as needed.

In a preferred embodiment, the apparatus 100 of FIG. 11, can be used to monitor the travels and whereabouts of individuals of all ages. The apparatus of FIG. 11 can be used to monitor the travels and/or whereabouts of children and/or individuals of any and/or all ages and/or individuals which have any and/or all types of kinds of physical, mental, or emotional, states or conditions. In a preferred embodiment, for example, the apparatus 100 of FIG. 11 can be used to notify a parent or guardian when a child arrives at and/or has entered his or school or other venue and/or when the child leaves or exits from the school or other venue. In another preferred embodiment, the apparatus 100 of FIG. 11 can be used to notify an individual when a spouse or relative arrives at and/or has entered his or place of work, or any other venue or destination, and/or when the respective spouse or relative leaves or exits from the same. In another preferred embodiment, the apparatus 100 of FIG. 11 can be used to notify a spouse, relative, or friend, or any other person, when an individual enters into a vehicle, such as car service vehicle, a ride sharing vehicle, a mass transportation vehicle, or any other vehicle described herein, and/or when the individual exits from the respective vehicle. In this regard, the apparatus of FIG. 11 can provide notification regarding the location and/or whereabouts of any individual whether the individual enters into a venue or a vehicle and/or exits from a venue or a vehicle.

In another preferred embodiment, the apparatus 100 of the present invention can utilize the RFID tags 70, the RFID reader systems 80, the RFID readers 80L, the venue/vehicle computers 90, or RFID readers 90L, and the global positioning device 10K of the personal monitoring device 10, along with an individual's itinerary or schedule information, in order to monitor the location, movements, and/or whereabouts, of the individual. In a preferred embodiment, the apparatus 100 of the present invention can also utilize the RFID tags 70, the RFID reader systems 80, the RFID readers 80L, the venue/vehicle computers 90, or RFID readers 90L and the global positioning device 10K of the personal monitoring device 10, along with the itinerary or schedule information of or for individuals, in order to monitor the location, movements, and/or whereabouts, of the individuals of any and/or all ages.

Figure 12A:
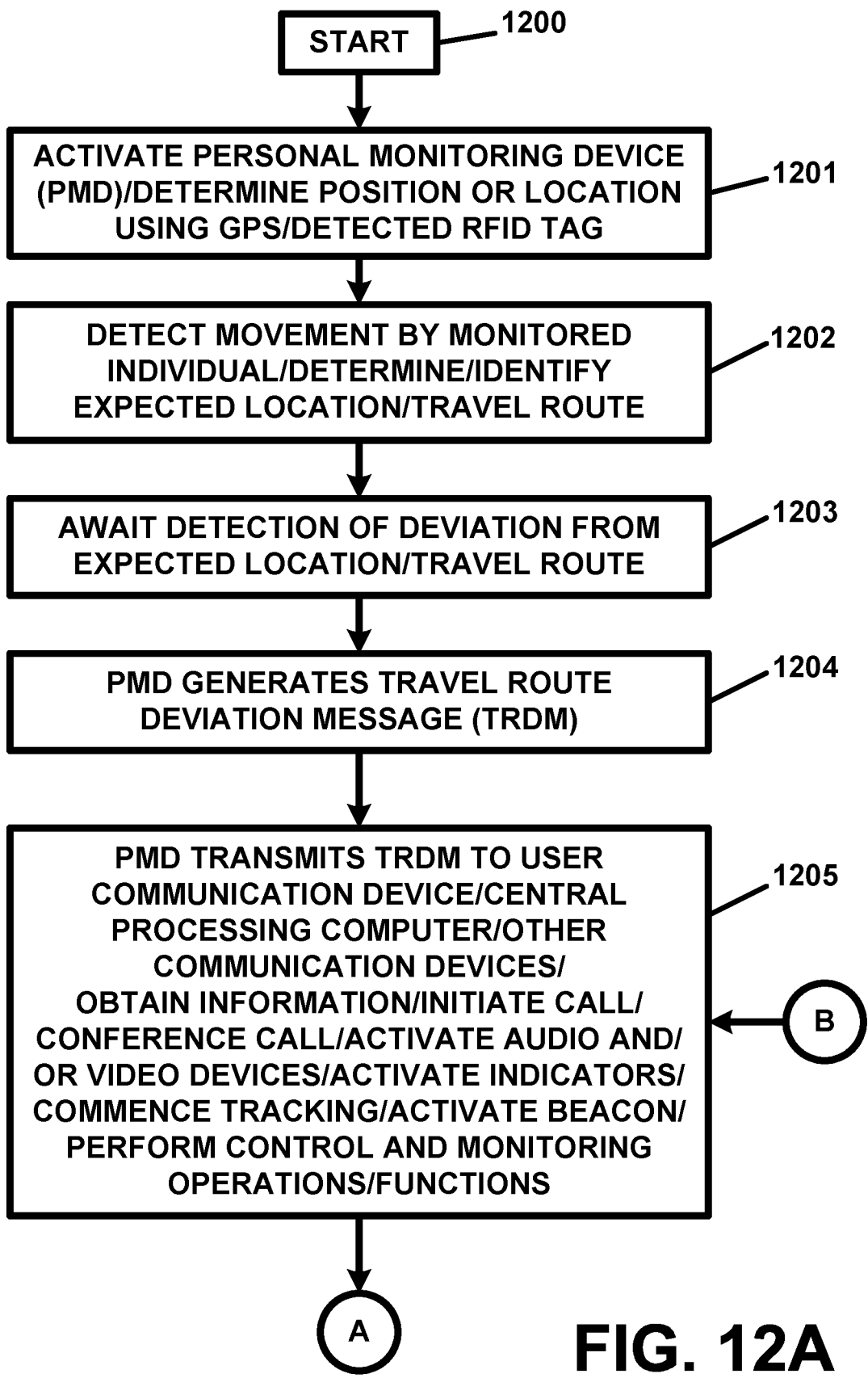
FIGS. 12A and 12B illustrate another preferred embodiment method for utilizing the apparatus of the present invention, in flow diagram form.
Figure 12B:
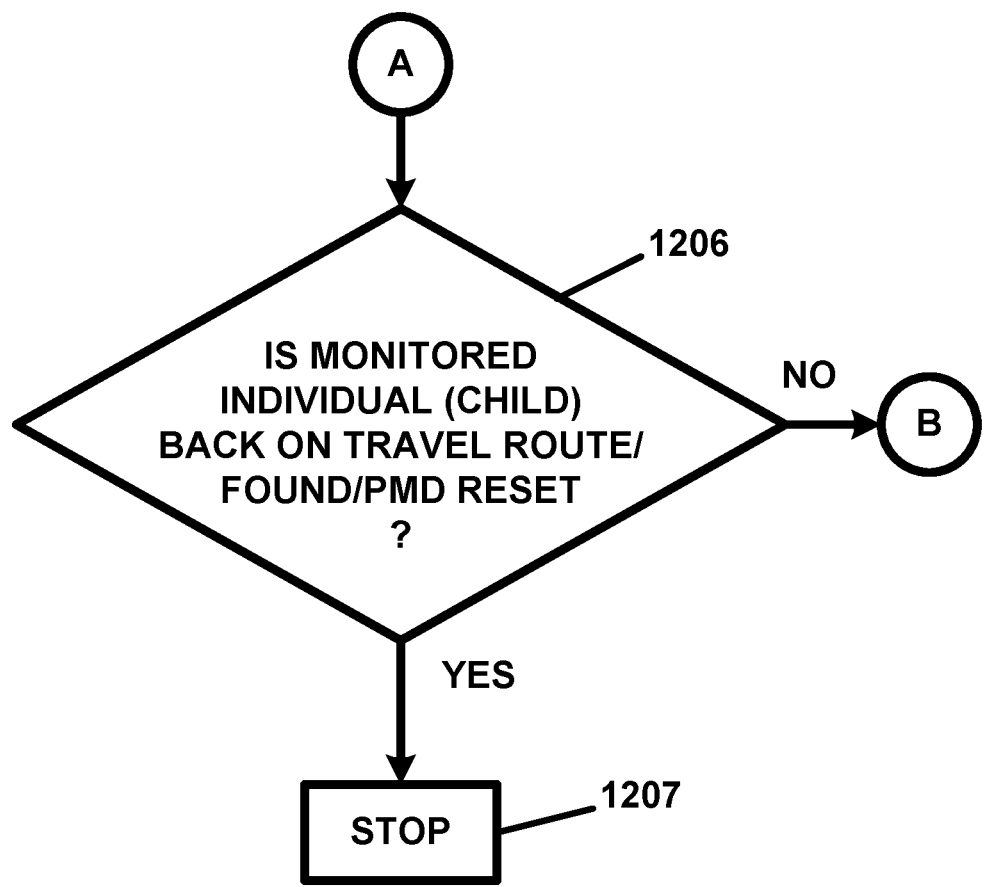

FIGS. 12A and 12B illustrate another preferred embodiment method for utilizing the apparatus 100 and method of the present invention to monitor a monitored individual, in flow diagram form. While the preferred embodiment of FIGS. 12A and 12B is described and illustrated as being used to monitor a child, it is important to note that the preferred embodiment of FIGS. 12A and 12B can be utilized in a same, a similar, and/or an analogous, manner in order to monitor any person or individual of any age and/or any person and/or individual in any type or kind of physical, mental, or emotional, state or condition. While the preferred embodiment of FIGS. 12A and 12B is described and illustrated as being used to monitor a child in or during his or her whereabouts and/or travels one place to another, it is also important to note that the present invention can also be utilized in a same, a similar, and/or an analogous, manner in order to monitor the child in or during his or her whereabouts and/or travels from one place to another, during any given period of time and/or during the course of a day, and/or to monitor any person or individual, of any age, in or during his or her whereabouts and/or travels from one place to another, during any given period of time and/or during the course of a day.

With reference to FIGS. 12A and 12B, the operation of the apparatus 100 commences at step 1200. At step 1201, the personal monitoring device 10 can be activated to operate so as to determine, ascertain, and/or monitor, the child's location or whereabouts. Depending upon the time of the particular day and the schedule of the child, the personal monitoring device 10 can determine the child's position or location and can determine such to be at an address, place, or location, where the child should be at that particular time. For example, at 9:30 AM on a Monday morning during a school year, it is expected that the child can be at his or her school. In a preferred embodiment, the child's travel itinerary or information regarding the same can be stored in the database 10H of the personal monitoring device 10, and/or in the database 20H of the central processing computer 20, and can include information indicating that the child should leave school at approximately 3:00 PM and travel back to his or her home, either by being driven in a vehicle or a school bus equipped with a respective RFID reader 80L or RFID reader 90L, or by riding a bicycle, or by walking, or by travel by any other mode of travel.

In a preferred embodiment, the personal monitoring device 10 can utilize its global positioning device 10K in order to automatically and/or to constantly ascertain and/or monitor its position or location, and/or the personal monitoring device 10 can ascertain or monitor its position or location at, in, or on, a respective venue or at, in, or on, a respective vehicle when the RFID tag 70 of the personal monitoring device 10 is detected and/or read by a respective RFID reader system 80, an RFID reader 80L, a venue/vehicle computers 90, or a RFID reader 90L, stationed at or located at the respective venue or the respective vehicle. In a preferred embodiment, the respective RFID reader 80 or the respective venue/vehicle computer 90, upon detecting and reading the RFID tag 70, on or associated with the personal monitoring device 10, can generate and transmit a tag read signal to the personal monitoring device 10. In a preferred embodiment, the tag read signal can contain, among any other desired information, information regarding the respective address or position or location information of the respective venue or the respective vehicle and the date and time when the RFID tag 70 was detected and/or read.

As noted herein, in a preferred embodiment, an RFID reader 80L or an RFID reader 90L can be positioned at, or can be stationed at, a respective door, doorway, gate, or gateway, for each door, doorway, gate, or gateway, which serves as an entry point into, or exit point from, the respective venue or the respective vehicle. In a preferred embodiment, each respective RFID reader system 80, RFID readers 80L, venue/vehicle computers 90, or RFID reader 90L, can be utilized in a same, a similar, and/or an analogous, manner, as described in the preferred embodiment of FIG. 11 in order to detect and/or read the RFID tag 70 of or associated with the personal monitoring device 10 as the personal monitoring device 10 and the child enters into or on, and/or exits from, a respective venue or a respective vehicle.

In a preferred embodiment, at step 1201, the personal monitoring device 10 can automatically, constantly, and/or continuously, monitor its position or location and/or any updates to its position or location, by using any position or location information obtained by or from its global positioning device 10K, and/or by using stored address information for or regarding any venue in or at which the personal monitoring device 10 has been determined to be located, as the result of the RFID tag 70 of or associated with the personal monitoring device 10 having been detected or read by an RFID reader 80L or 90L which is located at that venue, and/or by using any global positioning information, as determined by the global positioning system device 10K of the personal monitoring device 10, for or regarding any vehicle in or at which the personal monitoring device 10 has been determined to be located, as the result of the RFID tag 70 of or associated with the personal monitoring device 10 having been detected or read by an RFID reader 80L or 90L which is located at that vehicle.

At step 1202, the personal monitoring device 10, and/or the CPU 10A of the same, can detect a movement of the personal monitoring device 10, and can detect the child's location, and/or movement from his or her school, or expected location at that given time, such as by monitoring and/or by comparing a change in the child's position or location, as determined by utilizing the global positioning system (GPS) device 10K of the personal monitoring device 10, and/or by using any information regarding any stored address information for or regarding any venue in or at which the personal monitoring device 10 has been determined to be located or by using any global positioning information, as determined by the global positioning system device 10K of the personal monitoring device 10, for or regarding any vehicle in or at which the personal monitoring device 10 has been determined to be located.

At step 1202, upon detecting the child's movement and the time of the same, and current position or location, the personal monitoring device 10, if determining the time to be approximately 3:00 PM, can identify the child's expected location and/or a preferred travel route back home. In a preferred embodiment, the child's preferred travel route from his or her school back to his or her home can be pre-selected and can be pre-programmed by his or her parent, or guardian, or any other caregiver, or other authorized person (a herein-defined "monitoring individual") and can be stored in the personal monitoring device 10 and/or in the database 20H of the central processing computer 20.

At step 1202, the personal monitoring device 10 will determine or ascertain the expected location and/or the preferred travel route the child should respectively be located at or be taking back home and, if a travel route is concerned, will monitor the child's location or travel along that preferred travel route. From this point on, the preferred travel route of the child can simply be referred to as the "travel route".

At step 1203, the personal monitoring device 10 can await a detection that the child is not located at the expected location for that time, or has deviated from the travel route, or has gone off course from the travel route. Upon detecting that the child is not at the expected location, or has deviated from the travel route, or has gone off course from the travel route, the operation of the personal monitoring device 10 will proceed to step 1204. At step 1204, the personal monitoring device 10, in a preferred embodiment, can perform any one or more of a number of functions or operations in response to the detection of the child not being at the expected location, or has deviated from the travel route, or has gone off course from the travel route.

In a preferred embodiment, at step 1204, the personal monitoring device 10, and in particular, the CPU 10A, and/or the central processing computer 20, can generate an itinerary deviation message, in the case in which the child is not at the expected location, or a travel route deviation message, in the case in which the child has deviated from the travel route or has gone off course from the travel route. In the preferred embodiment, the itinerary deviation message can contain and/or include information regarding the current location of the child and/or the time in which the child arrived there, if known. For example, as an example of the child not being at an expected location, the child could be detected as being at the school at 3:30 when the child should otherwise be on a school bus (a vehicle equipped with an RFID reader 80L or 90L) and on a trip back to his or her house. In the preferred embodiment, the travel route deviation message can contain and/or include the current position or location of the child, as determined by the position or location of the personal monitoring device 10, and/or the time and/or place, position, or location, when and/or where the child deviated from or left the travel route. The travel route deviation message can also include information regarding the portion of the child's itinerary associated with the travel route from which the child has deviated. For example, as in the example of the preferred embodiment when the child has deviated from his or her travel back home from school, the travel route deviation message can also contain information indicating that the child has deviated from the travel route he or she was taking to go home from school.

At step 1205, the personal monitoring device 10 can automatically transmit the respective itinerary deviation message or the respective travel route deviation message to the user communication device 30 which is used by, associated with, or assigned to, the monitoring individual for the child. In a preferred embodiment, for example, the monitoring individual can be a parent, a grandparent, a sibling, a relative, a friend, a guardian, or any other authorized person. In a situation where the child may be monitored by more than one monitoring individual, then the personal monitoring device 10, at step 1205, can transmit the respective itinerary deviation message or the respective travel route deviation message to the user communication device 30 which is used by, associated with, or assigned to, each and every monitoring individual for the child. In a preferred embodiment, the personal monitoring device 10 can generate and transmit updated itinerary deviation messages or the travel route deviation messages at any pre-determined or pre-selected time intervals.

At step 1205, the personal monitoring device 10 can also automatically transmit the respective itinerary deviation message or the respective travel route deviation message to the central processing computer 20 so as to report the child's itinerary deviation or travel route deviation to the central processing computer 20 and/or to any company or entity which operates same. At step 1205, the personal monitoring device 10 can also automatically transmit the respective itinerary deviation message or the respective travel route deviation message to the law enforcement communication devices 40 of or associated with each law enforcement agency or department associated with the city, town, municipality, or political subdivision, in which the child was detected as having deviated from the itinerary or from the travel route, as well as to each law enforcement communication device(s) 40 of or associated with any neighboring cities, towns, municipalities, or political subdivisions. At step 1205, the personal monitoring device 10 can also automatically transmit the respective itinerary deviation message or the respective travel route deviation message to the emergency services provider communication device 50 of or associated with the emergency services provider agency or department of or for the city, town, municipality, or political subdivision, in which the child was detected as having deviated from the itinerary or from the travel route, as well as to each emergency services provider communication device 50 of or associated with any neighboring cities, towns, municipalities, or political subdivisions. At step 1205, the respective itinerary deviation message or the respective travel route deviation message can be received by the user communication device 30, and by each central processing computer 20 and/or law enforcement communication device 40 and/or emergency services provider communication device 50 to which it was sent.

At step 1205, the personal monitoring device 10 can also obtain, determine, read, or record, any physiological or healthcare information regarding the child such as, for example, but not limited to, the child's heart rate, pulse rate, blood pressure, body temperature, blood sugar level, or any other healthcare information or healthcare-related data and/or information, or any other physical condition, physiological condition, or healthcare condition, which can be measured or measurable by any wearable device or by any implanted device or implantable device which can be obtained by or using any of the respective and herein-described devices, equipment, monitors, or measurement devices, which can be wearable or non-wearable and/or which can be connected to or with, or wirelessly linked to or with the personal monitoring device 10 and/or the CPU 10A of same. Any data and/or information obtained regarding any of the herein-described data and/or information can also be included in the respective itinerary deviation message of the respective travel route deviation message and/or in any subsequently generated and transmitted itinerary deviation messages of travel route deviation messages or any updated itinerary deviation messages or any updated travel route deviation messages. For example, in addition to the child's current position or location, information regarding the child's heart rate, body temperature, or any other healthcare information can be provided in the respective itinerary deviation message(s) of travel route deviation message(s).

In another preferred embodiment, the respective itinerary deviation message or travel route deviation message can also contain and/or include the temperature of the environment in which the child is located, which can be exterior temperature if the child and the personal monitoring device 10 is located outdoors, or an interior temperature if the child and the personal monitoring device 10 are located indoors.

In a preferred embodiment, the personal monitoring device 10, at step 1205, can also initiate a cellular or wireless telephone call to the user communication 30 of the monitoring individual. In another preferred embodiment, if more than one monitoring individuals are associated with the child, then the personal monitoring device 10 can initiate a cellular or wireless telephone call, and/or a telephone conference call, to and/or so as to include the child and all monitoring individuals for the child. In another preferred embodiment, the personal monitoring device 10 can initiate a cellular or wireless telephone call, and/or a telephone conference call, to and/or so as to include at least one monitoring individual and a law enforcement officer or individual, via and/or by including a respective law enforcement communication device 40, and/or an emergency services provider individual or person via and/or by including an emergency services provider communication device 50.

In a preferred embodiment, the cellular or wireless telephone call can be made so as to put the child into live contact with, and/or into live communication with, the monitoring individual or monitoring individuals, and/or so as to put the child and the monitoring individual or monitoring individuals into live contact with, and/or into live communication with, law enforcement personnel and/or emergency services personnel.

In a preferred embodiment, at step 1205, once the cellular or wireless telephone call and/or any conference line involving the monitoring individual or monitoring individuals, and/or any law enforcement law enforcement personnel and/or emergency services personnel, has been made and, with the call line and/or conference line being live and/or on-going, the personal monitoring device 10 can de-activate the personal monitoring device's 10 telephone call on/off switch, or on/off switch functionality, on or in the personal monitoring device 10 so that the personal monitoring device 10 cannot be disconnected from the telephone call and/or the conference line. In a preferred embodiment, the herein-described de-activation of the telephone call on/off switch, or on/off switch functionality, of the personal monitoring device 10 can be effectuated by using, and/or by programming the personal monitoring device 10, with or using any appropriate and/or suitable software program, algorithm, or software application. In a preferred embodiment, the personal monitoring device 10 can also be programmed and/or equipped so as to detect being disconnected from, or dropped from, the telephone call and/or conference call, and can automatically re-connect to the telephone call and/or to the conference call. It is to be understood, that any of the herein-described personal monitoring device(s) 10, user communication device(s) 30, law enforcement communication device(s) 40, and/or an emergency services provider communication device(s) 50, can be equipped with long lasting batteries or power sources, external batteries or power sources, and/or any other supplemental batteries or power sources so as to ensure that sufficient electrical power is available and can be supplied to any of the herein-described personal monitoring device(s) 10, user communication device(s) 30, law enforcement communication device(s) 40, and/or an emergency services provider communication device(s) 50.

In a preferred embodiment, the herein-described functionality of establishing a cellular or wireless telephone call, and/or conference call, can allow the child to be brought into, and to be maintained in, live contact with and/or live communication with, his or her monitoring individual or one or more monitoring individuals, and/or with any number of law enforcement personal and/or emergency services personnel. In this manner, the monitoring individual or monitoring individuals, and/or any law enforcement personnel and/or emergency services personnel, can speak with the child, can comfort or reassure the child that all will be okay, and/or can ascertain the child's whereabouts, while the child my be lost or off track. In a preferred embodiment, the personal monitoring device 10 can activate the speakerphone, and/or any speakers and/or microphone, of same for and/or during the cellular or wireless telephone call and/or conference call.

In a preferred embodiment, any activation or use of a speakerphone functionality of the personal monitoring device 10 can also be utilized in order to establish or facilitate an intercom, or an intercommunication or intercom-like, communication platform or system which can provide for open communication involving or between the child, any individual or person coming into contact with the child, and the monitoring individual, and/or any law enforcement personnel, emergency services personnel, or any operator of the central processing computer 20.

In a preferred embodiment, the personal monitoring device 10 can also, at step 1205, activate any camera, any video recording device or equipment, any microphone, or any audio recording device, of same, and/or any device or equipment of the video and/or audio recording device(s) 10J of same, for and/or during the cellular or wireless telephone call and/or conference call.

In another preferred embodiment, the personal monitoring device 10 can, at step 1205, activate one or more indicator lights 18 or 19 on the personal monitoring device 10 which can be used to indicate that the child is currently outside of his or her "safe" zone of travel. As noted herein, the personal monitoring device 10 can be provided with one or more indicator lights 18 or 19 which can be used to indicate when the child is inside or within his or her "safe" zone of travel and one or more indicator lights 18 or 19 which can be used to indicate when the child is not in, or outside, of his or her "safe" zone of travel. In a preferred embodiment, when the child is inside or within his or her "safe" zone of travel, one or more of these indicator lights 18 or 19 can be lit or illuminated with a green light. In a preferred embodiment, when the child is outside of his or her "safe" zone of travel, one or more of these indicator lights 18 or 19 can be lit or illuminated with a red light. In a preferred embodiment, the personal monitoring device 10 and/or the CPU 10A can, at step 1205, activate or cause one or more of the indicator lights 18 or 19 to be lit or illuminated in red. In this regard, any individual or person who may see, or come into contact with the child can be notified, by seeing the red lights on the personal monitoring device 10, that the child may be lost or otherwise in need of assistance. In a preferred embodiment, any indicator lights can also be provided via the display screen or in or via a portion or section of the display screen.

In a preferred embodiment, the personal monitoring device 10 can also, at step 1205, activate any camera, any video recording device or equipment, any microphone, or any audio recording device, of same, and/or any device or equipment of the video and/or audio recording device(s) 10J of same, for obtaining pictures, video information, video clips, audio information, or audio clips, of the child, or any individual's or person who or may come into contact with the child, and/or of any of the child's surroundings, environment, or location. In a preferred embodiment, any pictures, video information, video clips, audio information, or audio clips, recorded by and at the personal monitoring device 10 can be transmitted to, and stored by or in, each of the user communication device 30 of the monitoring individual, each user communication device 30 of each monitoring individual, the central processing computer 20, or any law enforcement communication device(s) 40, and/or an emergency services provider communication device(s) 50. In this regard, any audio or video which can be used to ascertain the child's location or which can be used to ascertain any individuals or persons with the child or who the child may have come into contact with, can be recorded by the personal monitoring device 10 and can be transmitted to, and/or viewed and/or listened to, and/or stored, via or at each of the user communication device 30 of the monitoring individual, each user communication device 30 of each monitoring individual, the central processing computer 20, or any law enforcement communication device(s) 40, and/or an emergency services provider communication device(s) 50.

In another preferred embodiment, the personal monitoring device 10 can also, at step 1205, begin to, or can continue to, record instances when the child enters into or on a venue or into or on a vehicle, by detecting instances when the RFID tag 70, which is associated with the personal monitoring device 10 is detected or read by any RFID reader 9-L or RFID reader 90L, and/or can track the child's movements and can generate respective location update messages or respective tracking update messages at any pre-selected time interval(s), containing information regarding the child's location(s), movement(s), and speed of travel or movement. In a preferred embodiment, the personal monitoring device 10, as well as the central processing computer(s) 20, the user communication(s) 30, the law enforcement communication device(s) 40, and/or the emergency services provider communication device(s) 50, can be equipped with software to calculate or otherwise determine the child's speed of movement. In this manner, depending on the speed of movement of the child, it can also be determined if the child is traveling in or on a vehicle or is traveling on foot. In a preferred embodiment, the respective location update messages or the respective tracking update messages can be automatically transmitted, at periodic time intervals, from the personal monitoring device 10 to the user communication(s) 30 of the monitoring individual(s), and/or, or as well as, to the central processing computer(s) 20, any other user communication(s) 30, the law enforcement communication device(s) 40, and/or the emergency services provider communication device(s) 50.

In a preferred embodiment, information regarding the child's location or movement can be also displayed and/or tracked on or via a digital or satellite map which can be displayed on the display device 30E of the respective user communication(s) 30, or can be displayed on the respective display device(s) of the central processing computer(s) 20, the law enforcement communication device(s) 40, and/or the emergency services provider communication device(s) 50. In a preferred embodiment, the information regarding the child's location or movement can also be displayed and/or tracked on or via a digital or satellite map which can be displayed on the display screen 12 of the personal monitoring device 10.

In a preferred embodiment, the personal monitoring device 10 can also, at step 1205, activate a homing beacon or beacon of the personal monitoring device 10. In a preferred embodiment, the homing beacon or beacon of the personal monitoring device 10 can transmit or provide a signal, a distress signal, or any other indication, which can be utilized in connection with a corresponding receiver, which can be provided in or with each of the user communication device(s) 30, the central processing computer(s) 20, the law enforcement communication device(s) 40, and/or the emergency services provider communication device(s) 50, and which can allow for any user or operator of such device(s) or computers 30, 20, 40, and/or 50, to track and/or to "home" in on or locate the child. In a preferred embodiment, the equipment and technology which can be used to implement the beacon or homing beacon and any associated receivers can be the same as, similar to, or analogous to, the technology which was used in vehicle tracking devices such as Lo-Jack® systems and/or any other vehicle recovery systems or any other suitable vehicle tracking and locating systems which are known by those skilled in the art of vehicle recovery systems. Any of the herein-described users or operators of any of the herein-described device(s) or computers 30, 20, 40, and/or 50, can thereafter use his/her/its respective device or computer 30, 20, 40, and/or 50, in order to "home" in on the signals transmitted from or emitted from the beacon or homing beacon.

In a preferred embodiment, at step 1205, the personal monitoring device 10 can also play any pre-recorded messages or video clips or audio clips, which messages, video clips, or audio clips, to the child via the display screen 12 and speakers 16. In a preferred embodiment, the pre-recorded messages or video clips or audio clips can be pre-recorded by the monitoring individual or by any number of monitoring individuals, and can be stored in the personal monitoring device 10. The pre-recorded messages or video clips or audio clips can be used in order to comfort the child or calm the child down, if needed, by providing him or her with the voice and/or image of the monitoring individual or monitoring individuals. The pre-recorded messages or video clips or audio clips can also contain or include contact information for the child or his or her monitoring individual, name and address of the child, contact telephone numbers, contact e-mail addresses, contact text message, MMS message, or SMS message, numbers, IP addresses, ad/or any other information, and/or can contain any instructions and/or information needed for caring for the child, including any medications or drugs which the child requires and/or any other healthcare needs or any special needs of the child. In this regard, the pre-recorded messages or video clips or audio clips can also contain or include any information which any individual or person may need or find helpful in assisting the child until the child is found or recovered.

In a preferred embodiment, the personal monitoring device 10 can also, at step 1205, provide information, and/or a link to information, regarding or contained in the healthcare records of the child. In a preferred embodiment, any information contained in the child's healthcare records can be stored in the personal monitoring device 10. In another preferred embodiment, a link or a hyperlink to the child's healthcare records can be provided via the personal monitoring device 10 so as to allow any individual or person to gain access to the child's healthcare records, which healthcare records can be stored in or at the central processing computer 20, the user communication device 30 of a monitoring individual, or the healthcare records computer 60. In a preferred embodiment, the personal monitoring device 10 can provide information, and/or a link to information, regarding any healthcare needs of the child or any special needs of the child.

In a preferred embodiment, the personal monitoring device 10 can also, at step 1205, provide information regarding any instructions or directions for guiding the child back onto his or her travel route. In another preferred embodiment, the personal monitoring device 10 can, at step 1205, activate or turn on a flashlight or a flashlight functionality, and/or a strobe light or a strobe light functionality.

In a preferred embodiment, at any time during step 1205 and/or at any other time, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, the user communication device 30 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In a preferred embodiment, the user communication device 30 can also, at step 1205 and/or at any other time, transmit the control signal over any appropriate communication network(s) to the personal monitoring device 10. In another preferred embodiment, the user communication device 30 can transmit the control signal over the appropriate communication network(s) to the personal monitoring device 10 via the central processing computer 20.

In another preferred embodiment, the central processing computer 20, at step 1205 and/or at any other time, can also generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, the user communication device 30 and/or the central processing computer 20 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In another preferred embodiment, any authorized law enforcement communication device 40 and/or any authorized emergency services provider communication device 50, at step 1205 and/or at any other time, can also generate and/or can transmit a control signal to the personal monitoring device 10 in order to enable, disable, activate, de-activate, control an operation of, or monitor an operation of, the personal monitoring device 10 and/or any component, system, device, or equipment, of same. In this regard, any authorized law enforcement communication device 40 and/or any authorized emergency services provider communication device 50 can generate and/or can transmit a control signal to the personal monitoring device 10 in order to enable, disable, activate, de-activate, control an operation of, or monitor an operation of, the personal monitoring device 10 and/or any component, system, device, or equipment, of same, including, but not limited to, the CPU 10A, the input device(s) 10D, the display device(s) 10E, the transmitter(s) 10F, the receiver(s) 10G, the output device(s) 10I, the video and/or audio recording device(s) 10J, the GPS device 10K, any of the device functional systems 10L, the display screen 12, the display section 13, the keyboard section 14, the microphone(s) 15, the speaker(s) 16, the camera(s) 17, or the indicator light(s) 18 or 19.

In a preferred embodiment, the law enforcement communication device 40 and/or the emergency services provider communication device 50 can also, at step 1205, and/or at any other time, transmit the control signal over any appropriate communication network(s) to the personal monitoring device 10. In another preferred embodiment, the law enforcement communication device 40 and/or the emergency services provider communication device 50 can transmit the control signal over the appropriate communication network(s) to the personal monitoring device via the central processing computer 20.

In a preferred embodiment, at step 1205, the personal monitoring device 10 and/or the CPU 10A can continue determining and tracking the child's position or location and/or movement by using the global positioning system device 10K. In a preferred embodiment, the personal monitoring device 10 and/or the CPU 10A, at any pre-defined or pre-selected time interval, which in a preferred embodiment can be one (1) minute or any other suitable time interval, and while any and/or all functionality described herein as being performed at step 1205, can determine if the child made it back onto his or her travel route and/or can determine if the child has been found. In this regard, the operation of the personal monitoring device 10 can proceed to step 1206 and the personal monitoring device 10 and/or the CPU 10A can determine if the child is back on his or her travel route or can determine if the child has been found and that an instruction to reset the personal monitoring device 10 has been received by the personal monitoring device 10 or has been input into the personal monitoring device 10.

If, at step 1206, it is determined that the child is back on his or her travel route, or that the child has been found, or that an instruction to reset the personal monitoring device 10 has been received by the personal monitoring device 10 or has been input into the personal monitoring device 10, then the operation of the apparatus 100 will cease at step 1207. Thereafter, the personal monitoring device 10 can be reset for future use. If at step 1206, it is determined that the child has still not made it back to his or her travel route, or that the child has still not been found, or that no instruction to reset the personal monitoring device 10 has been received by the personal monitoring device 10 or has been input into the personal monitoring device 10, then the operation of the apparatus 100 will return to, or continue on as described during, step 1205 as described herein. The apparatus 100 will thereafter continue to function and/or operate at steps 1205 and 1206 until it is determined by the personal monitoring device 10 and/or the CPU 10A that the child is found to be back on his or her travel route, or the child has been found, or until an instruction to reset the personal monitoring device 10 has been received by the personal monitoring device 10 or has been input into the personal monitoring device 10.

Although described herein as being utilized to monitor a child, it is important to note that the apparatus 100 and the personal monitoring device 10 of FIGS. 12A and 12B can be utilized in a same, a similar, and/or an analogous, manner to monitor individuals of any age, including but not limited to infants, children, adolescents, teenagers, adults of any age, elderly individuals, individuals having no healthcare issues, conditions, problems, or challenges, and/or individuals having healthcare issues, conditions, problems, or challenges. The apparatus 100 and method of the present invention as well as the apparatus of FIGS. 12A and 12B can be used to monitor children who may be afflicted with autism, or any disabilities, or who may lack communications skills, and/or who may have other conditions, as well as individuals of any age who are afflicted with Alzheimer's disease or Dementia, or any other healthcare conditions. The apparatus 100 and method of the present invention as well as the apparatus of FIGS. 12A and 12B can be used to monitor individuals of any age who may have no healthcare conditions or problems, but who might want to simply utilize the apparatus 100 and method of the present inventions for the numerous benefits it can provide.

In a preferred embodiment, any of the functions and/or functionality described herein as being performed by the personal monitoring device 10 at or during step 1205 can be pre-programmed into the personal monitoring device 10 beforehand by any authorized individual and/or by a monitoring individual. In a preferred embodiment, any of the functions and/or functionality described herein as being performed by the personal monitoring device 10 at or during step 1205 can be changed or can be re-programmed at any time. In another preferred embodiment, any functions and/or functionality described herein as being performed by the personal monitoring device 10 at or during step 1205 can also be enabled, disabled, activated, deactivated, or controlled, or monitored, by or via the user communication device 30, the central processing computer 20, the law enforcement communication device 40, or the emergency services provider communication device 50.

In a preferred embodiment, as well as in any and/or all of the embodiments described herein, a personal monitoring account can be created or established for any monitored individual with whom the apparatus 100 and method of the present invention can be utilized. In this regard, a personal monitoring account can be established for a monitored individual and can be registered with the central processing computer 20, and/or with any law enforcement departments and/or agencies and/or with an emergency services providers departments and/or agencies so that the central processing computer 20 and the respective law enforcement communication devices 40 and/or emergency services providers communication devices 50 can have records and/or information for or regarding any monitored individuals and the respective individual(s) who is/are to be monitoring them (the so-call "monitoring individuals"). Any of the data and/or information described herein as being stored in any of the databases 10H, 20H, 30H, 40H, 50H, and/or 60H, of any of the herein-described personal monitoring devices 10, central processing computers 20, user communication devices 30, law enforcement communication devices 40, emergency services providers communication devices 50, and/or healthcare records computers 60, can be stored in a respective monitored individuals personal monitoring account.

In another preferred embodiment, the operation of the apparatus 100 and/or the personal monitoring device 10 can be triggered by, or can be activated by or in response to the actions of, a monitoring individual. In a preferred embodiment, a monitoring individual can utilize a software application or a software "app" in order to determine the position or location of personal monitoring device 10 and the monitored individual. The software application or software "app", in a preferred embodiment, should be capable of determining the position or location of the personal monitoring device 10 and the monitored individual at any time and/or on demand by the monitoring individual. In another preferred embodiment, the monitoring individual can also perform a "pinging" operation in order to utilize a communications services provider or any other suitably equipped entity in order to "ping" or determine the position or location of the personal monitoring device 10 and the monitored individual.

In a preferred embodiment, at any time, a monitoring individual can either utilize a software application or a software "app" on his or her user communication device 30, or can "ping" the personal monitoring device 10 of or associated by the monitored individual, in order to determine the position or location of the personal monitoring device 10 and the monitored individual and/or to determine if the monitored individual is at an expected place or location, is traveling on an appropriate travel route at that point or instant in time, or is at an unexpected or unapproved place or location, or has deviated from an appropriate travel route at that point or instant in time. If the monitored individual is determined to be at an unexpected or unapproved place or location, or has deviated from an appropriate travel route at that point or instant in time, the monitoring individual can activate the apparatus 100 and utilize same to find or locate, or otherwise provide assistance to, the monitored individual.

As described herein, any user or individual who utilizes a personal monitoring device 10, or who has a personal monitoring device 10 assigned to him or her, or who has a personal monitoring device 10 associated with him or her, can again be referred to herein, or can be defined herein as being, a "monitored individual". As also described herein, any user or individual who utilizes a user communication device 10 to monitor a monitored individual can be referred to herein, or can be defined herein as being, a "monitoring individual".

As described herein, it is envisioned that a personal monitoring device 10 can be programmed with, or have stored therein or therewith, information regarding the monitored individual's home address, residence address, school residence address or place, workplace address, or other address, place, or location, which is considered to be that monitored individual's place of safety or "home base" or "safe location". In a preferred embodiment, it is envisioned that the personal monitoring device 10 can be programmed with, or can have stored therein or therewith, information regarding any address(es), place(s), or location(s), to which the monitored individual typically travels on a daily basis. For example, the personal monitoring device 10 can be programmed with, or can have stored therein or therewith, information regarding the monitored individual's school address, place, or location, workplace address, place, or location, employment address, place, or location, activity or event address, place, or location, or any other address, place, or location, at which the monitored individual is expected to be, or to which the monitored individual is known or expected to be traveling, on a weekday basis, on a weekend daily basis, or on any daily basis.

As also described herein, the personal monitoring device 10 can also be programmed with the monitored individual's travel itineraries and/or travel schedules for traveling to and between one address, place, or location to another address, place, or location. In this regard, the personal monitoring device 10 can also be programmed with travel routes or directions for traveling to and between one address, place, or location to another address, place, or location. As also noted herein, in a preferred embodiment, the personal monitoring device 10 can also be programmed with software programs, navigation programs, or any algorithms or software applications, for identifying, determining, ascertaining, or calculating, any travel routes or directions for traveling from and between one address, place, or location, to another address, place, or location.

In any and/or all of the embodiments described herein, the personal monitoring device 10 can be utilized in connection with, or in conjunction with, the apparatus 100, the central processing computer 20, a user communication device 30 associated with, or used by, any user or individual authorized to, or assigned to, monitor the monitored individual, any law enforcement communication device 40, and/or any emergency services provider communication device 50. As also described herein, the personal monitoring device 10 can also be utilized as a stand-alone device by the monitored individual in order to allow the monitored individual to monitor his or her travels, whereabouts, or environment.

In another preferred embodiment, the apparatus 100 of the present invention can utilize the RFID tags 70, the RFID reader systems 80, the RFID readers 80L, the venue/vehicle computers 90, or the RFID readers 90L, along with an individual's itinerary or schedule information, in order to monitor the location, movements, and/or whereabouts, of the individual. and/or to determine whether or not a monitored individual is deviating from, or has deviated from, his or her travel itinerary.

Figure 13:
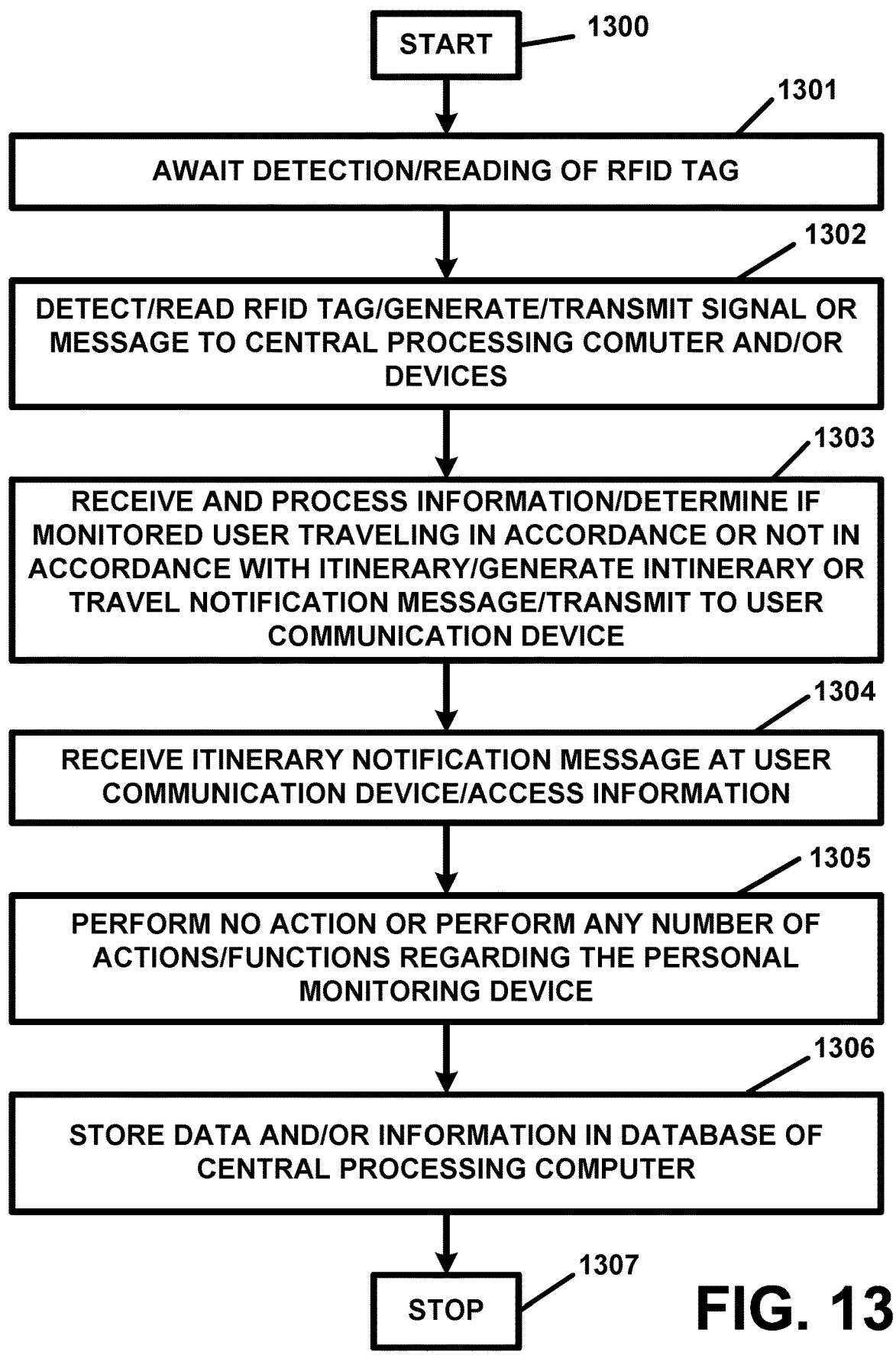
FIG. 13 illustrates a preferred embodiment method for utilizing the apparatus of the present invention, in flow diagram form.

FIG. 13 illustrates another preferred embodiment method for utilizing the apparatus 100 and method of the present invention to monitor a monitored individual, in flow diagram form. It is important to note that the preferred embodiment of FIG. 13 can be utilized in order to monitor any person or individual of any age and/or any person and/or individual in any type or kind of physical, mental, or emotional, condition. It is also important to note the present invention can be utilized in monitor a child in or during his or her whereabouts and/or travels from one place to another, during any given period of time and/or during the course of a day, and/or to monitor any person or individual, of any age, in or during his or her whereabouts and/or travels from one place to another, during any given period of time and/or during the course of a day.

In another preferred embodiment, the apparatus 100 of the present invention can utilize the RFID tags 70, the RFID reader systems 80, the RFID readers 80L, the venue/vehicle computers 90, or RFID readers 90L, along with an individual's itinerary or schedule information, in order to monitor the location, movements, and/or whereabouts, of the individual. In a preferred embodiment, the apparatus 100 of the present invention can also utilize the RFID tags 70, the RFID reader systems 80, the RFID readers 80L, the venue/vehicle computers 90, or RFID readers 90L, along with the itinerary or schedule information of or for individuals, in order to monitor the location, movements, and/or whereabouts, of the individuals of any and/or all ages.

With reference to FIG. 13, the operation of the apparatus 100 commences at step 1300. At step 1301, the apparatus 100 will await a detection and/or a reading of the RFID tag 70 on or associated with the monitored individual's personal monitoring device 10. In a preferred embodiment, the RFID tag 70 can be detected and/or read by an RFID reader 80L, which is associated with an RFID reader system 80 which services a venue or a vehicle, or the RFID tag 70 can be detected and/or read by an RFID reader 80L or by an RFID reader 90L which is associated with a venue/vehicle computer 90 which is associated with, or located at, a venue or a vehicle. As noted herein, in a preferred embodiment, the respective venue or vehicle can be equipped with an RFID reader(s) 80L of a respective RFID reader system 80, or an RFID reader(s) 90L of a respective venue/vehicle computer 90.

In a preferred embodiment, an RFID reader 80L or an RFID reader 90L can be positioned at, or can be stationed at, a respective door, doorway, gate, or gateway, for each door, doorway, gate, or gateway, which serves as an entry point into, or exit point from, the respective venue or the respective vehicle. In a preferred embodiment, the respective RFID reader 80L or the respective RFID reader 90L can detect and/or read the RFID tag 70, which is on or associated with the personal monitoring device 10 of the monitored individual, when the monitored individual enters into or onto a respective venue or into or onto a respective vehicle.

At step 1302, the RFID reader 80L or an RFID reader 90L can detect and/or read the RFID tag 70 on or associated with the monitored individual's personal monitoring device 10 when the monitored individual enters into or onto a respective venue or a respective vehicle or when the monitored user exits from the respective venue or the respective vehicle. In a preferred embodiment, the monitored individual enters or exits the respective venue or the respective vehicle via a respective door, doorway, gate, or gateway, for each door, doorway, gate, or gateway, which serves as an entry point into, or exit point from, the respective venue or the respective vehicle. As noted above, the respective RFID reader 80L or an RFID reader 90L is or can be located at, positioned at, or stationed at, a respective door, doorway, gate, or gateway, of the respective venue or the respective vehicle.

At step 1302, the detection of the RFID tag 70 can be reported by and/or from the RFID reader system 80 or the venue/vehicle computer 90 associated with the respective RFID reader 80L or the respective RFID reader 90L, to the central processing computer 20, to the user communication device 30, and/or to the personal monitoring device 10, via a transmission of a signal or message, which signal or message is generated by, and transmitted from, the respective RFID reader system 80 or the respective venue/vehicle computer 90 at step 1302. At step 1302, the signal or message is transmitted from the respective RFID reader system 80 or the respective venue/vehicle computer 90 to the central processing computer 20, to the user communication device 30, and/or to the personal monitoring device 10. In a preferred embodiment, the signal or message can contain information identifying the respective venue or the respective vehicle, the address of the respective venue or the position or location of the vehicle, as determined by the global positioning system device 90K of the venue/vehicle computer 90, and the time and date of the detected entry into or onto, or exit from, the respective venue or the respective vehicle.

At step 1303, the central processing computer 20 and/or the personal monitoring device 10 can receive the signal or the message and can process information contained or included in the same. At step 1303, the central processing computer 20 and/or the personal monitoring device 10 can process information regarding the address of the venue or the position or location of the vehicle at the time of the detected entry or exit from same, using information regarding the monitored individual's travel itinerary, itinerary, or travel schedule, which is stored in the respective databases 20H of the central processing computer 20 and/or the database 10H of the personal monitoring device 10, in order to determine if the monitored individual is traveling in accordance with, or following, his or her travel itinerary, itinerary, or travel schedule, or in order to determine if the monitored individual is not traveling in accordance with, or is not following, or has deviated from, his or her travel itinerary, itinerary, or travel schedule, or in order to determine if the monitored individual may be lost or in need of assistance. In a preferred embodiment, the central processing computer 20 and/or the personal monitoring device 10 can compare the location, time, and day, or the detection of the RFID tag 70, on or associated with the personal monitoring device 10, with the monitored individual's travel itinerary, itinerary, or travel schedule, in order to ascertain whether or not the monitored individual is located at his or her expected location or location of travel, or in close vicinity of same.

At step 1303, the central processing computer 20 and/or the personal monitoring device 10 can generate itinerary or travel notification message which can contain and/or can include information identifying the monitoring individual, information regarding the date and time of the detection of the RFID tag 70, information identifying the respective venue or the respective vehicle, information regarding whether the monitored individual is following his or her travel itinerary, itinerary, or travel schedule, or in order to determine if the monitored individual is not following, or has deviated from, his or her travel itinerary, itinerary, or travel schedule, or may be lost or in need of assistance.

In a preferred embodiment, in the case of the monitored individual entering into or onto a venue, the itinerary or travel notification message can contain and/or can include information regarding the address of the venue and a contact individual and contact telephone number for the venue. In a preferred embodiment, in the case of the monitored individual entering into or onto a vehicle, the itinerary or travel notification message can contain and/or can include information for identifying the vehicle, identifying the type of vehicle (such as, for example, a private car or vehicle, a car service vehicle, a ride-sharing vehicle (such as an Uber vehicle or a LYFT vehicle), a mass transportation vehicle, a bus, a train, a subway train, a boat of any type, kind or size, or an aircraft or helicopter of any type, kind, or size), and/or make and model information and/or vehicle identification information for the vehicle, information regarding the vehicle operator, and/or contact information for the vehicle and/or the vehicle operator and/or a telephone number for the vehicle owner or the vehicle operator. In a preferred embodiment, in the case of the monitored individual entering into or onto a vehicle, the itinerary or travel notification message can also contain and/or can include information regarding the position or location of the vehicle at the time the monitored individual enters into to onto the vehicle. In a preferred embodiment, the position or location of the vehicle can be determined and/or ascertained by the global positioning device 90K of the venue/vehicle computer 90 associated with the respective venue or the respective vehicle.

In a preferred embodiment, the itinerary or travel notification message can contain and/or can include information for providing notification that the monitored individual is following his or her travel itinerary, itinerary, or travel schedule, or that the monitored individual is not following, or has deviated from, his or her travel itinerary, itinerary, or travel schedule, or that the monitored individual may be lost or in need of assistance.

At step 1303, the central processing computer 20 and/or the personal monitoring device 10 can transmit the itinerary or travel notification message to the user communication device 30 which is used by, associated with, or assigned to, the monitoring individual for the monitored individual. In a preferred embodiment, for example, the monitoring individual can be a parent, a grandparent, a sibling, a relative, a friend, a guardian, or any other authorized person. In a situation where the monitored individual may be monitored by more than one monitoring individual, then the central processing computer 20 and/or the personal monitoring device 10 can, at step 1303, transmit the itinerary or travel notification message to the user communication device 30 which is used by, associated with, or assigned to, each such monitoring individual. In a preferred embodiment, the central processing computer 20 and/or the personal monitoring device 10 can also, at step 1303, transmit the itinerary or travel notification message to any law enforcement communication device(s) 40 and/or to any emergency services provider communication device(s) 50, if needed or desired.

In a preferred embodiment, at any time before, during, or after, steps 1302 and/or 1303, the monitoring individual can utilize the user communication device 30 in order to access the central processing computer 20 and/or the personal monitoring device 10 in order to monitor the position or location of the personal monitoring device 10, and the monitored individual, either indirectly via and using the central processing computer 20 or directly by accessing the personal monitoring device 10. In a preferred embodiment, in the case of the monitored individual entering a vehicle, the monitoring individual can track and view the movement of the vehicle on a digital map which is displayed via the display device 30E of the user communication device 30. In a preferred embodiment, at any time during 1302 or 1303, the monitoring individual can also utilize the user communication device 30 to communicate with the personal monitoring device 10 and the monitored individual.

In a preferred embodiment, at step 1303, any user or operator of any law enforcement communication device(s) 40 and/or of any emergency services provider communication device(s) 50 can also utilize the same in order to monitor the position or location of the personal monitoring device 10 and the monitored individual via the central processing computer 20 and/or directly by accessing the personal monitoring device 10, and/or in order to communicate with the personal monitoring device 10 and the monitored individual and/or to communicate with any authorized user of any user communication device 30 used to monitor the monitored individual. In a preferred embodiment, in the case of the monitored individual entering a vehicle, the user or operator of the respective law enforcement communication device(s) 40 or the respective emergency services provider communication device(s) 50 can also track and view the movement of the vehicle on a digital map which is displayed via the respective display device 40E or 50E of the respective law enforcement communication device(s) 40 or the respective emergency services provider communication device(s) 50.

At step 1304, the user communication device 30, and/or the respective law enforcement communication device(s) 40 or the respective emergency services provider communication device(s) 50, can receive the itinerary or travel notification message. At step 1304, the monitoring individual can access the information contained in the itinerary or travel notification message can ascertain that the monitored individual is following his or her travel itinerary, itinerary, or travel schedule, or that the monitored individual is not following, or has deviated from, his or her travel itinerary, itinerary, or travel schedule, or that the monitored individual may be lost or in need of assistance. The operation of the apparatus 100 can then proceed to step 1305.

At step 1305, if the monitored individual is determined to be following his or her travel itinerary, itinerary, or travel schedule, then the monitoring individual may chose to either take no further action or perform any one or more of the actions described herein as being capable of being performed by the apparatus 100 at step 1305. At step 1305, if the monitored individual is determined to not be following, or has deviated from, his or her travel itinerary, itinerary, or travel schedule, or that the monitored individual may be lost or in need of assistance, then the monitoring individual can perform any one or more of the actions described herein as being capable of being performed by the apparatus 100 at step 1305. In a preferred embodiment, any user of any user or operator of any respective law enforcement communication device(s) 40 or the respective emergency services provider communication device(s) 50, can also receive, and review the information contained in, itinerary or travel notification message, and can perform any one or more of the actions described herein as being capable of being performed by the apparatus 100 at step 1305.

At step 1305, the personal monitoring device 10 can perform any of the functions or functionality described herein as being performed by the personal monitoring device 10 at steps 1205 of the preferred embodiment of FIGS. 12A and 12B. At step 1305, the monitoring individual can utilize his or her user communication device 30 to perform any of the functions or functionality described herein as being capable of being performed by the user communication device 30 and/or the apparatus 100 during step 1205 of the preferred embodiment of FIGS. 12A and 12B. At step 1305, the respective law enforcement communication device(s) 40 or the respective emergency services provider communication device(s) 50 can also be utilized to perform any of the functions or functionality described herein as being capable of being performed by the user communication device 30 and/or the apparatus 100 during step 1205 of the preferred embodiment of FIGS. 12A and 12B. At step 1305, the central processing computer 20 can also perform any and/or all of the functions or functionality described as being performed by the central processing computer 20 during step 1205 of the preferred embodiment of FIGS. 12A and 12B.

At step 1306, the central processing computer 10 can store, in the database 10H of the same, any data and/or information regarding the detected and/or read RFID tag 70, any data and/or information contained in any signal or message generated as a result of the detected RFID tag 70, any data and/or information contained in the itinerary or travel notification message, the itinerary or travel notification message, and/or any other information regarding any action performed by the monitoring individual, by any user of any user communication device 30, and/or by any user or operator of a the respective law enforcement communication device 40 or a respective emergency services provider communication device 50, in a travel log or travel history of or for the monitored individual. In a preferred embodiment, at any time, the monitoring individual or any other authorized person can utilize a user communication device 30, a law enforcement communication device 40, or an emergency services provider communication device 50, in order access the central processing computer 20 and to request and receive any data and/or information regarding the travel log or travel history of or for the monitored individual or any other monitored individual. Thereafter, the operation of the apparatus 100 will cease at step 1307.

It is important to note that the apparatus 100 and the personal monitoring device 10 of FIG. 13 can be utilized in a same, a similar, and/or an analogous, manner to monitor individuals of any age, including but not limited to infants, children, adolescents, teenagers, adults of any age, elderly individuals, individuals having no healthcare issues, conditions, problems, or challenges, and/or individuals having healthcare issues, conditions, problems, or challenges. The apparatus 100 and method of the present invention, as well as the apparatus of FIG. 13, can be used to monitor children who may be afflicted with autism, or any disabilities, or who may lack communications skills, and/or who may have other conditions, as well as individuals of any age who are afflicted with Alzheimer's disease or Dementia, or any other healthcare conditions. The apparatus 100 and method of the present invention, as well as the apparatus of FIG. 13, can also be used to monitor individuals of any age who may have no healthcare conditions or problems, but who might want to simply utilize the apparatus 100 and method of the present inventions for the numerous benefits it can provide.

In a preferred embodiment, any of the functions and/or functionality described herein as being performed by the personal monitoring device 10 at or during step 1305 can be pre-programmed into the personal monitoring device 10 beforehand by any authorized individual and/or by a monitoring individual. In a preferred embodiment, any of the functions and/or functionality described herein as being performed by the personal monitoring device 10 at or during step 1305 can be changed or can be re-programmed at any time. In another preferred embodiment, any functions and/or functionality described herein as being performed by the personal monitoring device 10 at or during step 1305 can also be enabled, disabled, activated, deactivated, or controlled, or monitored, by or via the user communication device 30, the central processing computer 20, the law enforcement communication device 40, or the emergency services provider communication device 50.

In another preferred embodiment, as well as in any and/or all of the embodiments described herein, the apparatus 100 and/or the personal monitoring device 10 can also be utilized to record information regarding any incidents of bullying, harassment, criminal acts, or any other activities or events, perpetrated on, inflicted upon, or occurring involving the monitored individual and/or occurring in the vicinity of the monitored individual. In such an embodiment, the personal monitoring device 10 can be activated to record audio information and/or video information regarding the event or the occurrence, the position or location of same, date and time of same, and/or any other pertinent information regarding same which can be obtained by, with, or using, the personal monitoring device 10. In a preferred embodiment, a monitored individual can manually activate the personal monitoring device 10. In another preferred embodiment, the personal monitoring device 10 can be equipped with voice activation equipment and/or hardware and/or software and can be activated to record any information regarding an event or occurrence by, or in response to, a voice activation command. In a preferred embodiment, any data and/or information recorded can be stored in the database 10H of the personal monitoring device 10 and/or can be transmitted to the user communication device(s) 30 of or associated with the monitoring individual, to the central processing computer 20, and/or to any one of more law enforcement communication devices 40 and/or emergency services provider communication devices 50, for reporting and for storing as evidence.

The apparatus 100 and method of the present invention can be utilized in order to provide and support comprehensive personal monitoring services of a global nature for individuals of any age. The apparatus 100 and method of the present invention can also be utilized in order to provide and support comprehensive personal monitoring services of a global nature for individuals of any age and regardless of whether or not they have any conditions, illnesses, sicknesses, disabilities, or health conditions. The apparatus 100 and method of the present invention can also be utilized to provide and service personal monitoring accounts for any number of individuals, with such personal monitoring accounts facilitating the providing of personal monitoring services by and/or involving any number of various monitoring services providers, security services provider, healthcare providers, healthcare insurers, healthcare records service providers, and/or healthcare payers, and/or law enforcement agencies and/or departments, and/or emergency services providers agencies and/or departments.

In another preferred embodiment, as well as any and/or all of the embodiments described herein, any of the herein-described personal monitoring device(s) 10, user communication devices 30, law enforcement communication devices 40, and/or emergency services provider communications devices 50, can be configured and/or adapted to work in an entirely hands-free mode of operation. In this regard, any of the herein-described personal monitoring device(s) 10, user communication devices 30, law enforcement communication devices 40, and/or emergency services provider communications devices 50, can be configured and/or adapted so that they, as well as any operation or functionality of same, can be activated, deactivated, enabled, disabled, controlled, or monitored, by voice-activation, so that any data, information, commands, directions, or instructions, can be input be entered by voice command, and/or so that or so that any data, information, commands, directions, or instructions, can be provided by or from the respective device 10, 30, 40, and/or 50, in the form of audio or audio information.

In another preferred embodiment, any of the herein-described personal monitoring devices 10, user communication devices 30, law enforcement communication devices 40, and/or emergency services provider communications devices 50, can each be equipped with any needed or desired hardware, circuitry, software, software programs, algorithms, and/or software applications ("apps") for performing any and/or all of their respective functions and operations described herein. In another preferred embodiment, any of the herein-described personal monitoring devices 10, user communication devices 30, law enforcement communication devices 40, and/or emergency services provider communications devices 50, can each be equipped with a "kill" switch functionality so that, if lost or stolen, the respective device(s) 10, 30, 40, and/or 50, cannot be utilized by and/or cannot be misappropriated by another individual or person and any data and/or information stored therein can be erased and destroyed completely.

In any and/or all of the embodiments described herein, the apparatus 100 and method of the present invention can also be utilized in a same, a similar, and/or an analogous, manner in order to monitor the movements and/or whereabouts of vehicles of all types or kinds, shipping containers and/or articles of luggage of all types, kinds, or sizes, and/or articles of any type or kind. In such an application, the personal monitoring device 10 can be attached to, or located in, the respective vehicle, the respective shipping container or article of luggage, or the respective article, or the components of the personal monitoring device 10 can be integrated with or within the respective vehicle, the respective shipping container or article of luggage, or the respective article.

While the present invention has been described and illustrated in various preferred and alternate embodiments, such descriptions are merely illustrative of the present invention and are not to be construed to be limitations thereof. In this regard, the present invention encompasses all modifications, variations, and/or alternate embodiments, with the scope of the present invention being limited only by the claims which follow.

What is claimed is:

1. An apparatus, comprising:
a personal monitoring device, wherein the personal monitoring device is assigned to an individual, and further wherein the personal monitoring device comprises:
a database, wherein the database stores information regarding a travel itinerary or a travel schedule of the individual;
a global positioning device;
a first processor;
a first transmitter; and
an RFID tag;
an RFID reader, wherein the RFID reader is located at an entrance of, or at an exit of, a venue or wherein the RFID reader is located at an entrance of, or at an exit of, a vehicle; and
a computer, wherein the computer is assigned to the venue or the vehicle; wherein the computer further comprises:
a second processor; and
a second transmitter,
wherein the RFID reader detects or reads the RFID tag as the RFID tag enters into or onto the venue or the vehicle or as the RFID tag exits from the venue or the vehicle, and further wherein the computer generates a first message containing information regarding a date and a time when the RFID tag was detected or read by the RFID reader and information regarding an address of the venue or information regarding a position or location of the vehicle, and further wherein the computer transmits the first message to a user communication device, to the personal monitoring device, or to a central processing computer,
and further wherein the global positioning device determines a position or location of the personal monitoring device, and further wherein the personal monitoring device processes information regarding the address of the venue or information regarding the position or location of the vehicle using the information regarding the travel itinerary or the travel schedule of the individual, and further wherein the personal monitoring device determines that the individual is not following the travel itinerary or the travel schedule, or wherein the personal monitoring device determines that the individual has deviated from the travel itinerary or the travel schedule, and further wherein the personal monitoring device generates a second message, wherein the second message is an itinerary deviation message or a travel route deviation message, and further wherein the second message contains information regarding a location of the individual, and further wherein the personal monitoring device transmits the second message to the user communication device.

2. The apparatus of claim 1, wherein the personal monitoring device initiates a cellular telephone call or a wireless telephone call to the user communication device.

3. The apparatus of claim 1, wherein the apparatus automatically and continuously monitors the position or location of the personal monitoring device.

4. The apparatus of claim 1, wherein the first processor detects movement of the personal monitoring device.

5. The apparatus of claim 1, wherein the second message is an itinerary deviation message indicating that the individual is not at an expected location.

6. The apparatus of claim 1, wherein the second message is a travel route deviation message indicating that the individual has deviated from a travel route or has gone off course from a travel route.

7. The apparatus of claim 1, wherein the personal monitoring device obtains, determines, reads, or records, physiological information or healthcare information regarding the individual.

8. The apparatus of claim 1, wherein the itinerary deviation message or the travel route deviation message contains information regarding a temperature of an environment in which the individual is located.

9. The apparatus of claim 1, wherein the personal monitoring device de-activates a call on/off switch or an on/off switch functionality of the personal monitoring device to prevent the personal monitoring device from being disconnected from a telephone call or a conference line.

10. The apparatus of claim 1, wherein the personal monitoring device automatically detects the personal monitoring device being disconnected from, or dropped from, a telephone call or a conference line, and further wherein the personal monitoring device automatically re-connects the telephone call or the conference line.

11. The apparatus of claim 1, wherein the personal monitoring device further comprises:
a speakerphone, and further wherein the personal monitoring device activates the speakerphone or a speakerphone functionality.

12. The apparatus of claim 1, wherein the personal monitoring device further comprises:
a camera or a video recording device, and further wherein the personal monitoring device activates the camera or the video recording device.

13. The apparatus of claim 1, wherein the personal monitoring device further comprises:
an indicator light or a plurality of indicator lights, and further wherein the personal monitoring device activates the indicator light or the plurality of indicator lights to indicate that the individual is outside of a "safe" zone of travel.

14. The apparatus of claim 1, wherein the personal monitoring device records video and audio information, and further wherein the personal monitoring device transmits the video and audio information to the user communication device.

15. The apparatus of claim 14, wherein the personal monitoring device transmits the video and audio information to a central processing computer, to a law enforcement communication device, or to an emergency services communication device.

16. The apparatus of claim 1, wherein the user communication device transmits a control signal to the personal monitoring device to enable, to disable, to activate, to de-activate, to control an operation of, or to monitor an operation of, the personal monitoring device or a component of the personal monitoring device.

17. The apparatus of claim 1, wherein the personal monitoring device provides information, or a link to information, regarding or contained in a healthcare record of the individual.

18. The apparatus of claim 1, wherein the personal monitoring device is a wearable device.

19. The apparatus of claim 1, wherein the personal monitoring device is a cellular telephone or a smart phone, or wherein the personal monitoring device is a watch.

20. An apparatus, comprising:
- a personal monitoring device, wherein the personal monitoring device is assigned to an individual, and further wherein the personal monitoring device comprises:
  - a database, wherein the database stores information regarding a travel itinerary or a travel schedule of the individual;
  - a global positioning device;
  - a first processor;
  - a first transmitter; and
  - an RFID tag;
- an RFID reader, wherein the RFID reader is located at an entrance of, or at an exit of, a venue or wherein the RFID reader is located at an entrance of, or at an exit of, a vehicle; and
- a computer, wherein the computer is assigned to the venue or the vehicle; wherein the computer further comprises:
  - a second processor; and
  - a second transmitter,
- wherein the RFID reader detects or reads the RFID tag as the RFID tag enters into or onto the venue or the vehicle or as the RFID tag exits from the venue or the vehicle, and further wherein the computer generates a first message containing information regarding a date and a time when the RFID tag was detected or read by the RFID reader and information regarding an address of the venue or information regarding a position or location of the vehicle, and further wherein the computer transmits the first message to a user communication device, to the personal monitoring device, or to a central processing computer,
and further wherein the global positioning device determines a position or location of the personal monitoring device, and further wherein the personal monitoring device processes information regarding the address of the venue or information regarding the position or location of the vehicle using the information regarding the travel itinerary or the travel schedule of the individual, and further wherein the personal monitoring device determines that the individual is not following the travel itinerary or the travel schedule, or wherein the personal monitoring device determines that the individual has deviated from the travel itinerary or the travel schedule, and further wherein the personal monitoring device generates a second message, wherein the second message is an itinerary deviation message or a travel route deviation message, and further wherein the second message contains information regarding a location of the individual, and further wherein the personal monitoring device transmits the second message to the user communication device or to the central processing computer, and further wherein the personal monitoring device obtains, determines, reads, or records, physiological information or healthcare information regarding the individual.

* * * * *